United States Patent [19]

Russell et al.

[11] Patent Number: 5,684,198
[45] Date of Patent: Nov. 4, 1997

[54] METHOD OF PREPARING THERAPEUTIC AMIDES

[75] Inventors: Keith Russell, Newark; Cyrus John Ohnmacht, Wilmington, both of Del.; Keith Hopkinson Gibson, Macclesfield, England

[73] Assignee: Imperial Chemical Industries, PLC, England

[21] Appl. No.: 701,820

[22] Filed: Aug. 23, 1996

Related U.S. Application Data

[60] Continuation of Ser. No. 476,007, Jun. 7, 1995, Pat. No. 5,565,477, which is a division of Ser. No. 329,188, Oct. 26, 1994, Pat. No. 5,474,999, which is a division of Ser. No. 126,350, Sep. 24, 1993, Pat. No. 5,382,598, which is a division of Ser. No. 918,982, Jul. 23, 1992, Pat. No. 5,272,163.

[30] Foreign Application Priority Data

Jul. 25, 1991 [GB] United Kingdom ............... 9116069
Apr. 30, 1992 [GB] United Kingdom ............... 9209416

[51] Int. Cl.$^6$ .............. C07C 235/16; C07D 213/38; C07D 213/75
[52] U.S. Cl. .............. 564/202; 544/318; 544/333; 544/335; 544/408; 546/223; 546/262; 546/275; 546/280; 546/283; 546/284; 546/292; 546/294; 546/309; 546/316; 548/187; 548/200; 548/213; 548/214; 548/228; 548/229; 548/232; 548/236; 548/243; 549/66; 549/72; 549/475; 549/487; 558/44; 560/107; 560/255; 564/123; 564/189; 564/190
[58] Field of Search .............. 544/318, 333, 544/335, 408; 546/223, 262, 275, 280, 283, 284, 292, 294, 309, 316; 548/187, 200, 213, 214, 228, 229, 232, 236, 243; 549/66, 72, 475, 487; 558/44; 560/107, 255; 564/123, 189, 190, 202

[56] References Cited

U.S. PATENT DOCUMENTS

| | | | |
|---|---|---|---|
| 3,365,485 | 1/1968 | Bell | 540/123 |
| 3,468,878 | 9/1969 | Bell | 540/123 |
| 3,715,375 | 2/1973 | Shen et al. | 260/397.6 |
| 4,191,775 | 3/1980 | Glen | 424/304 |
| 4,239,776 | 12/1980 | Glen | 424/304 |
| 4,282,218 | 8/1981 | Glen et al. | 424/240 |
| 4,294,851 | 10/1981 | Metz et al. | 424/311 |
| 4,386,080 | 5/1983 | Crossley et al. | 424/209 |
| 4,535,092 | 8/1985 | Hughes | 514/438 |
| 4,636,505 | 1/1987 | Tucker | 514/256 |
| 4,880,839 | 11/1989 | Tucker | 514/613 |
| 5,032,592 | 7/1991 | Hughes et al. | 514/256 |
| 5,272,982 | 12/1993 | Russell et al. | 514/347 |

FOREIGN PATENT DOCUMENTS

| | | |
|---|---|---|
| 0 181 568 | 5/1986 | European Pat. Off. . |
| 0 189 142 | 7/1986 | European Pat. Off. . |
| 0 253 503 | 1/1988 | European Pat. Off. . |
| 0 274 867 | 7/1988 | European Pat. Off. . |
| 0 409 413 | 1/1991 | European Pat. Off. . |
| 0 409 414 | 1/1991 | European Pat. Off. . |
| 7008627-Q | 6/1969 | Netherlands . |
| 7008629-Q | 6/1969 | Netherlands . |

OTHER PUBLICATIONS

R Bayles et al., "The Smiles rearrangement of 2–aryloxy–2–methylpropanamides. Synthesis of N–aryl–2–hydroxy–2–methylpropanamides" *Synthesis*. (1977), 31–33.

G Edwards et al., "Structure–activity relationships of potassium channel openers", *Trends in Pharmacological Sciences*. (1990), 11, 417–422.

*Primary Examiner*—Richard L. Raymond
*Attorney, Agent, or Firm*—Liza D. Hohenschutz

[57] ABSTRACT

Amides having formula I:

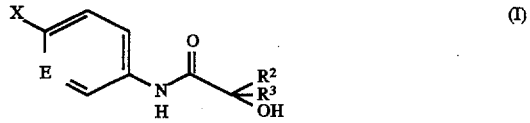

wherein E, X, $R^2$ and $R^3$ have the meanings given in the specification, and pharmaceutically acceptable salts and pharmaceutically acceptable in vivo hydrolysable esters thereof, which are useful in the treatment of urinary incontinence. Further provided are processes for preparing the aides and pharmaceutical compositions containing them.

4 Claims, No Drawings

METHOD OF PREPARING THERAPEUTIC AMIDES

This is a continuation of application Ser. No. 08/476,007 filed on Jun. 7, 1995, now U.S. Pat. No. 5,565,477, which is a divisional application of application Ser. No. 08/329,188 filed Oct. 26, 1994, now U.S. Pat. No. 5,474,999, which is a divisional application of application Ser. No. 08/126,350 filed Sep. 24, 1993 (now U.S. Pat. No. 5,382,598) which is in turn a divisional application of application Ser. No. 07/918,982 filed Jul. 23, 1992 (now U.S. Pat. No. 5,272,163).

This invention relates to compounds useful as cell potassium channel openers in mammals such as man. More specifically, the invention relates to certain substituted amides which are useful in the treatment of urinary incontinence in mammals. Because compounds according to the invention function to open cell potassium channels, they may also be useful as therapeutic agents in the treatment of conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, renal cholic, disorders associated with kidney stones, irritable bowel syndrome, male pattern baldness, premature labor, impotence, and peptic ulcers.

Treatment using a compound of the invention can be remedial or therapeutic as by administering a compound following the onset or development of urinary incontinence in a patient. Treatment can also be prophylactic or prospective by administering a compound in anticipation that urinary incontinence may develop, for example in a patient who has suffered from incontinence in the past.

It is known that bladder tissue is excitable and that urinary incontinence can be caused by uncontrolled or unstable bladder contractions. It is further known that by functioning to open potassium channels, potassium channel opening compounds can thereby function to relax smooth muscle. While not wishing to be bound by theory, it is accordingly believed that the compounds of this invention function by opening potassium channels in bladder cells and thereby relax bladder smooth muscle tissue, thus preventing or ameliorating uncontrolled bladder contractions which can cause urinary incontinence.

This invention provides an amide having formula I (formula set out, together with other formulae referred to in the specification by Roman numerals, on pages following the Examples), wherein:

E is selected from nitrogen and CZ wherein C is a ring carbon and Z is a substituent defined below, wherein:

when E is CZ, X and Z are selected from the group consisting of:

(A) X is ArY wherein Y is a linking group selected from carbonyl, sulfinyl, and sulfonyl and Ar is selected from the group consisting of:
  phenyl substituted with 0–2 substituents selected from halo, hydroxy, cyano, (1–4C)alkyl, and (1–4C)alkoxy, provided that the 4-position of said phenyl may be substituted by fluoro only, and that the said phenyl may not be 3,5-disubstituted;
  six-membered heteroaryl rings containing 1–2 nitrogen atoms as the only heteroatoms;
  five-membered heteroaryl rings containing from 1–2 heteroatoms selected from nitrogen, oxygen, and sulfur;

provided that Ar is not 3-chlorophenyl, 3-bromophenyl, 3-iodophenyl, 3-(1–4C)alkylphenyl, or 4-pyridyl when Y is carbonyl, and that Ar is not 5-pyrimidinyl when Y is sulfonyl or carbonyl; and Z is selected from hydrogen, cyano, halo, hydroxy, (1–4C)alkyl, and (1–4C)alkoxy;

(B) X is cyano and Z is selected from the group consisting of phenylthio, phenylsulfinyl, and phenylsulfonyl the phenyl rings of which are substituted with 0–2 substituents selected from halo, hydroxy, cyano, nitro, (1–4C)alkyl, and (1–4C)alkoxy;

when E is nitrogen, X is independently selected from any of the values for X given above in (A);

$R^2$ and $R^3$ are independently selected from the group consisting of (1–3C)alkyl substituted by from 0 to 2k+1 groups selected from fluoro and chloro wherein k is the number of carbon atoms in the said (1–3C) alkyl, provided that $R^2$ and $R^3$ are not both methyl; or together, with the carbon atom to which both $R^2$ and $R^3$ are attached, form a 3–5 membered cycloalkyl ring optionally substituted by from 0 to 2m-2 fluoro groups wherein m is the number of carbon atoms in said ring;

and pharmaceutically acceptable in vivo hydrolyzable esters of said amide;

and pharmaceutically acceptable salts of said amides and said esters.

The invention further provides a method for the treatment of urinary incontinence, comprising administering to a mammal (including man) in need of such treatment an effective amount of an amide of formula I as defined above, or a pharmaceutically acceptable in vivo hydrolyzable ester or pharmaceutically acceptable salt thereof.

The invention further provides a pharmaceutical composition suitable for the treatment of urinary incontinence comprising an amide of formula I as defined above, or a pharmaceutically acceptable in vivo hydrolyzable ester or pharmaceutically acceptable salt thereof, and a pharmaceutically acceptable diluent or carrier.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

It will be appreciated by those skilled in the art that certain compounds of formula I contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of urinary incontinence, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of urinary incontinence by the standard tests described hereinafter.

Particular values of Ar as phenyl substituted with 0–2 substituents include phenyl, 2- and 3-halophenyl, 4-fluorophenyl, 2-, and 3-hydroxyphenyl, 2-, and 3-cyanophenyl, 2- and 3- methylphenyl, 2- and 3-ethylphenyl, 2- and 3-propylphenyl, 2- and 3-methoxyphenyl, 2- and 3-ethoxyphenyl, 2- and 3-propoxyphenyl, 2,5-difluorophenyl, and 2,3-difluorophenyl.

Particular values of Ar as a six-membered heteroaryl ring containing 1–2 nitrogen atoms include 2, 3-, and 4-pyridyl, 2-pyrazinyl, 2- and 4-pyrimidinyl, and 3- and 4-pyridazinyl.

Particular values of Ar as a five-membered heteroaryl ring containing from 1–2 heteroatoms selected from nitrogen, oxygen, and sulfur include 3-, 4- and 5-isothiazolyl, 2-, 4- and 5-oxazolyl, 2-, 4- and 5-thiazolyl, 2- and 3-furyl, and 2- and 3-thienyl.

Particular values of Z as (1–4C)alkyl include methyl, ethyl, propyl, isopropyl, butyl, isobutyl, sec-butyl, and tert-butyl.

Particular values of Z as (1–4C)alkoxy include methoxy, ethoxy, propoxy, isopropoxy, butoxy, isobutoxy, sec-butoxy, and tert-butoxy.

Particular values of Z as phenylthio substituted with from 0–2 substituents include phenylthio, 2-, 3-, and 4-halophenylthio, 2-, 3-, and 4-hydroxyphenylthio, 2-, 3-, and 4-cyanophenylthio, 2-, 3-, and 4-methylphenylthio, 2-, 3-, and 4-ethylphenylthio, 2-, 3-, and 4-propylphenylthio, 2-, 3-, and 4-methoxyphenylthio, 2-, 3-, and 4-ethoxyphenylthio, 2-, 3-, and 4-propoxyphenylthio, 2,4-difluorophenylthio, and 2,3-difluorophenylthio.

Particular values of Z as phenylsulfinyl substituted with from 0–2 substituents include phenylsulfinyl, 2-, 3-, and 4-halophenylsulfinyl, 2-, 3-, and 4-hydroxyphenylsulfinyl, 2-, 3-, and 4-cyanophenylsulfinyl, 2-, 3-, and 4-methylphenylsulfinyl, 2-, 3-, and 4-ethylphenylsulfinyl, 2-, 3-, and 4-propylphenylsulfinyl, 2-, 3-, and 4-methoxyphenylsulfinyl, 2-, 3-, and 4-ethoxyphenylsulfinyl, 2-, 3-, and 4-propoxyphenylsulfinyl, 2,4-difluorophenylsulfinyl, and 2,3-difluorophenylsulfinyl.

Particular values of Z as phenylsulfonyl substituted with from 0–2 substituent include phenylsulfonyl, 2-, 3-, and 4-halophenylsulfonyl, 2-, 3-, and 4-hydroxyphenylsulfonyl, 2-, 3-, and 4-cyanophenylsulfonyl, 2-, 3-, and 4-methylphenylsulfonyl, 2-, 3-, and 4-ethylphenylsulfonyl, 2-, 3-, and 4-propylphenylsulfonyl, 2-, 3- and 4-methoxyphenylsulfonyl, 2-, 3-, and 4-ethoxyphenylsulfonyl, 2-, 3-, and 4-propoxyphenylsulfonyl, 2,4-difluorophenylsulfonyl, and 2,3-difluorophenylsulfonyl.

Particular values of R2 and R3 as (1–3C)alkyl substituted by from 0 to 2k+1 groups selected from fluoro and chloro include methyl, ethyl, propyl, isopropyl, chloromethyl, dichloromethyl, chlorodifluoromethyl, trichloromethyl, 1-chloroethyl, 1,1-dichloroethyl, 2-chloroethyl, 2,2-dichloroethyl, 2,2,2-trichloroethyl, 1,2-dichloroethyl, 1,1,2-trichloroethyl, 1,2,2-trichloroethyl, 1,1,2,2-tetrachloroethyl, 1,2,2,2-tetrachloroethyl, 1,1,2,2,2-pentachloroethyl, 1-chloropropyl, 1,1-dichloropropyl, fluoromethyl, difluoromethyl, trifluoromethyl, 1-fluoroethyl, 1,1-difluoroethyl, 2-fluoroethyl, 2,2-difluoroethyl, 2,2,2-trifluoroethyl, 1,2-difluoroethyl, 1,1,2-trifluoroethyl, 1,2,2-trifluoroethyl, 1,1,2,2-tetrafluoroethyl, 1,2,2,2-tetrafluoroethyl, 1,1,2,2,2-pentafluoroethyl, 1-fluoropropyl, and 1,1-difluoropropyl.

Particular values of 3–5 membered cycloalkyl rings substituted by from 0 to 2m-2 fluoro groups, which can be formed by R2 and R3 together with the carbon atom to which $R^2$ and $R^3$ are attached, include cyclopropyl, cyclobutyl, cyclopentyl, 2-fluorocyclopropyl, 2,2-difluorocyclopropyl, 2,3-difluorocyclopropyl, 2,2,3-trifluorocyclopropyl, 2,2,3,3-tetrafluorocyclopropyl, 2-fluorocyclobutyl, 3-fluorocyclobutyl, 2,3-difluorocyclobutyl, 2,4-difluorocyclobutyl, 2,2-difluorocyclobutyl, 2,3,4-trifluorocyclobutyl, 2,3,3-trifluorocyclobutyl, 2,2,3-trifluorocyclobutyl, 2,2,4-trifluorocyclobutyl, 2,2,3,4-tetrafluorocyclobutyl, 2,3,3,4-tetrafluorocyclobutyl, 2,2,3,3-tetrafluorocyclobutyl, 2,2,4,4-tetrafluorocyclobutyl, 2,2,3,3,4-pentafluorocyclobutyl, 2,2,3,4,4-pentafluorocyclobutyl, hexafluorocyclobutyl, 2-fluorocyclopentyl, 3-fluorocyclopentyl, 2,2-difluorocyclopentyl, 2,3-difluorocyclopentyl, 2,4-difluorocyclopentyl, 2,5-difluorocyclopentyl, 3,3-difluorocyclopentyl, 2,2,3-trifluorocyclopentyl, 2,2,4-trifluorocyclopentyl, 2,2,5-trifluorocyclopentyl, 2,3,3-trifluorocyclopentyl, 3,3,4-trifluorocyclopentyl, 2,4,4-trifluorocyclopentyl, 2,2,3,3-tetrafluorocyclopentyl, 2,2,4,4-tetrafluorocyclopentyl, 2,2,5,5-tetrafluorocyclopentyl, 3,3,4,4-tetrafluorocyclopentyl, 2,2,3,4-tetrafluorocyclopentyl, 2,2,3,5-tetrafluorocyclopentyl, 2,2,4,5-tetrafluorocyclopentyl, 2,3,3,4-tetrafluorocyclopentyl, 2,3,3,5-tetrafluorocyclopentyl, 3,3,4,5-tetrafluorocyclopentyl, 2,3,4,5-tetrafluorocyclopentyl, 2,2,3,3,4-pentafluorocyclopentyl, 2,2,3,3,5-pentafluorocyclopentyl, 2,2,3,4,4-pentafluorocyclopentyl, 2,2,3,5,5-pentafluorocyclopentyl, 2,2,3,4,5-pentafluorocyclopentyl, 2,3,3,4,4-pentafluorocyclopentyl, 2,3,3,5,5-pentafluorocyclopentyl, 2,3,3,4,5-pentafluorocyclopentyl, 2,2,3,3,4,4-hexafluorocyclopentyl, 2,2,3,3,5,5-hexafluorocyclopentyl, 2,2,3,3,4,5-hexafluorocyclopentyl, 2,3,3,4,4,5-hexafluorocyclopentyl, 2,3,3,4,4,5-hexafluorocyclopentyl, 2,3,3,4,5,5-hexafluorocyclopentyl, 2,2,3,4,4,5-hexafluorocyclopentyl, 2,2,3,3,4,4,5-heptafluorocyclopentyl, 2,2,3,3,4,5,5-heptafluorocyclopentyl, and octafluorocyclopentyl.

A more particular value for E is CZ wherein Z is selected from the more particular values defined below.

More particular values of Ar as phenyl substituted with 0–2 substituents include those values of phenyl substituted with 0–1 substituent, including phenyl, 2-, 3- and 4-fluorophenyl, 2- and 3-chlorophenyl, 2- and 3-cyanophenyl, 2- and 3-hydroxyphenyl, 2- and 3-methoxyphenyl, and 2- and 3-methylphenyl.

More particular values of Ar as a six-membered heteroaryl ring containing 1–2 nitrogen atoms include 2, 3-, and 4-pyridyl, and 2- and 4-pyrimidinyl.

More particular values of Ar as a five-membered heteroaryl ring containing from 1–2 heteroatoms include 3- and 4-isothiazolyl, 2- and 4-oxazolyl, 2- and 4-thiazolyl, 2- and 3-furyl, and 2- and 3- thienyl.

More particular values of Z as (1–4C)alkyl include values of (1–2C)alkyl, including methyl and ethyl.

More particular values of Z as (1–4C)alkoxy include values of (1–2C)alkoxy, including methoxy and ethoxy.

More particular values of Z as phenylthio substituted with from 0–2 substituents include those values of phenylthio substituted with 0–1 substituent, including phenylthio, 2-, 3- and 4-fluorophenylthio, 2-, 3-, and 4-chlorophenylthio, 2-, 3- and 4-cyanophenylthio, 2-, 3- and 4-hydroxyphenylthio, 2-, 3- and 4-methoxyphenylthio, and 2-, 3- and 4-methylphenylthio.

More particular values of Z as phenylsulfinyl substituted with from 0–2 substituents include those values of phenylsulfinyl substituted with 0–1 substituent, including phenylsulfinyl, 2-, 3- and 4-fluorophenylsulfinyl, 2-, 3- and 4-chlorophenylsulfinyl, 2-, 3- and 4-cyanophenylsulfinyl, 2-, 3- and 4-hydroxyphenylsulfinyl, 2-, 3- and 4-methoxyphenylsulfinyl, and 2-, 3- and 4-methylphenylsulfinyl.

More particular values of Z as phenylsulfonyl substituted with from 0–2 substituents include those values of phenylsulfonyl substituted with 0–1 substituent, including phenylsulfonyl, 2-, 3- and 4-fluorophenylsulfonyl, 2-, 3-, and 4-chlorophenylsulfonyl, 2-, 3-, and 4-cyanophenylsulfonyl, 2-, 3-, and 4-hydroxyphenylsulfonyl, 2-, 3-, and 4-methoxyphenylsulfonyl, and 2-, 3-, and 4-methylphenylsulfonyl.

More particular values of R2 and R3 as (1–3C)alkyl substituted by from 0 to 2k+1 groups selected from chloro and fluoro include those substituted with fluoro groups only, including fluoromethyl, difluoromethyl, trifluoromethyl, 1-fluoroethyl, 1,1-difluoroethyl, 2-fluoroethyl, 2,2-difluoroethyl, 2,2,2-trifluoroethyl, 1,2-difluoroethyl, 1,1,2-trifluoroethyl, 1,2,2-trifluoroethyl, 1,1,2,2-tetrafluoroethyl, 1,2,2,2-tetrafluoroethyl, and 1,1,2,2,2-pentafluoroethyl.

A particular amide has formula Id wherein:

X and Z are selected from the group consisting of:
  (A) X is ArY wherein
    Y is a linking group selected from carbonyl, sulfinyl, and sulfonyl and Ar is selected from the group consisting of phenyl, 2-, 3- and 4-fluorophenyl, 2- and 3-chlorophenyl, 2- and 3-cyanophenyl, 2- and 3-hydroxyphenyl, 2- and 3-methoxyphenyl, 2- and 3-methylphenyl, 2, 3-, and 4-pyridyl, 2- and 4-pyrimidinyl, 3- and 4-isothiazolyl, 2- and 4-oxazolyl, 2- and 4-thiazolyl, 2- and 3-furyl, and 2- and 3-thienyl;
    Z is selected from hydrogen, cyano, halo, hydroxy, (1–2C)alkyl, and (1–2C)alkoxy;
  (B) X is CN, Z is phenylsulfonyl;

$R^2$ and $R^3$ are independently selected from the group consisting of (1–3C)alkyl substituted by from 0 to 2k+1 fluoro groups wherein k is the number of carbon atoms in the said (1–3C)alkyl, provided that $R^2$ and $R^3$ are not both methyl;

and pharmaceutically acceptable in vivo hydrolyzable esters of said amide;

and pharmaceutically acceptable salts of said amides and said esters.

A preferred amide has formula Id wherein X is ArY, and wherein:

Ar, Y, and Z are selected from the group consisting of:
  (i) Y is sulfonyl, Z is hydrogen, and Ar is selected from the group consisting of:
    phenyl substituted with 0–1 substituents, selected from phenyl, 2-, 3-, and 4-fluorophenyl, 2- and 3-chlorophenyl, 2- and 3-methoxyphenyl, 2- and 3-cyanophenyl, 2- and 3-hydroxyphenyl, and 2- and 3-methylphenyl;
    six-membered heteroaryl rings selected from 2-, 3- and 4-pyridyl, and 2-pyrimidinyl;
    five-membered heteroaryl rings selected from 2-thienyl and 2-thiazolyl;
  (ii) Y is sulfonyl, Ar is phenyl or 4-pyridyl, and Z is selected from the group consisting of cyano, fluoro, hydroxy, methoxy and methyl; and
  (iii) Y is carbonyl, Z is hydrogen, and Ar is selected from the group consisting of phenyl and 2-pyridyl; and R2 and R3 are independently selected from the group consisting of (i) $R^2$ is trifluoromethyl and $R^3$ is selected from methyl, ethyl, and trifluoromethyl; and
  (ii) $R^2$ is difluoromethyl and $R^3$ is difluoromethyl;

and the pharmaceutically acceptable in vivo hydrolyzable esters of said amide, and pharmaceutically acceptable salts of said amide and said hydrolyzable esters.

Where applicable, the S-configuration generally represents a preferred sterochemistry for compounds according to the invention.

Specifically preferred amides include the following:

N-[4-(4-Pyridylsulfonyl)phenyl]-3,3,3-trifluoro-2-hydroxy-2-methylpropanamide;

S-(−)-N-[4-(4-Pyridylsulfonyl)phenyl]-3,3,3-trifluoro-2-hydroxy-2-methylpropanamide;

N-[4-(Phenylcarbonyl)phenyl]-3,3,3-trifluoro-2-hydroxy-2-methylpropanamide;

S-(−)-N-[4-(Phenylcarbonyl)phenyl]-3,3,3-trifluoro-2-hydroxy-2-methylpropanamide;

N-[4-(4-Pyridylsulfonyl)phenyl]-3,3-difluoro-2-hydroxy-2-difluoromethylpropanamide;

N-[4-(Phenylcarbonyl)phenyl]-3,3,3-trifluoro-2-hydroxy-2-trifluoromethylmethylpropanamide;

N-[4-(4-Pyridylsulfonyl)phenyl]-3,3,3-trifluoro-2-hydroxy-2-trifluoromethylpropanamide; and N-[3-Hydroxy-4-(4-pyridylsulfonyl)phenyl]-3,3,3-trifluoro-2-hydroxy-2-methylpropanamide.

The above compounds are preferred because they are selective for the bladder without significant effect on the cardiovascular system, as measured by blood pressure effects, in the in vivo test predictive of selectivity which is described herein.

Amides of formula I can be made by processes which include processes known in the chemical arts for the production of structurally analogous compounds. Such processes for the manufacture of an amide of formula I as defined above are provided as further features of the invention and are illustrated by the following procedures in which the meanings of generic radicals are as given above unless otherwise qualified. Such a process can be effected, generally, (a) by coupling an aniline of formula II with an acid of formula III wherein G is a hydroxy group. The reaction can be conducted in a suitable solvent and in the presence of a suitable coupling reagent. Suitable coupling reagents generally known in the the art as standard peptide coupling reagents can be employed, for example thionyl chloride, (see Morris et. al., J. Med. Chem., 34, 447, (1991)), carbonyldiimidazole (CDI) and dicyclohexylcarbodiimide, optionally in the presence of a catalyst such as dimethylaminopyridine (DMAP) or 4-pyrrolidinopyridine. Suitable solvents include dimethylacetamide, dichloromethane, benzene, tetrahydrofuran, and dimethylformamide. The coupling reaction can be conducted in a temperature range of about −40° to 40° C.;

(b) by deprotecting a protected amide having formula IV wherein "PG" is a suitable protecting group such as a benzyl group; Examples of suitable reactants for use in cleaving the ether moiety to yield a hydroxyl group include (1) hydrogen in the presence of palladium-on-carbon catalyst, i.e. hydrogenolysis; (2) hydrogen bromide or iodide; (3) trimethylsilyl iodide; and (4) alkyl sulfides or phosphides. The reaction can be conducted in a suitable solvent such as ethanol, methanol, acetonitrile, or dimethylsulfoxide and at a temperature in the range of about −40° to 100° C.

(c) in a compound of formula I wherein X is substituted or unsubstituted phenylsulfinyl or phenylsulfonyl, by oxidizing a corresponding substituted or unsubstituted phenylsulfide. Suitable oxidizing agents include potassium permanganate, oxone, sodium periodate, and hydrogen peroxide. The reaction can be conducted in a suitable solvent such as diethyl ether, methanol, ethanol, water, acetic acid, and mixtures of two or more of the aforementioned. The reaction can be conducted at a temperature of −40° to 70° C.

(d) by reacting an amide of formula V with a base sufficiently basic (e.g., a lithium dialkylamide such as lithium diisopropyl amide) to yield an amide dianion, followed by reacting the dianion thereby produced with oxygen in the presence of a reducing agent (e.g., such as triphenyl phosphine) to yield the corresponding compound of formula I; The sequence of reactions can be conducted at a temperature in the range of about −100° to −20° C. in a suitable solvent such as tetrahydrofuran or diethyl ether.

(e) in a compound of formula Id wherein X is substituted or unsubstituted phenylsulfonyl by reacting a corresponding substituted or unsubstituted compound of formula V I, wherein the value corresponding to X is substituted or unsubstituted phenylsulfonyl and Hal indicates a halogen substituent (e.g. the corresponding chloride) with a corresponding alkali metal amide dianion having formula VII wherein Am is an alkali metal such as sodium or lithium; The reaction can be conducted at a temperature in the range of about −40° to about 100° C. and in a suitable solvent such as dimethylformamide dimethylsulfoxide or tetrahydrofuran.

(f) by reacting an (alkyl ester) compound of formula VIII wherein $R^4$ is a (1–4C)alkyl group (e.g. methyl, ethyl or propyl) with a (2–3C)alkyl magnesium halide (i.e. a Grignard reagent); The reaction a Grignard addition to an ester, can be conducted at a temperature of about −100° to about 20° C. in a suitable solvent such as tetrahydrofuran or diethyl ether. Higher alkyl esters can be employed but they provide no synthetic advantage.

(g) when X is substituted or unsubstituted benzoyl (in formula I) by reacting a corresponding compound of formula IXa with a corresponding substituted or unsubstituted triphenylaluminum or tetraphenyltin and carbon monoxide in the presence of a suitable catalyst such as bis-(triphenylphosphine)palladium (II) chloride; The reaction may be conducted at a temperature of from about −20° to about 100° C. in a suitable solvent such as benzene toluene, tetrahydrofuran or diethyl ether.

(h) when X is substituted or unsubstituted benzoyl, by oxidizing a compound of formula IXb to the corresponding compound of formula I wherein X is the corresponding substituted or unsubstituted benzoyl moiety; Oxidizing agents such as bromine and pyridinium dichromate and solvents such as, respectively, methanol and dichloromethane can be suitably employed.

If not commercially available the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples. In the discussion which follows, "At" refers to an unsubstituted or substituted phenyl group or a heterocyclic radical, as previously defined.

In general, compounds of formulae IV, V, VIII, IXa, and IXb can be made in a manner analogous to that described in procedure (a) above for making an amide of formula I; that is, by coupling an appropriate corresponding aniline with an appropriate corresponding acid. Thus, to make a protected amide of formula IV, a corresponding aniline of formula II can be coupled with an acid of formula III wherein the group corresponding to G is OPG. The protected acid can be made by a conventional procedure, for example by (i) esterifying an acid of formula III wherein G is hydroxy by means of a conventional esterification procedure such as reaction with a lower alcohol (e.g., methanol) in the presence of an acid catalyst (for example sulfuric acid); (ii) reaction of the ester thus formed with an agent which provides the protecting group PG, such as benzyl chloride (to provide a benzyl protecting group) or any of the conventional silylating agents known and used for such purpose (such as 2-trimethylsilylethoxymethyl chloride, SEM, in the presence of a suitable base such as sodium hydroxide or triethylamine optionally in the presence of a catalyst such as DMAP); and (iii) cleavage of the ester group under mild alkaline conditions (i.e., employing a base such as potassium carbonate) to yield the desired protected acid.

As a further example, a compound of formula IXa can be made by coupling an acid of formula III wherein G is hydroxy with an aniline of formula II wherein the group corresponding to X is iodo and E is CH. It will be appreciated by those skilled in the art that compounds having the other formulae noted above can be prepared in an analogous manner using appropriate corresponding starting materials.

An aniline of formula XI wherein n=0, 1, or 2 (i.e., an aniline of formula II wherein X is ArS, ArSO, or $ArSO_2$) can be made by reducing the corresponding nitro compound of formula XII with a suitable reducing agent as generally known in the art, see A. Courtin, Helv, Chim,. Acta, 66, 1046 (1983); and H. Gilman et. al., J. Amer. Chem. Soc., 69, 2053, (1947). Suitable reducing agents include stannous chloride dihydrate in ethanol conducted at a temperature of 20° to reflux, iron in water-ethanol conducted at a temperature of 20° to reflux, and catalytic hydrogenation using palladium or platinum catalyst conducted at a temperature of 20° to 50° C.

An aniline of formula XI wherein n=2 can also be made by the acid hydrolysis (aqueous HCl/ethanol at reflux) of an acetanilide of formula XIII to afford the corresponding aniline.

A nitro compound of formula XII wherein n=1 or 2 can be made by oxidizing the corresponding compound of formula XII wherein n=0 (i.e. the corresponding sulfide), thereby yielding the corresponding compound of formula XII wherein n=1 or 2, as desired. Suitable reagents for the preparation of n=1 are sodium periodate in a suitable solvent such as methanol or dioxane conducted at a temperature of 20° to 80°; bromine and potassium carbonate in methylene chloride/water conducted at room temperature; and 30% hydrogen peroxide in acetic acid conducted at room temperature. Suitable reagents for the preparation of n=2 are potassium permanganate in acetic acid/water conducted at room temperature; 30% hydrogen peroxide in acetic acid conducted at 70°; oxone in methanol/water conducted at room temperature; and m-chloroperbenzoic acid in methylene chloride conducted at a temperature of 0° to reflux.

A nitro compound of formula XII wherein n=0 or 2 can also be made by reacting a corresponding alkali metal acid salt of formula ArSO$_n$Am, wherein Am is an alkali metal such as sodium, lithium, or potassium, with a halide of formula XIV wherein Hal indicates a halo substituent (such as chloro). The reaction is conducted in solvents such as ethanol/water, dimethylformamide or dimethylacetamide at a temperature of 20° to 155°.

A nitro compound of formula XII, wherein n=0 or 2, can also be made by reacting a corresponding compound of formula ArHal wherein Hal is halogen (for example 2-chloro-5-nitropyridine) with a corresponding salt of formula XV (n=0 or 2) wherein Am is an alkali metal such as sodium, lithium or potassium. The reaction is conducted in solvents such as ethanol/water, dimethylformamide or dimethylacetamide at a temperature of 20° to 155°.

An aniline of formula XVI can be made by reacting a corresponding acid of formula ArCO$_2$H or a corresponding anhydride of formula ArCO—O—COAr with aniline in the presence of polyphosphonic acid. See, for example, B,. Staskum, J. Org. Chem., 29, 2856, (1964) and A. Denton et. al., J. Chem. Soc., 4741, (1963).

It is noted that many of the starting materials for synthetic methods as described above are commercially available and/or widely reported in the scientific literature.

In cases where compounds of formula I (or Id) are sufficiently basic or acidic to form stable acid or basic salts, administration of the compound as a salt may be appropriate, and pharmaceutically acceptable salts can be made by conventional methods such as those described following. Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride. Pharmaceutically acceptable salts may be obtained using standard procedures well known in the art, for example by reacting a sufficiently basic compound of formula I (or its ester) with a suitable acid affording a physiologically acceptable anion. It is also possible with most compounds of the invention to make a corresponding alkali metal (e.g., sodium, potassium, or lithium) or alkaline earth metal (e.g., calcium) salt by treating an amide of formula I (and in some cases the ester) with one equivalent of an alkali metal or alkaline earth metal hydroxide or alkoxide (e.g. the ethoxide or methoxide in aqueous medium followed by conventional purification techniques.

In vivo hydrolyzable esters of compounds of the invention can be made by coupling with a pharmaceutically acceptable carboxylic acid or an activated derivative thereof. For example, the coupling can be carried out by treating a parent amide of formula I with an appropriate acid chloride (for example, acetyl chloride, propionyl chloride, or benzoyl chloride) or acid anhydride (for example, acetic anhydride, propionic anhydride, or benzoic anhydride) in the presence of a suitable base such as triethylamine. Those skilled in the art will appreciate that other suitable carboxylic acids (including their activated derivatives) for the formation of in vivo hydrolyzable esters are known to the art and these are also intended to be included within the scope of the invention. Catalysts such as 4-dimethylaminopyridine can also be usefully employed.

When used to treat urinary incontinence, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular (i.e., directly into the bladder), subcutaneous or intramuscular injection or infusion; or in the form of a patch for transdermal administration.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective oral dose is received, generally a daily dose in the range of about 50 to about 500 mg. For the specific compounds previously noted as being preferred because they are bladder selective, an effective oral dose can range from a total daily dose of 50 mg up to a dose of about 2000 mg. No untoward effects have been observed in laboratory animals following administration of compounds according to the invention at several multiples of the minimum effective dose in the animal tests described hereinafter.

It will be apparent to those skilled in the art that a compound of formula I can be co-administered with other therapeutic or prophylactic agents and/or medicaments that are not medically incompatible therewith.

The actions of compounds of formula I as smooth muscle relaxants useful as therapeutic agents for the treatment of urinary incontinence can be shown using suitably designed in vitro tests, such as the one described following. Compounds according to the invention typically exhibit an $IC_{50}$ on the order of 30 micromolar or less in the test. "IC50" is a well understood term and means the concentration of test compound which causes a 50% decrease in the in vitro contraction of the bladder tissue described in the following test.

Male albino Hartley guinea pigs (450–500 g) are sacrificed by cervical dislocation. The lower abdominal cavity is opened and the urinary bladder located. Once located, it is cleaned of surrounding connective and adipose tissue. The two pelvic nerves on the ventral surface of the bladder are cut away, then the bladder body is removed above the entrance of the ureters. The bladder is washed in Krebs-Henseleit buffer solution (composition (mM): NaCl 118.0, KCl 4.7, MgSO$_4$ 1.2, KH$_2$PO$_4$ 1.2, CaCl$_2$ 2.5, NaHCO$_3$ 25 and D-Glucose 11.1) and then placed on a buffer-soaked gauze in a petri dish. The dome of the bladder is cut off and discarded.

A mid-ventral longitudinal cut is made with scissors and the bladder laid flat on the gauze. Strips are cut from the dome edge and the base edge and discarded. The remaining detrusor mid-section is cut into two latitudinal (horizontal) strips, with an approximate width of 2.0 mm. These two strips are cut in half at the mid-dorsal section, creating four strips of similar dimensions. Each strip thus contains both dorsal and ventral portions of the bladder.

Each individual strip is tied at one end directly to a glass support rod and a length of 4-0 black braided silk suture is tied to the other end. The glass rods are secured in 20 ml tissue baths and the length of suture attached to a force-displacement transducer (Grass model FT03).

The tissues are bathed in Krebs-Henseleit buffer solution. The bathing solution is warmed to 37° C. and gassed with 5% $CO_2$ and 95% $O_2$, with vigorous bubbling. The solution should have a pH value close to 7.4.

The transducers are connected to a polygraph (Grass model 7E) and interfaced with a Modular Instrument Micro 5000 signal processing system and Biowindow Data Acquisition Software (run on Microsoft OS/2 with an IBM-compatible PC)

The polygraph is calibrated at 5 mV/cm and calibration checked for linearity with weights of 5 and 0.5 grams.

The tissue is incubated in the buffer for 15 minutes without preload tension, then 30 minutes with tension applied. The preload tension applied is 2 grams that relaxes to approximately 1 gram. The tissue is washed at 15 minute intervals, with tension adjusted to 2 grams just prior to washing. After this 45 minute equilibration period, a priming dose of 15 mM KCl (total concentration in bath) is applied. The tissue is washed after 10 minutes and washed twice more at 15 minute intervals with tension adjusted to 2 grams before each washing.

When the tissue relaxes to a steady state after the final washing, 15 mM KCl is again dosed. Once the tissue reaches a steady state the base line data are acquired on the Biowindows Data Acquisition System. This is done by averaging 5 minutes of data, sampling at 32 Hz. Once the baseline is acquired, the experimental compounds are dosed in a cumulative manner in half log unit increments. The contact time for each dose is 10 minutes with the final 5 minutes being the period of time that the dose response data are acquired. If 30M of the test compound does not abolish detrusor mechanical activity, then 30M cromakalim is dosed to establish a maximum response. The effects of the compounds are expressed as % of maximum relaxation of agonist induced tension.

Typical $IC_{50}$ values in the above test are 1.27±0.31 μM for the compound of Example 1 and 5.14±1.89 μM for the compound of Example 2.

It will be further appreciated by those skilled in the art that the efficacy of compounds according to the invention can be demonstrated by standard assays in vivo. The following is a description of such a standard test which is used to evaluate smooth muscle relaxing capability of test compounds.

Male Wistar rats weighing 450–550 grams are anesthetized with 20 mg/kg, intraperitoneal (i.p.) Nembutal and 80 mg/kg, i.p. Ketamine. The trachea is cannulated to prevent airway obstruction. Body temperature is maintained by means of a heating pad. Arterial blood pressure and heart rate are measured with a pressure transducer connected to a polyethylene tube (PE 50) which has been inserted into the right carotid artery. The right jugular vein is cannulated for drug administration. The urinary bladder is exposed through a midline abdominal incision and emptied of urine by application of slight manual pressure. A catheter (PE 50) is inserted through the apex of the bladder dome around 3–4 mm into its lumen and tied with suture (4–0 silk) to prevent leakage. The bladder catheter is connected to a pressure transducer for the measurement of bladder pressure. The bladder is then placed back into the abdominal cavity and the incision is stitched closed except where the catheter exits the cavity. The bladder is allowed to equilibrate for approximately 15 minutes. After the equilibration period, the rats are infused with saline directly into the bladder at a rate of 0.05 ml/min for the entire time of the experiment. The bladder pressure is then monitored for the start of bladder contractions. When the contractions start the animal is then allowed to stabilize its pattern of contractions around 30 to 45 minutes before drug administration.

The test compounds are given intravenous and the cutoff dose is 3 mg/kg. The reference drug cromakalim (Smithkline-Beecham) has been evaluated in this model and administered intravenous over the dose range of 0.05 to 0.5 mg/kg.

The above in vivo assay enables an assessment of both the blood pressure and cystometric activity of test compounds. Blood pressure is measured immediately after drug injection and at 5, 15 and 30 minutes later. Micturition contractions are induced by a slow continuous infusion of saline directly into the bladder. The average change (in seconds from control) in the duration of the intercontraction interval (the time between contractions) over an approximate 20-min period is reported for each compound.

Typical results are indicated for the Examples noted in Table 1 which follows:

TABLE 1

| CMPD | DOSE | CHANGE IN MBP | | | | CHANGE IN IC |
|---|---|---|---|---|---|---|
| | | Immed. | 5 min | 15 min | 30 min | |
| Example 5 | 3 | −63 | −52 | −37 | −28 | +77 |

Dose is mg/kg.
MBP = mean arterial blood pressure. The values are mmHg and reflect changes from control. The times shown are the immediate (Immed.) effect and the effects at 5, 15, and 30 minutes after i.v. compound administration.
IC = intercontraction interval. Change in IC = peak response in seconds from control.

The following is a description of a test in vivo which is complimentary to the above described tests and which can be used to ascertain if a test compound is active and, additionally, if the test compound exhibits selectivity for the bladder without significant cardiovascular effects when dosed orally. The specifically preferred compounds noted previously are active and selective in this test.

Male Wistar rats (400–500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the catheters were implanted according to the method of Yaksh TL, Durant PAC, Brent CR. Micturition in rats: A chronic model for study of bladder function and effect of anesthesia. Am. J. Physiol. 251 (Regulatory Integrative Comp. Physiol. 20): R1177–R1185, 1986. The bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24–48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (0.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45–90 min.). At this point, a basal level of each experimental parameter was recorded and the rats were administered by oral gavage the appropriate dose of compound (in a 75% PEG 400—saline vehicle) in concentrations such that the volume was 1 ml/kg body weight. The effects of the compounds on experimental parameters were followed for five hours after administration. Cromakalim (Smithkline-Beecham) was used as the reference standard.

Experimental results for both the interval between contractions and also heart rates were expressed as the mean ± S.E.M. % change from basal level, with each animal serving as its own control. MAP is expressed as mean ± S.E.M mm Hg change from basal level. Typical values are listed in Table 2 for the Examples noted.

TABLE 2

| Compound | Dose (mg/kg)[1] | Time[2] | CIC[3] | CMBP[4] (mmHg) | % CHR[5] |
| --- | --- | --- | --- | --- | --- |
| cromakalim | 1.0 | 1 | 54 ± 5 | −18 ± 4 | 20 ± 5 |
|  |  | 2 | 76 ± 15 | −18 ± 6 | 15 ± 4 |
|  |  | 3 | 104 ± 5 | −14 ± 5 | 13 ± 2 |
|  |  | 4 | 129 ± 5 | −11 ± 4 | 10 ± 4 |
|  |  | 5 | 114 ± 25 | −12 ± 3 | 9 ± 4 |
| example 61 | 3 mg/kg | 1 | 35 ± 3 | 1 ± 1 | −3 ± 2 |
|  |  | 2 | 53 ± 5 | −1 ± 1 | −4 ± 3 |
|  |  | 3 | 65 ± 5 | −2 ± 1 | −2 ± 4 |
|  |  | 4 | 57 ± 5 | −1 ± 2 | −2 ± 3 |
|  |  | 5 | 90 ± 10 | −4 ± 1 | −2 ± 2 |
| example 59 | 3 mg/kg | 1 | 39 ± 5 | 0 ± 2 | 1 ± 1 |
|  |  | 2 | 74 ± 11 | 1 ± 2 | 2 ± 3 |
|  |  | 3 | 96 ± 9 | −1 ± 1 | 0 ± 4 |
|  |  | 4 | 108 ± 6 | −2 ± 1 | 2 ± 2 |
|  |  | 5 | 124 ± 9 | −7 ± 1 | 3 ± 4 |

1. mg/kg is milligrams per kilogram of body weight.
2. Time is measured in hours following (post) dosage.
3. CIC is an acronym for change in intercontraction interval of the bladder.
4. CMBP is an acronym for change in the mean arterial blood pressure.
5. % CHR is an acronym for percentage of change in heart rate.
Note: All values are relative to controls.

Compounds according to the invention are active in one or more of the above-described tests. With reference to those (preferred) compounds previously listed as exhibiting selectivity for the bladder, most compounds from that list have also been tested in vivo in a dog model, and all which were tested exhibited activity and selectivity.

The invention will now be illustrated by the following non-limiting examples in which, unless stated otherwise:

(i) temperatures are given in degrees Celsius (C.); operations were carried out at room or ambient temperature, that is, at a temperature in the range of 18°–25°;

(ii) evaporation of solvent was carried out using a rotary evaporator under reduced pressure (600–4000 pascals; 4.5–30 mm Hg) with a bath temperature of up to 60 °;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) reduced pressures are given as absolute pressures in pascals (Pa); other pressures are given as gauge pressures in bars;

(ix) chemical symbols have their usual meanings; the following abbreviations have also been used: v (volume), w (weight); mp (melting point), L [liter(s)], mL (milliliters), mmol (millimoles), g [gram(s)], mg [milligram(s)], min (minutes), h (hour); and (x) solvent ratios are given in volume:volume (v/v) terms.

EXAMPLE 1

N-[4-(2-Fluorophenylsulfonyl)phenyl]-3,3,3,-trifluoro-2-hydroxy-2-methyl propanamide To a stirred, cooled (−20° C.) solution of 3,3,3-trifluoro-2-hydroxy-2-methyl propanoic acid (1.42 g 9.0 mmol) in N,N-dimethylacetamide (13 mL) was rapidly added thionyl chloride (1.13 g, 9.5 mmol) and the mixture (a precipitate formed after a few minutes) stirred at −15° to −5° C. for 1 hour. 4-(2-Fluorophenylsulfonyl)benzenamine (1.51 g, 6.0 mmol) was then added in one portion and the mixture allowed to stir at room temperature overnight. The solution was poured into water, the cloudy solution decanted from the resulting gum and filtered through a thin pad of Celite. The Celite pad was washed with methylene chloride and the solution added to a solution of the gum in methylene chloride. The combined methylene chloride solution was dried ($MgSO_4$), filtered and the solvent removed in vacuo. The resulting gum was treated with hexane (100 mL) and enough methylene chloride (ca. 100 mL) to yield a solution. Methylene chloride was then boiled off on a steam bath at atmospheric pressure until cloudiness developed. The solution was cooled and scratched with a spatula until crystal growth began, returned to the steam bath and concentrated with swirling until the final volume was 100 mL. After cooling the solid was filtered to yield the title propanamide (1.92 g, 82%) as a light tan solid; mp 124°–133° C. $^1$H-NMR (400 MHz, $d_6$-DMSO): 1.59 (s, 3H, $CH_3$), 7.41 (t, 1H, aromatic), 7.51 (t, 1H, aromatic), 7.59 (s, 1H, OH), 7.77 (m, 1H, aromatic), 7.85 (d, 2H, J=8.7 Hz, aromatic), 7.98–8.06 (m, 3H, aromatic), 10.48 (s, 1H, NH). MS (CI, $CH_4$): 392(M+1).

Analysis for $C_{16}H_{13}F_4NO_4S$: Calculated: C, 49.11; H, 3.35; N, 3.58 Found: C, 49.28; H, 3.51; N, 3.66

The starting 4-(2-fluorophenylsulfonyl)benzenamine is described in N. Sharghi and I. Lalezari, J. Chem. Eng. Data, 8, 276–8 (1963).

EXAMPLE 2

N-[4-(2-Methylphenylsulfonyl)phenyl]-3,3,3,-trifluoro-2-hydroxy-2-methyl propanamide To a stirred, cooled (−15° C.) solution of 3,3,3-trifluoro-2-hydroxy-2-methyl propanoic acid (1.42 g, 9.0 mmol) in N,N-dimethylacetamide (13 mL) was rapidly added thionyl chloride (1.13 g, 9.5 mmol) and the mixture (a precipitate formed after a few minutes) stirred at −20° C. to −10° C. for 1 hour. 4-(2-Methylphenylsulfonyl)benzenamine (1.48 g, 6.0 mmol) was then added in one portion, washed in with 2 mL of N,N-dimethylacetamide and the mixture allowed to stir at room temperature overnight. The solution was poured into water, the cloudy solution decanted from the resulting gum and filtered through a thin pad of Celite. The Celite pad was washed with methylene chloride and the solution added to a solution of the gum in methylene chloride. The combined methylene chloride solution was dried (MgSO$_4$), filtered and the solvent removed in vacuo. The resulting gum was dissolved in a few mL of methanol and added dropwise to 100 mL of rapidly stirred 3N HCl The aqueous phase was decanted from the gum, the gum dissolved in methylene chloride, dried (MgSO$_4$), filtered and the solvent removed in vacuo. The residue was dissolved in 125 mL of methylene chloride and heated on a steam bath as 100 mL of hexane was slowly added to replace the methylene chloride. When a volume of 125 mL was reached more hexane (ca. 50 mL) was added to the cloud point. After cooling overnight the resulting solid was filtered to yield impure product. This material was further stirred with 300 mL of 0.5N HCl for 45 min., the aqueous phase decanted off and the residual gum dissolved in methylene chloride, dried (MgSO$_4$), filtered and the solvent removed in vacuo. The material was dissolved in 100 mL of methylene chloride, 50 mL of hexane added and the solution heated on a steam bath to a final volume of 100 mL. After cooling the resulting solid was filtered and dried at 100°–120° C./0.1 torr. for 2.5 hours to yield the title propanamide (1.78 g, 77%) as a light tan solid; mp 126°–128° C. $^1$H-NMR (300 MHz, d$_6$-DMSO): 1.58 (s, 3H, CH$_3$), 2.39 (s, 3H, aryl CH$_3$), 7.37–8.10 (m, 8H, aromatic), 7.6 (broad s, 1H, OH), 10.4 (broad s, 1H, NH). MS (CI, CH$_4$): 388(M+1).

Analysis for $C_{17}H_{16}F_3NO_4S$: Calculated: C, 52.71; H, 4.16; N, 3.62 Found: C, 52.64; H, 4.16; N, 3.59

The starting 4-(2-Methylphenylsulfonyl)benzenamine is described in H. Gilman and H. Smith Broadbent, J. Amer. Chem. Soc., 69, 2053 (1947).

EXAMPLE 3

N-[4-(2-Methoxyphenylsulfonyl)phenyl]-3,3,3,-trifluoro-2-hydroxy-2-methyl propanamide To a stirred, cooled (−15° C.) solution of 3,3,3-trifluoro-2-hydroxy-2-methylpropanoic acid (1.42 g 9.0 mmol) in N,N-dimethylacetamide (13 mL) was rapidly added thionyl chloride (1.13 g, 9.5 mmol) and the mixture (a precipitate formed after a few minutes) stirred at −15° C. to −5° C. for 1 hour. 4-(2-Methoxyphenylsulfonyl)benzenamine (1.58 g, 6.0 mmol) was then added in one portion and the mixture allowed to stir at room temperature overnight. The solution was poured into 300 mL of 0.5N HCl, the clear supernatent decanted off and the residual gum taken up in methylene chloride, dried (MgSO$_4$), filtered and the solvent removed in vacuo. The residue was dissolved in 100 mL of methylene chloride, filtered, treated with 50 mL of hexane and heated briefly on a steam bath until crystals started to form. The final volume was taken to 200 mL with hexane, the mixture refrigerated for 3 hours, and the crystals filtered and washed with hexane. The solid was dissolved in 700 mL of refluxing methylene chloride and methylene chloride boiled off as 250 ml of hexane was slowly added. The mixture was concentrated to a final volume of 375 mL. After cooling the solid was filtered and dried at 135°–140° C./0.1 torr. for 40 hours to yield the title propanamide. 0.1 CH$_2$Cl$_2$ (1.41 g, 57%) as a white solid; mp 209°–211° C. $^1$H-NMR (300 MHz, d$_6$-DMSO): 1.55 (s, 3H, CH$_3$), 3.72 (s, 3H, CH$_3$O), 5.73 (s, 0.2H, CH$_2$Cl$_2$), 7.11–7.17 (m, 2H, aromatic), 7.53 (s, 1H, OH), 7.61–7.97 (m, 6H, aromatic), 10.36 (s, 1H, NH). MS (CI, CH$_4$): 404(M+1).

Analysis for $C_{17}H_{16}F_3NO_5S$: Calculated: C, 49.87; H, 3.96; N, 3.40 Found: C, 49.71; H, 3.96; N, 3.35

The starting 4-(2-methoxyphenylsulfonyl)benzenamine was obtained as follows:

a. 4-(2-Methoxyphenylsulfonyl)benzenamine

To a stirred slurry of 2-methoxyphenyl-4-nitrophenyl sulfone (12.36 g, 4.2 mmol) and 90 mL of absolute ethanol was added stannous chloride dihydrate (47.4 g, 21 mmol) in one portion. The mixture was heated to 50° C. where an exothermic reaction caused the solution to strongly reflux. The mixture was allowed to stir at ambient temperature for 30 min., poured onto ice-water and made strongly basic by the addition of 350 mL of 15% NaOH. The mixture was extracted with methylene chloride (3×275 mL), the extracts dried (MgSO$_4$), filtered, and the solvent removed in vacuo to yield a white solid which was recrystallized from ethyl acetate-hexane. After cooling the solid was filtered to yield the title benzenamine (5.38 g, 49%) as a white solid; mp 206°–208° C. $^1$H-NMR (300 MHz, d$_6$-DMSO): 3.75 (s, 3H, OCH$_3$), 6.10 (s, 2H, NH$_2$), 6.56–6.61 (m, 2H, aromatic), 7.07–7.13 (m, 2H, aromatic), 7.49–7.61 (m, 3H, aromatic), 7.90 (dd, 1H, J =8.1 & 1.7 Hz, aromatic). MS (CI, CH$_4$): 264 (M+1).

Analysis for $C_{13}H_{13}NO_3S$: Calculated: C, 59.30; H, 4.98; N, 5.32 Found: C, 59.28; H, 5.04; N, 5.20 b. 2-Methoxyphenyl-4-nitrophenyl sulfone

To a stirred solution of 2-methoxyphenyl-4-nitrophenyl sulfide (13.73 g, 5.25 mmol) and acetic acid (800 mL) was rapidly added a solution of potassium permanganate (9.97 g, 6.3 mmol) in water (350 mL). After stirring for 45 min. the mixture was poured into water (2 L), clarified by the addition of sodium sulfite and the solid filtered, dried several hours at 40° C./0.1 torr. and recrystallized three times from absolute ethanol (300 mL). The yield of title sulfone was 12.46 g, 81%; white plates, mp 140°–142° C. $^1$H-NMR (300 MHz, CDCl$_3$): 3.79 (s, 3H, OCH$_3$), 6.94 (d, 1H, J=8.4 Hz, aromatic), 7.16 (t, J=7.6 1H, Hz aromatic), 7.58–7.64 (m, 1H, aromatic), 8.13–8.19 (m, 3H, aromatic), 8.31–8.35 (m, 2H, aromatic).

MS (CI, CH$_4$): 294 (M+1).

Analysis for $C_{13}H_{11}NO_5S$: Calculated: C, 53.24; H, 3.78; N, 4.78 Found: C, 53.23; H, 3.79; N, 4.79 c. 2-Methoxyphenyl-4-nitrophenyl sulfide

A solution of 4-chloronitrobenzene (11.23 g, 7.13 mmol) in N,N-dimethylformamide (75 mL) was added to 2-methoxythiophenol potassium salt [prepared by adding 2-methoxythiophenol (10.0 g, 7.13 mmol) to a solution of potassium hydroxide (4.00 g, 7.13 mmol) in methanol followed by removal of the methanol in vacuo] and washed in with an additional 15 ml of N,N-dimethylformamide. After stirring at room temperature overnight the mixture was poured into ice-water, stirred for 1 hour, filtered, the collected solid washed with water and dried overnight at 40° C./0.1 torr. The pale yellow solid was recrystallized from 85% ethanol (150 mL), and then from hexane (700 mL) to yield the title sulfide (13.8 g, 74%) as pale yellow needles, mp 90°–92° C. $^1$H-NMR (300 MHz, CDCl$_3$): 3.82 (s, 3H, OCH$_3$), 7.01–7.06 (m, 2H, aromatic), 7.10–7.15 (m, 2H, aromatic), 7.45–7.55 (m, 2H, aromatic), 8.02–8.07 (m, 2H, aromatic). MS (CI, CH$_4$): 262(M+1).

Analysis for C$_{13}$H$_{11}$NO$_3$S: Calculated: C, 59.76; H, 4.24; N, 5.36 Found: C, 59.95; H, 4.25; N, 4.73

EXAMPLE 4

N-(4-Phenylsulfonyl-3-cyanophenyl)-3,3,3,-trifluoro-2-hydroxy-2-methyl propanamide To a stirred solution of 1.91 g (5.2 mmol) of N-(4-phenylthio-3-cyanophenyl)-3,3,3,-trifluoro-2-hydroxy-2-methylpropanamide and 150 mL of glacial acetic acid was added a solution of 0.99 g (6.3 mmol) of potassium permanganate and 100 mL of water in one portion. The mixture was stirred at ambient temperature for 45 minutes, poured into 400 mL of water, clarified with a little solid sodium bisulfite and extracted with three 250 mL portions of chloroform. The extracts dried (MgSO$_4$), filtered and the solvent removed to yield an oil which was chromatographed on 300 g of silica gel using a ethyl ether (0%, 10%, 15% and 20%) in methylene chloride gradient. The material was further recrystallized from hexane containing a small amount of ethyl acetate to yield 1.57 g (75%) of the title propanamide as a white solid; mp 163°–165° C. $^1$H-NMR (300 MHz, d$_6$-DMSO): 1.59 (s, 3H, CH$_3$), 7.66–7.77 (m, 4H, aromatic, OH), 7.99 (d, 2H, J=7.3 Hz, aromatic), 8.32 (d, 1H, J=8.6 Hz, aromatic), 8.40–8.43 (m, 2H, aromatic), 10.77 (s, 1H, NH). MS (CI, CH$_4$): 399(M+1).

Analysis for C$_{17}$H$_{13}$F$_3$N$_2$O$_4$S: Calculated: C, 51.26; H, 3.29; N, 7.03 Found: C, 51.28; H, 3.31; N, 7.01

The starting N-(4-phenylthio-3-cyanophenyl)-3,3,3,-trifluoro-2-hydroxy-2-methylpropanamide was obtained as follows:

a. N-(4-Phenylthio-3-cyanophenyl)-3,3,3,-trifluoro-2-hydroxy-2-methylpropanamide To a stirred, cooled (−20° C.) solution of 3,3,3-trifluoro-2-hydroxy-2-methylpropanoic acid (2.16 g 13.7 mmol) in N,N-dimethylacetamide (20 mL) was rapidly added thionyl chloride (1.73 g, 14.5 mmol) and the mixture (a precipitate formed after a few minutes) stirred at −20° C. to −10° C. for 1 hour. (4-Amino-2-cyanophenyl)phenyl sulfide (2.08 g, 9.2 mmol) was then added in one portion and the mixture allowed to stir at room temperature overnight. The solution was poured into 500 mL of water and extracted with two 100 mL portions of ethyl ether. The oil obtained on removal of the ethyl ether was chromatographed on 325 g of silica gel using an ethyl ether (0%, 5%, 10% and 20%) in methylene chloride gradient. The proper fractions were combined, the solvent removed in vacuo and the residue heated overnight at 60° C./0.1 mm to yield 5.35 g (93%) of N-(4-phenylthio-3-cyanophenyl)-3,3,3,-trifluoro-2-hydroxy-2-methylpropanamide, mp 124°–126° C. $^1$H-NMR (300 MHz, d$_6$-DMSO): 1.59 (s, 3H, CH$_3$), 7.32–7.47 (m, 6H, aromatic), 7.59 (s, 1H, OH), 8.07 (dd 1H, J=8.8, 2.3 Hz, aromatic), 8.33 (d, 1H, J=2.3 Hz, aromatic), 10.48 (s, 1H, NH). MS (CI, CH$_4$): 367(M+1).

b. 4-Amino-2-cyanophenyl phenyl sulfide

To a stirred slurry of 4-nitro-2-cyanophenyl phenyl sulfide (13.3 g, 5.19 mmol) and 100 mL of absolute ethanol was added stannous chloride dihydrate (58.6 g, 26 mmol) in one portion. The mixture was heated to 60° C. where an exothermic reaction caused the solution to strongly reflux. The mixture was allowed to stir at ambient temperature for 30 min., poured onto ice-water and made strongly basic by the addition of 350 mL of 15% NaOH. The mixture was extracted with methylene chloride (4×275 mL), the extracts dried (MgSO$_4$), filtered, and the solvent removed in vacuo to yield an oil which was chromatographed on 300 g of silica gel using a methylene chloride (20%, 40%, 60% 80% and 100%) in hexane gradient. The proper fractions were combined and the solvent removed to yield the 4-amino-2-cyanophenyl phenyl sulfide (10.62 g, 91%) as a pale yellow solid; mp 73°–75° C. $^1$H-NMR (300 MHz, CDCl$_3$): 4.01 (s, 2H, NH$_2$), 6.78 (dd 1H, J=8.5, 2.6, aromatic), 6.95 (d, 1H, J=2.6, aromatic), 7.18–7.29 (m, 5H, aromatic), 7.34 (d, 1H, J=8.5, aromatic). MS (CI, CH$_4$): 227(M+1).

Analysis for C$_{13}$H$_{10}$N$_2$S: Calculated: C, 69.00; H, 4.45; N, 12.38 Found: C, 68.99; H, 4.59; N, 12.27 c. 4-Nitro-2-cyanophenyl phenyl sulfide

4-Chloro-3-cyanonitrobenzene (12.5 g, 6.84 mmol) was added portionwise to a stirred N,N-dimethylformamide (50 mL) solution of thiophenol potassium salt [prepared by adding thiophenol (7.1 mL, 6.9 mmol) to a solution of potassium hydroxide (3.84 g, 6.84 mmol) in methanol followed by removal of the methanol in vacuo]. After stirring at 105° C. for 2.5 hours the mixture was poured into ice-water, filtered, the collected solid washed with water, dissolved in 300 mL of refluxing ethanol (charcoal), filtered, treated with 35 mL of water and refrigerated. The resulting pale yellow solid weighed 13.3 g (76%), mp 82°–84° C. $^1$H-NMR (250 MHz, CDCl$_3$): 6.93 (d, 1H, J=9.0 Hz, aromatic), 7.51–7.62 (m, 5H, aromatic), 8.12(dd, 1H, J=9.2, 2.5 Hz, aromatic), 8.46 (d, 1H, J=2.5 Hz, aromatic). MS (CI, CH$_4$): 257(M+1).

Analysis for C$_{13}$H$_8$N$_2$O$_2$S: Calculated: C, 60.93; H, 3.15; N, 10.93 Found: C, 60.87; H, 3.41; N, 10.95

EXAMPLE 5

N-[4-(Phenylsulfonyl)phenyl]-3,3,3,-trifluoro-2-hydroxy-2-methylpropanamide

To a stirred, cooled (−20° C.) solution of 3,3,3-trifluoro-2-hydroxy-2-methylpropanoic acid (3.96 g 25 mmol) in N,N-dimethylacetamide (36 mL) was rapidly added thionyl chloride (3.10 g, 26 mmol) and the mixture (a precipitate formed after a few minutes) stirred at −15° C. to −5° C. for 1 hour. 4-(Phenylsulfonyl)benzenamine (3.97 g, 17 mmol) was then added in one portion and the mixture allowed to stir at room temperature overnight. The solution was poured into water, the resulting solid was filtered off, washed with 3N HCl, then water and dried at 65° C. for 2 hours. The solid was dissolved in 300 mL of refluxing methylene chloride and stirred and heated as hexane was added to replace the methylene chloride as it boiled off. When 250 mL of hexane had been added (precipitate formed at about 180 mL addition) the mixture was concentrated to 250 mL and refrigerated. The yield of light tan solid was 5.92 g (93%), mp 164°–166° C. $^1$H-NMR (250 MHz, d$_6$-DMSO): 1.59 (s, 3H, CH$_3$), 7.57–7.72 (m, 4H, OH, aromatic), 7.92–8.04 (m, 6H, aromatic), 10.43 (s, 1H, NH).

Analysis for C$_{16}$H$_{14}$F$_3$NO$_4$S: Calculated: C, 51.47; H, 3.78; N, 3.75 Found: C, 51.22; H, 3.83; N, 3.72

EXAMPLE 6

N-[4-(4-Pyridylsulfonyl)phenyl]-3,3,3-trifluoro-2-hydroxy-2-methylpropanamide

To a stirred, cooled (−20° C.) solution of 3,3,3-trifluoro-2-hydroxy-2-methylpropanoic acid (4.28 g, 30.5 mmol) in N,N-dimethylacetamide (30 mL) was added thionyl chloride (3.63 g, 30.5 mmol) and the mixture stirred at −10° to −15° C. for one hour. 4-(4-Pyridylsulfonyl)benzenamine (4.77 g, 20.4 mmol) was added in one portion and the mixture stirred at room temperature overnight. The solution was poured into water, the yellow solid filtered and purified by flash chromatography (50% v/v ethyl acetate in methylene chloride). Evaporation of the eluent and trituration of the resulting solid with hot methylene chloride yielded the title propanamide (4.61 g, 60%) as an off-white solid; mp 255°–257° C. $^1$H-NMR (300 MHz, $d_6$-DMSO): 1.71 (s, 3H, $CH_3$), 7.71 (s, 1H, OH), 8.01 (d, 2H, J=4.5 Hz, aromatic), 8.12 (d, 2H, J=7.1 Hz, aromatic), 8.19 (d, 2H, J=7.1 Hz, aromatic), 9.00 (d, 2H, J=4.5 Hz, aromatic), 10.61 (s, 1H, NH). MS (CI, $CH_4$): 375(M+1).

Analysis for $C_{15}H_{13}F_3N_2O_4S$: Calculated: C, 48.12; H, 3.51; N, 7.48 Found: C, 48.02; H, 3.59; N, 7.42

The starting 4-(4-pyridylsulfonyl)benzenamine is described in T. Takahashi, J Shibasaki and M. Uchibayashi, Pharm. Bull. (Japan), 2, 30 (1954).

EXAMPLE 7

N-[4-(2-Pyrimidinylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (1.01 g, 6.4 mmol) in N,N-dimethylacetamide (10 mL) was added thionyl chloride (0.76 g, 6.4 mmol) and the mixture stirred at −10° to −15° C. for one hour. 4-(2-Pyrimidylsulfonyl)benzenamine (1.00 g, 4.2 mmol) was added in one portion to the orange solution and the mixture stirred at room temperature overnight. The brown mixture was poured into water and extracted with ethyl acetate (2×50 mL). The combined organic portions were washed with water, dried ($MgSO_4$), filtered, and the solvent distilled to yield a tan solid. Flash chromatography of the solid (eluted with 10% v/v ethyl acetate in methylene chloride) and evaporation of the eluent yielded the title propanamide (1.05 g, 66%) as a white solid; mp 187°–190° C. $^1$H-NMR (300 MHz, $d_6$-DMSO): 1.60 (s, 3H, $CH_3$), 7.59 (s, 1H, OH), 7.79 (t, 1H, J=4.9 Hz, aromatic), 7.96 (d, 2H, J=8.9 Hz, aromatic), 8.06 (d, 2H, J=8.9 Hz, aromatic), 9.02 (d, 2H, J=4.8 Hz, aromatic), 10.49 (s, 1H, NH). MS (CI, $CH_4$): 376 (M+1).

Analysis for $C_{14}H_{12}F_3N_3O_4S$: Calculated: C, 44.80; H, 3.22; N, 11.20 Found: C, 44.86; H, 3.36; N, 11.06

4-(2-Pyrimidylsulfonyl)benzenamine is described in G. H. Singhal, P. M. Thomas and I. C. Popoff, J. Heterocyclic Chem., 5(3), 411 (1968).

EXAMPLE 8

N-[5-(2-Phenylsulfonylpyridyl)]-3,3,3-trifluoro-2-hydroxy-2-methylpropanamide

To stirred solution of N-[5-(2-phenylthiopyridyl)]-3,3,3-trifluoro-2-hydroxy-2-methylpropanamide (1.50 g, 4.4 mmol) in glacial acetic acid (125 mL) was added a solution of potassium permanganate (0.83 g, 5.3 mmol) in distilled water (85 mL). The dark brown mixture was stirred at room temperature for 45 min, then treated with solid sodium sulfite until decolorized. The mixture was diluted with water and extracted with chloroform (3×250 mL). The combined organic portions dried ($MgSO_4$), filtered and the solvent distilled to yield the title propanamide as a white solid; mp 175°–177° C. $^1$H-NMR (300 MHz, $d_6$-DMSO): 1.59 (s, 3H, $CH_3$), 7.65 (m, 4H, OH, aromatic), 7.95 (d, 2H, J=7.5 Hz, aromatic), 8.22 (d, 1H, J=8.7 Hz, aromatic), 8.54 (dd, 1H, J=8.7 and 2.4 Hz, aromatic), 9.00 (d, 1H, J=2.3 Hz, aromatic), 10.73 (s, 1H, NH). MS (CI, $CH_4$): 375(M+1).

Analysis for $C_{15}H_{13}F_3N_2O_4S$: Calculated: C, 48.12; H, 3.51; N, 7.48 Found: C, 47.96; H, 3.62; N, 7.43

The starting N-[5-(2-phenylthiopyridyl)]-3,3,3-trifluoro-2-hydroxy-2-methylpropanamide was obtained as follows: N-[5-(2-Phenylthiopyridyl)]-3,3,3-trifluoro-2-hydroxy-2-methylpropanamide To a stirred, cooled (−20° C.) solution of 3,3,3-trifluoro-2-hydroxy-2-methylpropanoic acid (0.59 g, 3.7 mmol) in N,N-dimethylacetamide (10 mL) was added thionyl chloride (0.44 g, 3.7 mmol) and the mixture stirred at −10° to −15° C. for one hour. 5-Amino-2-phenylthiopyridine (0.50 g, 2.5 mmol) was added in one portion to the orange solution and the mixture stirred at room temperature overnight. The brown mixture was poured into water and the aqueous solution extracted with ethyl acetate (2×50 mL). The combined organic portions were washed with water, dried ($MgSO_4$), filtered, and the solvent distilled to yield a yellow oil. Flash chromatography of the oil (eluted with 10% v/v ethyl acetate in methylene chloride) and evaporation of the eluent yielded the title propanamide (0.59 g, 69%) as a white solid; mp 147°–150° C. $^1$H-NMR (300 MHz, $d_6$-DMSO): 1.57 (s, 3H, $CH_3$), 7.04 (d, 1H, J=8.7 Hz, aromatic), 7.47 (m, 6H, OH, aromatic), 8.05 (dd, 1H, J=8.7 and 2.6 Hz, aromatic), 8.77 (d, 1H, J=2.4 Hz, aromatic), 10.30 (s, 1H, NH). MS (CI, $CH_4$): 343(M+1).

Analysis for $C_{15}H_{13}F_3N_2O_2S$ : Calculated: C, 52.63; H, 3.83; N, 8.18 Found: C, 52.25; H, 3.86; N, 8.13

5-Amino-2-phenylthiopyridine is described in H. C. Winter and F. E. Reinhart, J. Amer. Chem. Soc., 62, 3508 (1940).

EXAMPLE 9

N-[4-(4-Fluorophenylcarbonyl)phenyl]-3,3,3-trifluoro-2-hydroxy-2-methyl propanamide To a stirred, cooled (−20° C.) solution of 3,3,3-trifluoro-2-hydroxy-2-methylpropanoic acid (1.58 g, 10 mmol) in N,N-dimethylacetamide (15 mL) was added thionyl chloride (1.25 g, 10.5 mmol) and the mixture stirred at −20° to −5° C. for 1 hour. 4-Amino-4'-fluorobenzophenone (1.44 g, 6.7 mmol) was added in one portion and the reaction mixture stirred at room temperature overnight. The reaction mixture was poured into water, the cloudy solution decanted from a gum and filtered through a thin pad of Celite. The Celite was washed with methylene chloride and the solution added to a solution of the gum in methylene chloride. The combined methylene chloride solution was dried ($MgSO_4$), filtered and the solvent removed to yield an oil. The oil was treated with 50 mL of hexane and enough methylene chloride to dissolve the oil. The solution volume was reduced slightly on a steam bath and the solution cooled and scratched until crystals formed. The volume was reduced further on the steam bath, the mixture refrigerated for several hours and the resulting solid filtered off. The 1.60 g of impure product was further purified by chromatography on 80 g of flash column silica gel using ethyl ether as eluent. The solvent was stripped from the first 150 mL of eluent, the residual oil dissolved in 15 mL of methylene chloride and added to 250 mL of rapidly stirred hexane. The resulting solid was collected and dried to yield the title propanamide (0.22 g, 58%) as a pale yellow solid; mp 131°–133° C. $^1$H-NMR (250 MHz, $CDCl_3$): 1.77 (s, 3H, $CH_3$), 4.09 (s, 1H, OH), 7.14–7.28 (m, 2H, aromatic), 7.69–7.85 (m, 6H, aromatic), 8.68 (s, 1H, NH). MS (CI, $CH_4$): 356M+1).

Analysis for $C_{17}H_{13}F_4NO_3$: Calculated: C, 57.47; H, 3.69; N, 3.94 Found: C, 57.30; H, 3.65; N, 3.90

The starting 4-amino-4'-fluorobenzophenone is described in B. Staskum, J. Org. Chem., 29, 2856 (1964).

EXAMPLE 10

N-[4-[(3-Pyridylsulfonyl)phenyl]]-3,3,3-trifluoro-2-hydroxy-2-methylpropanamide To a stirred, cooled (−20° C. solution of 3,3,3-trifluoro-2-hydroxy-2-methylpropanoic acid (0.76 g, 4.8 mmol) in N,N-dimethylacetamide (10 mL) was added thionyl chloride (0.57 g, 4.8 mmol) and the mixture stirred at −10° to −15° C. for 1 hour. 4-(3-Pyridylsulfonyl)benzenamine (0.75 g, 3.2 mmol) was added in one portion to the orange solution and the mixture stirred at room temperature overnight. The brown solution was poured into water and extracted with ethyl acetate (2×50 mL). The combined organics were dried ($MgSO_4$), filtered and the solvent distilled to yield a tan solid. Recrystallization from ethyl acetate/hexane yielded the title propanamide (0.89 g, 74%) as an off-white solid; mp 207°–209° C. $^1$H-NMR (300 MHz, $d_6$-DMSO): 1.57 (s, 3H, $CH_3$), 7.58 (s, 1H, OH), 7.65 (dd, 1H, J=8.1, 4.9 Hz, aromatic), 8.02 (d, 4H, J=4.6 Hz, aromatic), 8.34 (dd, 1H, J=8.3, 1.9 Hz, aromatic), 8.85 (dd, 1H, J=4.8, 1.6 Hz, aromatic), 9.12 (d, 1H, J=2.2 Hz, aromatic), 10.61 (s, 1H, NH). MS (CI, $CH_4$): 375(M+1).

Analysis for $C_{15}H_{13}F_3N_2O_4S$: Calculated: C, 48.12; H, 3.51; N, 7.48 Found: C, 48.11; H, 3.56; N, 7.40

The starting 4-(3-Pyridylsulfonyl)benzenamine was obtained as follows:

a. 4-(3-Pyridylsulfonyl)benzenamine

A stirred solution of 4-nitrophenyl 3-pyridyl sulfone (1.60 g, 6.1 mmol) and stannous chloride dihydrate (6.83 g, 30.2 mmol) in absolute ethanol (20 mL) was heated at reflux for 45 min. The reaction mixture was poured into ice water, and the aqueous solution basified with sodium bicarbonate (pH= 8–9) and extracted with ethyl acetate (2×200 mL). The organics were combined, dried ($MgSO_4$), filtered, and the solvent distilled to yield the title benzenamine (1.10 g, 79%) as a pale yellow solid; mp 182°–184° C. $^1$H-NMR (300 MHz, $d_6$-DMSO): 6.29 (broad s, 2H, $NH_2$), 6.64 (d, 2H, J=11.2 Hz, aromatic), 7.58 (m, 1H, aromatic), 7.61 (d, 2H, J=11.1 Hz, aromatic), 8.21 (dd, 1H, J=9.8, 2.4 Hz, aromatic), 8.78 (dd, 1H, J=9.9, 1.4 Hz, aromatic), 9.01 (d, 1H, J=2.4 Hz). MS (CI, $CH_4$): 235(M+1).

Analysis for $C_{11}H_{10}N_2O_2S$: Calculated: C, 56.40; H, 4.30; N, 11.96 Found: C, 56.64; H, 4.54; N, 11.48

The starting 4-nitrophenyl 3-pyridyl sulfone is described in U.S. Pat. No. 2,761,866.

EXAMPLE 11

N-[4-(2-Thienylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (0.50 g, 3.1 mmol) in N,N-dimethylacetamide (7 mL) was added thionyl chloride (0.37 g, 3.1 mmol) and the mixture stirred at −10° to −15° C. for 1 hour. 4-(2-Thienylsulfonyl)benzenamine (0.50 g, 2.1 mmol) was added in one portion to the orange solution and the mixture stirred at room temperature overnight. The brown solution was poured into water and the aqueous solution extracted with ethyl acetate (2×50 mL). The organics were combined, dried ($MgSO_4$), filtered and the solvent distilled to yield a tan solid. Flash chromatography of the solid (eluted with 5% v/v ethyl acetate in methylene chloride) and evaporation of the eluent yielded the title propanamide (0.61 g, 77%) as an off-white solid; mp 158°–161° C. $^1$H-NMR (250 MHz, $d_6$-DMSO): 1.57 (s, 3H, $CH_3$), 7.21 (dd, 1H, J=4.9, 4.0 Hz, aromatic), 7.56 (s, 1H, OH), 7.81 (dd, 1H, J=3.8, 1.5 Hz, aromatic), 8.00 (m, 5H, aromatic), 10.43 (s, 1H, NH). MS (CI, $CH_4$): 380(M+1).

Analysis for $C_{14}H_{12}F_3NO_4S_2$: Calculated: C, 48.12; H, 3.51; N, 7.48 Found: C, 48.11; H, 3.56; N, 7.40

4-(2-Thienylsulfonyl)benzenamine is described in H. Burton, and W. A. Davy, J. Chem. Soc. 527 (1948).

EXAMPLE 12

N-[4-[(2-Pyridylsulfonyl)phenyl)]-3,3,3-trifluoro-2-hydroxy-2-methylpropanamide To a stirred, cooled (−20° C.) solution of 3,3,3-trifluoro-2-hydroxy-2-methylpropanoic acid (0.76 g, 4.8 mmol) in N,N-dimethylacetamide (10 mL) was added thionyl chloride (0.57 g, 4.8 mmol) and the mixture stirred at −10° to −15° C. for 1 hour. 4-(2-Pyridylsulfonyl)benzenamine (0.75 g, 3.2 mmol) was added in one portion to the orange solution and the mixture stirred at room temperature overnight. The brown solution was poured into water and the aqueous solution extracted with ethyl acetate (2×25 mL). The organics were combined, dried ($MgSO_4$), filtered and the solvent distilled to yield a tan solid. Recrystallization from ethyl acetate/hexane yielded the title propanamide (0.95 g, 79%) as an off-white solid; mp 162°–163° C.

$^1$H-NMR (250 MHz, $d_6$-DMSO): 1.58 (s, 3H, $CH_3$), 7.59 (s, 1H, OH), 7.67 (m, 1H, aromatic), 7.92 (d, 2H, J=8.9 Hz, aromatic), 8.02 (d, 2H, J=8.9 Hz, aromatic), 8.15 (m, 2H, aromatic), 8.67 (d, 1H, J=4.2 Hz, aromatic), 10.44 (s, 1H, NH). MS (CI, $CH_4$): 375(M+1).

Analysis for $C_{15}H_{13}F_3N_2O_4S$ : Calculated: C, 48.12; H, 3.51; N, 7.48 Found: C, 48.31; H, 3.62; N, 7.36

The starting 4-(2-pyridylsulfonyl)benzamine is obtained as follows:

a. 4-(2-Pyridylsulfonyl)benzenamine

A stirred solution of 4-nitrophenyl 2-pyridyl sulfone (6.50 g, 24.6 mmol) and stannous chloride dihydrate (27.72 g, 123.0 mmol) in absolute ethanol (200 mL) was heated at reflux for 25 min. The reaction mixture was poured into ice water, and the aqueous solution basified with sodium bicarbonate (pH=8–9) and extracted with ethyl acetate (2×400 mL). The organics were combined, dried ($MgSO_4$), filtered, and the solvent distilled to yield the title benzenamine (5.12 g, 89%) as a white solid; mp 158°–160° C. $^1$H-NMR (300 MHz, $d_6$-DMSO): 6.27 (broad s, 2H, $NH_2$), 6.66 (d, 2H, J=8.7 Hz, aromatic), 7.61 (m, 3H, aromatic), 8.08 (d, 2H, J=4.9 Hz, aromatic), 8.68 (d, 1H, J=4.9, aromatic). MS (CI, $CH_4$): 235(M+1).

Analysis for $C_{11}H_{10}N_2O_2S$: Calculated: C, 56.40; H, 4.30; N, 11.96 Found: C, 56.38; H, 4.43; N, 11.91

4-Nitrophenyl 2-pyridyl sulfone is described in G. C. Pappalardo and A. Scarlata, Farmaco Ed. Science, 33(12), 945 (1978).

EXAMPLE 13

N-[(3-Chloro-(4-phenylsulfonyl)phenyl)]-3,3,3-trifluoro-2-hydroxy-2-methyl propanamide To a stirred, cooled (−20° C.) solution of 3,3,3-trifluoro-2-hydroxy-2-methylpropanoic acid (0.66 g, 4.2 mmol) in N,N-dimethylacetamide (10 mL) was added thionyl chloride (0.50 g, 4.2 mmol) and the mixture stirred at −10° to −15° C. for 1 hour. 3-Chloro-4-phenylsulfonylbenzenamine (0.75 g, 2.8 mmol) was added in one portion to the orange solution and the mixture stirred at room temperature overnight. The brown solution was poured into water and the aqueous solution extracted with ethyl acetate (2×50 mL). The organics were combined, washed with water, dried (MgSO$_4$), filtered and the solvent distilled to yield a tan foam. Flash chromatography of the solid (eluted with 10% v/v ethyl acetate in methylene chloride) and evaporation of the eluent yielded the title propanamide (1.07 g, 94%) as an off-white solid; mp 141°–143° C. $^1$H-NMR (250 MHz, d$_6$-DMSO): 1.58 (s, 3H, CH$_3$), 7.68 (m, 4H, aromatic, OH), 7.89 (d, 1H, J=6.5 Hz, aromatic), 8.11 (d, 2H, J=8.2 Hz, aromatic), 8.26 (d, 2H, J=8.4 Hz, aromatic), 10.60 (s, 1H, NH). MS (CI, CH$_4$): 408(M+1).

Analysis for C$_{16}$H$_{13}$C$_1$F$_3$NO$_4$S: Calculated: C, 47.13; H, 3.22; N, 3.43 Found: C, 46.72; H, 3.32; N, 3.34

The starting 3-chloro-4-phenylsulfonylbenzenamine is described in U.S. Pat. No. 3,576,872.

EXAMPLE 14

N-[4-(2-Chlorophenylsulfonyl)phenyl]-3,3,3-trifluoro-2-hydroxy-2-methyl propanamide To a stirred, cooled (−20° C.) solution of 3,3,3-trifluoro-2-hydroxy-2-methylpropanoic acid (0.89 g, 5.6 mmol) in N,N-dimethylacetamide (10 mL) was added thionyl chloride (0.67 g, 5.6 mmol) and the mixture stirred at −10° to −15° C. for 1 hour. 4-(2-Chlorophenylsulfonyl)benzenamine (1.00 g, 3.7 mmol) was added in one portion to the orange solution and the mixture stirred at room temperature overnight. The brown solution was poured into water and the aqueous solution extracted with ethyl acetate (2×50 mL). The organics were combined, washed with water, dried (MgSO$_4$), filtered and the solvent distilled to yield a tan solid. Recrystallization from methylene chloride/hexane yielded the title propanamide (1.43 g, 94%) as an off-white solid; mp 136°–138° C. $^1$H-NMR (250 MHz, d$_6$-DMSO): 1.58 (s, 3H, CH$_3$), 7.57 (s, 1H, OH), 7.67 (m, 3H, aromatic), 7.88 (d, 2H, J=8.8 Hz, aromatic), 8.02 (d, 2H, J=8.8 Hz, aromatic), 8.26 (d, 1H, J=6.6 Hz, aromatic). 10.46 (s, 1H, NH). MS (CI, CH$_4$): 408(M+1).

Analysis for C$_{16}$H$_{13}$C$_1$F$_3$NO$_4$S: Calculated: C, 47.13; H, 3.22; N, 3.43 Found: C, 46.93; H, 3.17; N, 3.40

4-(2-Chlorophenylsulfonyl)benzenamine is described in H. Gilman and H. Smith Broadbent, J. Amer. Chem. Soc, 69, 2053 (1947).

EXAMPLE 15

N-(4-Cyano-3-phenylsulfonylphenyl)-3,3,3,-trifluoro-2-hydroxy-2-methyl propanamide To a stirred solution of 1.50 g (4.1 mmol) of N-(4-Cyano-3-phenylthiophenyl)-3,3,3,-trifluoro-2-hydroxy-2-methyl propanamide (1,50 g, 4.1 mmol) and 120 mL of glacial acetic acid was added a solution of potassium permanganate (0.78 g, 4.9 mmol) and 78 mL of water in one portion. The mixture was stirred at ambient temperature for 45 minutes, poured into 300 mL of water, clarified with a little solid sodium bisulfite and extracted with three 275 mL portions of chloroform. The extracts were dried (MgSO$_4$), filtered and the solvent removed to yield a white solid which was recrystallized from ethyl acetate/hexane to yield, after drying at 100° C./0.1 mm, 1.38g (85%) of the title propanamide as a white solid; mp 185°–187° C. $^1$H-NMR (250 MHz, d$_6$-DMSO): 1.62 (s, 3H, CH$_3$), 7.67–7.79 (m, 4H, aromatic), 7.97–8.01 (m, 2H, aromatic, OH), 8.07 (d, 1H, J=8.6 Hz, aromatic), 8.26 (dd 1H, J=8.5, 2.0 Hz, aromatic), 8.90 (d, 1H, J=2.1 Hz), 10.90 (s, 1H, NH). MS (CI, CH$_4$): 399(M+1).

Analysis for C$_{17}$H$_{13}$F$_3$N$_2$O$_4$S: Calculated: C, 51.26; H, 3.29; N, 7.03 Found: C, 51.52; H, 3.28; N, 6.96

The starting N-(4-cyano-3-phenylthiophenyl)]-3,3,3,-trifluoro-2-hydroxy-2-methylpropanamide was prepared as follows:

a. N-(4-Cyano-3-phenylthiophenyl)-3,3,3,-trifluoro-2-hydroxy-2-methyl propanamide To a stirred, cooled (−20° C.) solution of 3,3,3-trifluoro-2-hydroxy-2-methylpropanoic acid (1.62 g 10.2 mmol) in N,N-dimethylacetamide (15 mL) was rapidly added thionyl chloride (1.30 g, 10.9 mmol) and the mixture (a precipitate formed after a few minutes) stirred at −20° C. to −5° C. for 1 hour. 4-Cyano-3-phenylthiobenzenamine (1.55 g, 6.85 mmol) was then added in one portion and the mixture allowed to stir at room temperature overnight. The solution was poured into water, extracted with ethyl ether (2×100 mL); the ethereal extracts dried (MgSO$_4$), filtered and the solvent removed in vacuo. The residue was chromatographed on 315 g of silica gel using a ethyl ether (0%, 10%, and 20%) in methylene chloride gradient. The proper fractions were combined, the solvent removed in vacuo and the residue dissolved in a mixture of 100 mL hexane and 150 mL methylene chloride. Most of the methylene chloride was distilled off as the solution was scratched to induce crystal growth. After cooling the solid was collected and dried at 85° C./0.1 mm to yield the title propanamide (2.38 g, 91%); mp 111°–113° C.

$^1$H-NMR (250 MHz, CDCl$_3$): 1.67 (s, 3H, CH$_3$), 3.68 (s, 1H, OH), 7.27 (d, 1H, J=1.9 Hz, aromatic), 7.40–7.51 (m, 5H, aromatic), 7.59–7.69 (m, 2H, aromatic), 8.51 (s, 1H, NH). MS (CI, CH$_4$): 367(M+1).

Analysis for C$_{17}$H$_{13}$F$_3$N$_2$O$_2$S: Calculated: C, 55.73; H, 3.58; N, 7.65 Found: C, 55.27; H, 3.69; N, 7.51 b. 4-Cyano-3-phenylthiobenzenamine

3-Chloro-4-cyanobenzenamine (20.0 g, 13.1 mmol) was added to a N,N-dimethylformamide (115 mL) solution of thiophenol potassium salt [prepared by adding thiophenol (13.5 mL, 13.1 mmol) to a solution of potassium hydroxide (7.35 g, 13.1 mmol) in methanol followed by removal of the methanol in vacuo] and washed in with an additional 15 ml of N,N-dimethylformamide. After stirring at 140° C. for 16 hours the mixture was poured into water, extracted with ethyl ether (3×150 mL) and the solvent removed in vacuo to yield a red oil. The oil was chromatographed on silica gel using methylene chloride as eluent. The fractions containing product (TLC- silica gel, 2% methanol/chloroform) were combined, the solvent removed and the material rechromatographed using 2:1 methylene chloride/hexane as eluent. The proper fractions were combined, concentrated to a low volume, treated with hexane and cooled (dry ice) and scratched as crystals formed. The white solid weighed 8.29 g (30%); mp 69°–71° C.

$^1$H-NMR (250 MHz, CDCl$_3$): 4.07 (s, 2H, NH$_2$), 6.29 (d, 1H, J=2.2 Hz, aromatic), 6.46 (dd 1H, J=8.3, 2.2 Hz, aromatic), 7.36–7.50 (m, 6H, aromatic). MS (CI, CH$_4$): 227(M+1).

Analysis for C$_{13}$H$_{10}$N$_2$S: Calculated: C, 69.00; H, 4.45; N, 12.38 Found: C, 69.05; H, 4.59; N, 12.39

EXAMPLE 16

N-[4-[(2-Thiazolylsulfonyl)phenyl]]-3,3,3-trifluoro-2-hydroxy-2-methyl propanamide To a stirred, cooled (−20° C.) solution of 3,3,3-trifluoro-2-hydroxy-2-methylpropanoic acid (1.12 g, 7.1 mmol) in N,N-dimethylacetamide (10 mL) was added thionyl chloride (0.85 g, 7.1 mmol) and the mixture stirred at −10° to −15°

C. for 1 hour. 2-[(4-Aminophenyl)sulfonyl]thiazole (1.14 g, 4.7 mmol) was added in one portion and the reaction mixture stirred at room temperature overnight. The reaction mixture was poured into water and the resulting tan solid was filtered and recrystallized from methylene chloride/hexane to yield the title propanamide (1.13 g, 63%) as a white solid; mp 161°–163° C. $^1$H-NMR (300 MHz, $d_6$-DMSO): 1.57 (s, 3H, CH$_3$), 7.58 (s, 1H, OH), 7.98 (d, 2H, J=8.8 Hz, aromatic), 8.06 (d, 2H, J=8.8 Hz, aromatic), 8.08 (d, 1H, J=3.3 Hz, aromatic), 8.25 (d, 1H, J=3.2 Hz, aromatic), 10.51 (s, 1H, NH). MS (CI, CH$_4$): 381(M+1).

Analysis for $C_{13}H_{11}F_3N_2O_4S_2$: Calculated: C, 41.04; H, 2.92; N, 7.37 Found: C, 40.96; H, 2.93; N, 7.36

The starting 2-[(4-aminophenyl)sulfonyl]thiazole was obtained as follows:

a. 2-[(4-Aminophenyl)sulfonyl]thiazole

A stirred solution of 2-[(4-nitrophenyl)sulfonyl]thiazole (1.50 g, 5.6 mmol) and stannous chloride dihydrate (6.26 g, 27.7 mmol) in absolute ethanol (25 mL) was heated at reflux for 1 hour. The reaction mixture was poured into ice water, and the aqueous solution basified with 15% NaOH and extracted with ethyl acetate (2×200 mL). The combined organic portions were dried (MgSO$_4$), filtered, and the solvent removed to yield a solid which on trituration with diethyl ether and filtration yielded the title thiazole (1.21 g, 89%) as a pale yellow solid, mp 148°–150° C. $^1$H-NMR (250 MHz, $d_6$-DMSO): 6.44 (br s, 2H, NH$_2$), 6.66 (d, 2H, J=8.8 Hz, aromatic), 7.61 (d, 2H, J=8.7 Hz, aromatic), 8.03 (d, 1H, J=3.2 Hz, aromatic), 8.14 (d, 1H, J=3.2 Hz, aromatic). MS (CI, CH$_4$): 241(M+1).

Analysis for $C_9H_8N_2O_2S_2$ 0.25 H$_2$O: Calculated: C, 44.14; H, 3.30; N, 11.44 Found: C, 44.37; H, 3.35; N, 11.44 b. 2-[(4-Nitrophenyl)sulfonyl]thiazole

To a stirred solution of 2-4-nitrophenylthio)thiazole (7.20 g, 30.2 mmol) in glacial acetic acid (200 mL) was added a solution of potassium permanganate (5.73 g, 36.0 mmol) in distilled water (90 mL). The dark brown mixture was stirred at room temperature for 2 hours, then treated with solid sodium sulfite to destroy excess permanganate. The mixture was diluted with water and filtered to yield a tan solid. Recrystallization from absolute ethanol yielded the title thiazole (1.63 g, 20%) as a cream colored solid; mp 159°–161° C. $^1$H-NMR (250 MHz, $d_6$-DMSO): 6.66 (d, 2H, J=8.8 Hz, aromatic), 7.61 (d, 2H, J=8.7 Hz, aromatic), 8.03 (d, 1H, J=3.2 Hz, aromatic), 8.14 (d, 1H, J=3.2 Hz, aromatic). MS (CI, CH$_4$): 271(M+1).

Analysis for $C_9H_6N_2O_4S_2$: Calculated: C, 40.00; H, 2.24; N, 10.37 Found: C, 39.94; H, 2.27; N, 10.37

The starting 2-4-nitrophenylthiothiazole is described in M. Bosco, V. Liturri, L. Troisi, L. Foriani, and P. E. Todesco, J. Chem. Soc. Perkin Trans. II, 508 (1974).

EXAMPLE 17

N-[4-[(5-Thiazolylsulfonyl)phenyl]]-3,3,3-trifluoro-2-hydroxy-2-methyl propanamide To a stirred, cooled (−20° C.) solution of 3,3,3-trifluoro-2-hydroxy-2-methylpropanoic acid (1.03 g, 6.5 mmol) in N,N-dimethylacetamide (10 mL) was added thionyl chloride (0.77 g, 6.5 mmol) and the mixture stirred at −10° to −15° C. for 1 hour. 5-[(4-Aminophenyl)sulfonyl]thiazole (1.04 g, 4.3 mmol) was added in one portion and the reaction mixture stirred at room temperature overnight. The reaction mixture was poured into water and filtered through a pad of Celite. The Celite was washed with methylene chloride (2×50 mL) and the combined organic portions were dried over MgSO$_4$, filtered, and the solvent removed in vacuo to yield a tan solid. Recrystallization from ethyl acetate/hexane yielded the title propanamide (1.21 g, 74%) as a white solid; mp 191°–193° C. $^1$H-NMR (300 MHz, $d_6$-DMSO): 1.58 (s, 3H, CH$_3$), 7.59 (s, 1H, OH), 7.99 (d, 2H, J=7.5 Hz, aromatic), 8.06 (d, 2H, J=7.5 Hz, aromatic), 8.57 (s, 1H, aromatic), 9.47 (s, 1H, aromatic), 10.49 (s, 1H, NH). MS (CI, CH$_4$): 381(M+1).

Analysis for $C_{13}H_{11}F_3N_2O_4S_2$: Calculated: C, 41.05; H, 2.91; N, 7.37 Found: C, 41.05; H, 2.93; N, 7.36

The starting 5-[(4-aminophenyl)sulfonyl]thiazole was obtained as follows:

a. 5-[(4-Aminophenyl)sulfonyl]thiazole

A stirred solution of 5-[(4-nitrophenyl)sulfonyl]thiazole (1.72 g, 6.4 mmol) and stannous chloride dihydrate (7.17 g, 31.8 mmol) in absolute ethanol (25 mL) was heated at reflux for 1 hour. The reaction mixture was poured into ice water, the aqueous solution basified with solid sodium bicarbonate and extracted with ethyl acetate (2×200 mL). The combined organic portions were dried (MgSO$_4$), filtered, and the solvent removed to yield an orange solid. Flash chromatography (eluted with 10% ethyl acetate in methylene chloride) and evaporation of the solvent yielded the title thiazole (1.20 g, 78%) as a pale yellow solid; mp 158°–160° C. $^1$H-NMR (250 MHz, $d_6$-DMSO): 6.35 (br s, 2H, NH$_2$), 6.65 (d, 2H, J=8.9 Hz, aromatic), 7.61 (d, 2H, J=8.7 Hz, aromatic), 8.39 (s, 1H, aromatic), 9.38 (s, 1H, aromatic). MS (CI, CH$_4$): 241(M+1).

Analysis for $C_9H_6N_2O_2S_2$: Calculated: C, 44.99; H, 3.36; N, 11.66 Found: C, 44.94; H, 3.38; N, 11.68 b. 5-[(4-Nitrophenyl)sulfonyl]thiazole

To a cooled (−5° C.), stirred solution of 2-amino-5-[(4-nitrophenyl)sulfonyl]thiazole (5.15 g, 18.1 mmol) in 85% phosphoric acid (200 mL) was added dropwise a solution of sodium nitrite (1.56 g, 22.6 mmol) in distilled water (10 mL) at such a rate to maintain the internal temperature between −5° and 5° C. When the addition was complete the reaction mixture was stirred for 1 hour at 0° C. then treated dropwise with 50% hypophosphoric acid (15 mL). After the addition, the ice bath was removed and reaction mixture stirred at room temperature for 3 hours during which time moderate frothing occurred. The brown solution was diluted with water (total volume=1 L), neutralized with 28% ammonium hydroxide and filtered. Flash chromatography of the resulting brown solid (eluted with 5% v/v ethyl acetate in methylene chloride) yielded the title thiazole (1.72 g, 35%) as a yellow solid; mp 168°–170° C. $^1$H-NMR (250 MHz, $d_6$-DMSO): 8.32 (d, 2H, J=12.6 Hz, aromatic), 8.45 (d, 2H, J=12.8 Hz, aromatic), 8.74 (s, 1H, aromatic), 9.578 (s, 1H, aromatic). MS (CI, CH$_4$): 271(M+1).

Analysis for $C_9H_6N_2O_4S_2$: Calculated: C, 39.40; H, 2.24; N, 10.36 Found: C, 39.68; H, 2.33; N, 10.22

The starting 2-amino-5-[(4-nitrophenyl)sulfonyl]thiazole was purchased commercially.

EXAMPLE 18

N-[4-(2-Pyrazinylsulfonyl)phenyl]-3,3,3-trifluoro-2-hydroxy-2-methylpropanamide

To a stirred, cooled (−20° C.) solution of 3,3,3-trifluoro-2-hydroxy-2-methylpropanoic acid (1.01 g, 6.4 mmol) in N,N-dimethylacetamide (10 mL) was added thionyl chloride (0.76 g, 6.4 mmol) and the mixture stirred at −10° to −15° C. for 1 hour. 4-Aminophenylsulfonylpyrazine (1.00 g, 4.2 mmol) was added in one portion and the reaction mixture stirred at room temperature overnight. The reaction mixture was poured into water and the solid collected by suction filtration. Flash chromatography (eluted with 20% v/v ethyl acetate in methylene chloride) of the solid, evaporation of the eluent, and trituration with diethyl ether yielded the title propanamide (1.26 g, 81%) as an off-white solid; mp 181°–183° C. $^1$H-NMR (250 MHz, d$_6$-DMSO): 1.58 (s, 3H, CH$_3$), 7.57 (s, 1H, OH), 7.98 (d, 2H, J=8.9 Hz, aromatic), 8.06 (d, 2H, J=9.0 Hz, aromatic), 8.81 (d, 1H, J=2.2 Hz, aromatic), 8.97 (d, 1H, J=2.2 Hz, aromatic), 9.39 (s, 1H, aromatic), 10.48 (s, 1H, NH). MS (CI, CH$_4$): 376(M+1).

Analysis for C$_{14}$H$_{12}$F$_3$N$_3$O$_4$S: Calculated: C, 44.80; H, 3.22; N, 11.20 Found: C, 44.84; H, 3.29; N, 11.11

The starting 4-aminophenylsulfonylpyrazine was obtained as described:

a. 4-Aminophenylsulfonylpyrazine.

A stirred solution of 4-nitrophenylsulfonylpyrazine (2.50 g, 9.4 mmol) and stannous chloride dihydrate (10.62 g, 47.1 mmol) in absolute ethanol (30 mL) was heated at reflux for 1 hour. The reaction mixture was poured into ice water, and the aqueous solution basified with solid sodium bicarbonate and extracted with ethyl acetate (2×200 mL). The combined organic portions were dried (MgSO$_4$), filtered, and the solvent distilled to yield an off-white solid. Recrystallization from absolute ethanol yielded the title pyrazine (1.90 g, 86%) as a white solid; mp 174°–177° C. $^1$H-NMR (300 MHz, d6-DMS0): 6.37 (br s, 2H, NH$_2$), 6.65 (d, 2H, J=8.6 Hz, aromatic), 7.61 (d, 2H, J=8.6 Hz, aromatic), 8.78 (d, 1H, J=2.3 Hz, aromatic), 8.90 (d, 1H, J=2.2 Hz, aromatic), 9.27 (s, 1H, aromatic). MS (CI, CH$_4$): 236(M+1).

Analysis for C$_{10}$H$_9$N$_3$O$_2$S: Calculated: C, 51.05; H, 3.86; N, 17.86 Found: C, 51.06; H, 3.94; N, 17.76 b. 4-Nitrophenylsulfonylpyrazine

To a stirred solution of 4-nitrophenylthiopyrazine (3.00 g, 12.9 mmol) in glacial acetic acid (150 mL) was added potassium permanganate (2.44 g, 15.4 mmol) in distilled water (90 mL). The dark brown mixture was stirred at room temperature for 30 min, then treated with solid sodium sulfite to destroy excess permanganate. The mixture was diluted with water and filtered to yield the title pyrazine (2.68 g, 78%) as an off-white solid; mp 159°–161° C. $^1$H-NMR (250 MHz, d$_6$-DMSO): 8.30 (d, 2H, J=8.3 Hz, aromatic), 8.46 (d, 2H, J=8.4 Hz, aromatic), 8.85 (d, 1H, J=3.4 Hz, aromatic), 9.03 (d, 1H, J=3.4 Hz, aromatic), 9.40 (s, 1H, aromatic). MS (CI, CH$_4$): 266(M+1).

Analysis for C$_{10}$H$_7$N$_3$O$_4$S: Calculated: C, 45.28; H, 2.66; N, 15.84 Found: C, 45.26; H, 2.64; N, 15.95 c. 4-Nitrophenylthiopyrazine

A stirred solution of chloropyrazine (6.71 g, 58.6 mmol) and potassium 4-nitrothiophenolate (12.45 g, 64.4 mmol) in dimethylformamide (40 mL) was heated at 110° C. for 4 hours. The reaction mixture was poured into ice water and the brown solid that precipitated was filtered. Recrystallization from absolute ethanol yielded the title pyrazine (4.30 g, 30%) as a yellow solid; rap 88°–90° C. $^1$H-NMR (300 MHz, d$_6$-DMSO): 7.77 (d, 2H, J=6.7 Hz, aromatic), 8.24 (d, 2H, J=6.6 Hz, aromatic), 8.57 (m, 2H, aromatic), 8.72 (d, 1H, J=1.2 Hz, aromatic). MS (CI, CH$_4$): 234(M+1).

Analysis for C$_{10}$H$_7$N$_3$O$_2$S: Calculated: C, 51.50; H, 3.02; N, 18.02 Found: C, 51.50; H, 3.00; N, 17.96

EXAMPLE 19

N-[4-(2-Pyridylcarbonyl)phenyl]-3,3,3-trifluoro-2-hydroxy-2-methylpropanamide

To a stirred, cooled (–20° C.) solution of 3,3,3-trifluoro-2-hydroxy-2-methylpropanoic acid (1.20 g, 7.6 mmol) in N,N-dimethylacetamide (10 mL) was added thionyl chloride (0.90 g, 7.6 mmol) and the mixture stirred at –10° to –15° C. for 1 hour. 2-(4-Aminobenzoyl)pyridine (1.00 g, 5.0 mmol) was added in one portion and the reaction mixture stirred overnight at room temperature. The reaction mixture was poured into water and the aqueous solution extracted with ethyl acetate (2×50 mL). The combined organics were dried (MgSO$_4$), filtered and the solvent removed in vacuo to yield a brown oil. Flash chromatography (eluted with 5% v/v ethyl acetate in methylene chloride) of the oil, evaporation of the eluent, and trituration with diethyl ether yielded the title propanamide (1.07 g, 63%) as a white solid; mp 151°–154° C. $^1$H-NMR (250 MHz, d$_6$-DMSO): 1.58 (s, 3H, CH$_3$), 7.58 (s, 1H, OH), 7.98 (d, 2H, J=8.9 Hz, aromatic), 8.06 (d, 2H, J=9.0 Hz, aromatic), 8.81 (m, 2H, aromatic), 8.97 (d, 1H, J=2.2 Hz, aromatic), 9.39 (s, 1H, aromatic), 10.48 (s, 1H, NH). MS (CI, CH$_4$): 339(M+1).

Analysis for C$_{16}$H$_{13}$F$_3$N$_2$O$_3$: Calculated: C, 56.81; H, 3.87; N, 8.28 Found: C, 56.50; H, 3.91; N, 8.21

The starting 2-(4-aminobenzoyl)pyridine is described in E. Koenigs, H. Menscing and P. Kirsh, Ber., 59B, 1717 (1926).

EXAMPLE 20

N-[4-(3-Chlorophenylsulfonyl)phenyl]-3,3,3-trifluoro-2-hydroxy-2-methyl propanamide To a stirred, cooled (–20° C.) solution of 3,3,3-trifluoro-2-hydroxy-2-methylpropanoic acid (0.22 g, 1.4 mmol) in N,N-dimethylacetamide (10 mL) was added thionyl chloride (0.17 g, 1.4 mmol) and the mixture stirred at –10° to –15° C. for 1 hour. 4-Amino-3'-chlorodiphenylsulfone (0.75 g, 2.8 mmol) was added in one portion and the reaction mixture stirred at room temperature overnight. The reaction mixture was poured into water and the aqueous solution filtered through a pad of Celite. The Celite was extracted with methylene chloride (200 mL) which was dried (MgSO$_4$), filtered and the solvent removed to yield a tan solid. Flash chromatography of the solid (eluted with 5% v/v ethyl acetate in methylene chloride) and evaporation of the eluent yielded the title propanamide (0.22 g, 58%) as a white solid; mp 154°–156° C. $^1$H-NMR (250 MHz, d$_6$-DMSO): 1.58 (s, 3H, CH$_3$), 7.57 (s, 1H, OH), 7.65 (t, 1H, J=8.0 Hz, aromatic), 7.77 (d, 1H, J=7.8 Hz, aromatic), 7.91 (d, 1H, J=7.8 Hz, aromatic), 8.01 (m, 5H, aromatic), 10.60 (s, 1H, NH). MS (CI, CH$_4$): 408(M+1).

Analysis for C$_{16}$H$_{13}$C$_1$F$_3$NO$_4$S: Calculated: C, 47.13; H, 3.22; N, 3.43 Found: C, 46.81; H, 3.37; N, 3.34

The starting 4-amino-3'-chlorodiphenylsulfone was purchased commercially.

EXAMPLE 21

N-[4-[(3-Methylphenylsulfonyl)phenyl]]-3,3,3-trifluoro-2-hydroxy-2-methyl propanamide To a stirred, cooled (–20° C.) solution of 3,3,3-trifluoro-2-hydroxy-2-methylpropanoic acid (0.43 g, 2.7 mmol) in N,N-dimethylacetamide (10 mL) was added thionyl chloride (0.32 g, 2.7 mmol) and the mixture stirred at –10° to –15° C. for 1 hour. 4-[(3-Methylphenyl)sulfonyl]benzenamine (0.45 g, 1.8 mmol) was added in one portion and the reaction mixture stirred at room temperature overnight. The mixture was poured into water and the aqueous solution filtered through a pad of Celite. The Celite was washed with methylene chloride (100 mL) and the organic extract dried (MgSO$_4$), filtered and the solvent removed in vacuo to yield a tan solid which was purified by flash column chromatography (10% v/v ethyl acetate/methylene chloride). Evaporation of the solvent from the proper fractions and recrystallization of the resulting solid from methylene chloride/ hexane yielded the title propanamide (0.52 g, 74%) as a white solid; mp 164°–166° C. $^1$H-NMR (300 MHz, $d_6$-DMSO): 1.57 (s, 3H, CH$_3$), 2.38 (s, 3H, aryl CH$_3$), 7.49 (dd, 2H, J=5.1, 1.0 Hz, aromatic), 7.56 (s, 1H, OH), 7.73 (m, 2H, aromatic), 7.91 (d, 2H, J=8.9 Hz, aromatic), 8.00 (d, 2H, J=8.9 Hz, aromatic), 10.42 (s, 1H, NH). MS (CI, CH$_4$): 388(M+1).

Analysis for C$_{17}$H$_{16}$F$_3$NO$_4$S: Calculated: C, 52.71; H, 4.16; N, 3.62 Found: C, 52.71; H, 4.28; N, 3.54

The starting 4-[(3-methylphenyl)sulfonyl]benzenamine was prepared in the following manner:

a. 4-[(3-Methylphenyl)sulfonyl]benzenamine

A stirred solution of 3-methylphenyl 4-nitrophenyl sulfone (0.50 g, 1.8 mmol) and stannous chloride dihydrate (2.03 g, 9.0 mmol) in absolute ethanol (5 mL) was heated at reflux for 1 hour. The reaction mixture was poured into ice water and the aqueous solution basified with 15% NaOH and extracted with ethyl acetate (2×100 mL). The combined organic extracts were dried (MgSO$_4$), filtered, and the solvent removed in vacuo to yield an off-white solid. Recrystallization from absolute ethanol/hexane yielded the title benzenamine (0.45 g, 100%) as a white solid; mp 183°–185° C. $^1$H-NMR (300 MHz, $d_6$-DMSO): 2.36 (s, 3H, CH$_3$), 6.17 (s, 2H, NH$_2$), 6.61 (dd, 2H, J=7.0, 1.8 Hz, aromatic), 7.43 (d, 2H, J=7.1Hz, aromatic), 7.54 (d, 2H, J=8.7 Hz, aromatic), 7.63 (m, 2H, aromatic). MS (CI, CH$_4$): 248(M+1).

Analysis for C$_{13}$H$_{13}$NO$_2$S: Calculated: C, 63.14; H, 5.30; N, 5.66 Found: C, 63.13; H, 5.28; N, 5.64

The starting 3-methylphenyl 4-nitrophenyl sulfone was purchased commercially.

EXAMPLE 22

N-[(4-Phenylcarbonyl)phenyl]-3,3,3-trifluoro-2-hydroxy-2-methylpropanamide.

To a stirred, cooled (–20° C.) solution of 3,3,3-trifluoro-2-hydroxy-2-methylpropanoic acid (10.54 g, 66 mmol) in N,N-dimethylacetamide (100 mL) was added thionyl chloride (7.94 g, 66 mmol) and the mixture stirred at –10° to –15° C. for 1 hour. 4-Aminobenzophenone (8.67 g, 44 mmol) was added in one portion and the reaction mixture stirred at room temperature overnight. The mixture was poured into water and the white solid that precipitated upon stirring was filtered from solution, dried on the filter for 1 hour, and recrystallized from ethyl acetate/hexane (1:2 v/v). The first crop yielded the title propanamide (9.51 g, 64z) as a white solid; mp 151°–153° C. A second crop was filtered upon cooling of the filtrate for 72 hours to yield an additional 3.21 g (22%) of a white solid which was identical to the first crop by melting point and spectral properties. $^1$H-NMR (300 MHz, $d_6$-DMSO): 1.61 (s, 3H, CH$_3$), 7.54–7.59 (m, 3H, aromatic and OH), 7.65–7.71 (m, 3H, aromatic), 7.75 (d, 2H, J=8.5 Hz, aromatic), 7.98 (d, 2H, J=8.5 Hz, aromatic), 10.35 (s, 1H, NH). MS (CI, CH$_4$): 338(M+1).

Analysis for C$_{17}$H$_{14}$F$_3$NO$_3$: Calculated: C, 60.54; H, 4.23; N, 4.15 Found: C, 60.33; H, 4.23; N, 4.12

The starting 4-aminobenzophenone was purchased commercially.

EXAMPLE 23

N-[4-[(3-Pyridylcarbonyl)phenyl]]-3,3,3-trifluoro-2-hydroxy-2-methylpropanamide.

To a stirred, cooled (–20° C.) solution of 3,3,3-trifluoro-2-hydroxy-2-methylpropanoic acid (0.63 g, 4.0 mmol) in N,N-dimethylacetamide (7 mL) was added thionyl chloride (0.48 g, 4.0 mmol) and the mixture stirred at –10° to –15° C. for 1 hour. 3-(4-Aminobenzoyl)pyridine (0.66 g, 3.3 mmol) was added in one portion and the reaction mixture stirred at room temperature overnight. The mixture was poured into water and the aqueous solution extracted with ethyl ether (2×100 mL). The combined organic extracts were dried (MgSO$_4$), filtered, and the solvent removed in vacuo to yield a pale yellow solid. Recrystallization from absolute ethanol/hexane yielded the title propanamide (0.42 g, 37%) as a white solid; mp 206°–208° C.

$^1$H-NMR (300 MHz, $d_6$-DMSO): 1.60 (s, 3H, CH$_3$), 7.57 (s, 1H, OH), 7.58°–7.62 (m, 1H, aromatic), 7.79 (dd, 2H, J=7.0, 1.7 Hz, aromatic), 7.98 (dd, 2H, J=7.0, 1.7 Hz, aromatic), 8.08°–8.12 (m, 1H, aromatic), 8.83 (dd, 1H, J=4.8, 1.7 Hz, aromatic), 8.87 (d, 1H, J=1.7 Hz, aromatic), 10.38 (s, 1H, NH). MS (CI, CH$_4$): 339(M+1).

Analysis for C$_{16}$H$_{13}$F$_3$N$_2$O$_3$: Calculated: C, 56.81; H, 3.87; N, 8.28 Found: C, 56.60; H, 3.881N, 8.23

The starting 3-(4-aminobenzoyl)pyridine was obtained as follows:

a. 3-(4-Aminobenzoyl)pyridine

A stirred solution of 3-(4-nitrobenzoyl)pyridine (1.08 g, 4.7 mmol) and stannous chloride dihydrate (5.34 g, 23.7 mmol) in absolute ethanol (50 mL) was heated at reflux for 1 hour. The reaction mixture was poured into ice water and the aqueous solution basified with solid sodium bicarbonate and extracted with ethyl acetate (2×150 mL). The combined organic extracts were dried (MgSO$_4$), filtered, and the solvent removed in vacuo to yield a yellow solid. Purification of the solid by flash chromatography (ethyl ether) and evaporation of the eluent yielded the title pyridine (0.71 g, 76%) as a yellow solid; mp 103°–105° C. $^1$H-NMR (300 MHz, $d_6$-DMSO): 6.31 (s, 2H, N J2), 6.64 (d, 2H, J=8.6 Hz, aromatic), 7.52–7.58 (m, 3H, aromatic), 7.97–8.01 (m, 1H, aromatic), 8.74–8.77 (m, 2H, aromatic). MS (CI, CH$_4$): 199(M+1).

The starting 3-(4-nitrobenzoyl)pyridine is described in F. Bryans, and F. L. Pyman, J. Chem. Soc., 549 (1929).

EXAMPLE 24

N-[4-(Phenylsulfonyl)phenyl]-1-hydroxycyclopropylcarboxamide

A solution of 1-hydroxycyclopropanecaboxylic acid (0.66 g, 6.44 mmol) in dry dimethylacetamide (10 ml) was stirred under a nitrogen atmosphere at –15° C. Thionyl chloride (0.77 g, 6.44 mmol) was added and the resulting mixture was allowed to stir at –15° C. for 1 hour. 4-Phenylsulfonylaniline (1.0 g, 4.29 mmol) was then added and the reaction mixture was stirred at –15° C. for a further 15 mins. The solution was then allowed to warm to room temperature where it was stirred overnight. The reaction mixture was poured onto ice, extracted with ethyl acetate, and the combined ethyl acetate portions were washed with 1M HCl After drying (MgSO$_4$) the ethyl acetate was removed by evaporation to give a buff-colored solid. Crystallization of this material from ethyl acetate/hexane yielded the title tertiary carbinol, (0.82 g, 60%) as a white solid; mp=214.5°–216° C. $^1$H-NMR (250 MHz, $d_6$-DMSO): 0.98 (m, 2H, 2 CH$_2$), 1.15 (m, 2H, CH$_2$), 6.63 (s, 1H, OH), 7.65 (m, 3H, ArH), 7.95 (m, 6H, ArH), 10.29 (s, 1H, NH). MS (CI, CH$_4$): 318(M+1, 100).

Analysis for C$_{16}$H$_{15}$NO$_4$S: Calculated: C, 60.55; H, 4.76; N, 4.41 Found: C, 60.51; H, 4.77; N, 4.40

EXAMPLE 25

N-[4-(Phenylsulfonyl)phenyl]-2-hydroxy-2-ethylbutanamide

A solution of 2-ethyl-2-hydroxybutyric acid (1.14 g, 8.69 mmol) in dry dimethylacetamide was stirred under a nitrogen atmosphere at −15° C. Thionyl chloride (1.03 g, 8.69 mmol) was added and the resulting mixture was allowed to stir at −15° C. for 1 hour. 4-Phenylsulfonylaniline (1.34 g, 5.74 mmol) was then added and the reaction mixture was stirred at −15° C. for a further 15 mins. The solution was then allowed to warm to room temperature where it was stirred for 48 hours. The reaction mixture was poured onto ice, extracted with ethyl acetate, basified to pH 12 and extracted further with ether. The combined ether portions were dried over $MgSO_4$ and evaporated to give a gold-colored oil. Crystallization of this material from Et2O/hexane yielded an impure solid. Flash chromatography of this material on silica gel eluting with methylene chloride provided the title tertiary carbinol(0.16 g, 8%) as a white solid; mp=116°–119° C. $^1$H-NMR (250 MHz, $d_6$-DMSO): 0.80 (t, 6H, 2 $CH_3$), 1.54 (m, 2H, $CH_2$) 1.73 (m, 2H, $CH_2$), 5.37 (s, 1H, OH), 7.64 (m, 3H, ArH), 7.94(m, 6H, ArH), 9.89 (s, 1H, NH). MS (CI, $CH_4$): 348(M+1, 100).

Analysis for $C_{18}H_{21}NO_4S \cdot 0.25\ H_2O$: Calculated: C, 61.43; H, 6.16; N, 3.98 Found: C, 61.57; H, 6.02; N, 4.09

EXAMPLE 26

N-[4-(Phenylsulfonyl)phenyl]-2-hydroxy-2-methylbutanamide

A solution of 2-hydroxy-2-methyl butyric acid (0.76 g, 6.4 mmol) in dry dimethylacetamide (15 ml) was stirred under a nitrogen atmosphere at −10° C. Thionyl chloride (0.76 g, 6.4 mmol) was added and the resulting mixture was allowed to stir at −10° C. for 1 hour. 4-Phenylsulfonyl aniline (1.0 g, 4.29 mmol) was then added and the reaction mixture was stirred at −10° C. for a further 15 mins. The solution was then allowed to warm to room temperature where it was stirred overnight. The reaction mixture was poured onto water, extracted with ethyl acetate, and the combined ethyl acetate portions were washed with water, and brine. After drying ($Na_2SO_4$) the ethyl acetate was removed by evaporation. Crystallization from ethyl acetate/hexane yielded the title tertiary carbinol (0.89 g, 62.5%) as a colorless crystalline solid; mp=163.0°–165.0° C. $^1$H-NMR (250 MHz, $d_6$-DMSO): 0.82 (t, J=7Hz, 3H, $CH_3$), 1.32 (s, 3H, $CH_3$), 1.56 (m, J=7Hz, 1H, CH ), 1.76 (m, J=7Hz, 1H, $CH_2$), 5.65 (s, 1H, OH), 7.64 (m, 3H, ArH), 7.91 (m, 4H, ArH, 8.01 (d, J=11.1Hz, 2H, ArH), 9.98 (s, 1H, NH). MS (CI, $CH_4$): 334(M+1, 100).

Analysis for $C_{17}H_{19}NO_4S$: Calculated: C, 61.24; H, 5.74; N, 4.20 Found: C, 61.15; H, 5.60; N, 4.52

EXAMPLE 27

N-[4-(phenylsulfonyl)phenyl]-1-hydroxy-cyclopentanecarboxamide

A solution of 1-hydroxycyclopentanecarboxylic acid (0.76 g, 6.4 mmol) in dry dimethylacetamide (15 ml) was stirred under a nitrogen atmosphere at −10° C. Thionyl chloride (0.76 g, 6.4 mmol) was added and the resulting mixture was allowed to stir at −10° C. for 1 hour. 4-Phenylsulfonylaniline (1.0 g, 4.29 mmol) was then added and the reaction mixture was stirred at −10° C. for a further 15 mins. The solution was then allowed to warm to room temperature where it was stirred overnight. The reaction mixture was poured onto water, extracted with ethyl acetate, and the combined ethyl acetate portions were washed with water, and brine. After drying ($Na_2SO_4$) the ethyl acetate was removed by evaporation. Crystallization from ethyl acetate/hexane yielded the title tertiary carbinol (0.70 g, 47%) as a white solid; mp=214.0°–216.0° C. $^1$H-NMR (300 MHz, $d_6$-DMSO): 1.73 (m, 6H, $CH_2$), 1.97 (m, 2H, $CH_2$), 5.67 (s, 1H, OH), 7.64 (m, 3H, ArH), 7.94 (m, 6H, ArH), 10.13 (s, 1H, NH). MS (CI, $CH_4$): 346(M+1, 100).

Analysis for $C_{18}H_{19}NO_4S$: Calculated: C, 62.59; H, 5.54; N, 4.06 Found: C, 62.67; H, 5.58; N, 4.00

EXAMPLE 28

N-[4-(Phenylsulfonyl)phenyl]-3-fluoro-2-hydroxy-2-methylpropanamide.

A solution of 2-hydroxy-2-fluoromethylpropionic acid (0.78 g, 6.4 mmol) in dry dimethylacetamide (15 ml) was stirred under a nitrogen atmosphere at −10° C. Thionyl chloride (0.76 g, 6.4 mmol) was added and he resulting mixture was allowed to stir at −10° C. for 1 hour. 4-Phenylsulfonylaniline (1.0 g, 4.29 mmol) was then added and the reaction mixture was stirred at −10° C. for a further 15 mins. The solution was then allowed to warm to room temperature where it was stirred overnight. The reaction mixture was poured onto water, extracted with ethyl acetate, and the combined ethyl acetate portions were washed with water, and brine. After drying ($Na_2SO_4$) the ethyl acetate was removed by evaporation to give an amber foam. Trituration with ether/methylene chloride yielded the title tertiary carbinol (0.75 g, 52%) as a light tan solid; mp=189°–192° C. $^1$H-NMR (300 MHz, $d_6$-DMSO): 1.31 (s, 3H, $CH_3$), 4.38 (dd, J=72 and 9.4 Hz, 1H, $CH_2F$), 4.58 (dd, J=72 and 9.3 Hz, 1H, $CH_2F$), 6.29 (s, 1H, OH), 7.58–7.68 (m, 4H, ArH), 7.89–8.02 (m, 5H, ArH), 10.16 (S, 1H, NH). MS (CI, $CH_4$): 338(M+1, 100).

Analysis for $C_{16}H_{16}FNO_4S \cdot 0.1\ H_2O$: Calculated: C, 56.66; H, 4.81; N, 4.13 Found: C, 56.40; H, 4.74; N, 4.02

EXAMPLE 29

N-[4-(4-Pyridylsulfonyl)phenyl]-3-fluoro-2-hydroxy-2-methylpropanamide.

A solution of 2-hydroxy-2-fluoromethylpropionic acid (0.53 g, 4.33 mmol) in dry dimethylacetamide (12 ml) was stirred under a nitrogen atmosphere at −10° C. Thionyl chloride (0.52 g, 4.33 mmol) was added and the resulting mixture was allowed to stir at −10° C. for 1 hour. 4-Phenylsulfonylaniline (0.68 g, 2.89 mmol) was then added and the reaction mixture was stirred at −10° C. for a further 15 mins. The solution was then allowed to warm to room temperature where it was stirred overnight. The reaction mixture was poured onto water and the pH adjusted to pH 8.0 with sodium bicarbonate solution. The aqueous solution was extracted with ethyl acetate, and the combined ethyl acetate portions were washed with water, and brine. After drying ($Na_2SO_4$) the ethyl acetate was removed by evaporation to give a yellow-orange solid. The solid was washed with ether/methylene chloride to yield the title tertiary carbinol (0.32 g, 32%) as a pale yellow solid; mp=209°–211° C. $^1$H-NMR (300 MHz, $d_6$-DMSO): 1.31 (s, 3H, $CH_3$), 4.38 (dd. J=72 and 9.4 Hz, 1H, $CH_2F$), 4.58 (dd, J=72 and 9.3 Hz, 1H, $CH_2F$), 6.31 (s, 1H, OH), 7.87 (d, J=6 Hz, 2H, PyH), 7.96 (d, J=8.9 Hz, 2H, PhH), 8.06 (d, J=8.9 Hz, 2H, PhH), 8.86 (d, J=6 Hz, 2H, PyH), 10.22 (s, 1H, NH). MS (CI, $CH_4$): 339(M+1, 100).

Analysis for $C_{15}H_{15}FN_2O_4S$: Calculated: C, 53.25; H, 4.47; N, 8.28 Found: C, 52.85; H, 4.50; N, 8.05

EXAMPLE 30

N-[4-(Phenylcarbonyl)phenyl]-3-fluoro-2-hydroxy-2-methylpropanamide

A solution of 2-hydroxy-2-fluoromethylpropionic acid (0.93 g, 7.65 mmol) in dry dimethylacetamide (20 ml) was stirred under a nitrogen atmosphere at −10° C. Thionyl chloride (0.91 g, 7.65 mmol) was added and the resulting mixture was allowed to stir at −10° C. for 1 hour. 4-Phenylsulfonylaniline (1.0 g, 4.29 mmol) was then added and the reaction mixture was stirred at −10° C. for a further 15 mins. The solution was then allowed to warm to room temperature where it was stirred overnight. The reaction mixture was poured onto water, extracted with ethyl acetate, and the combined ethyl acetate portions were washed with water, and brine. After drying ($Na_2SO_4$) the ethyl acetate was removed by evaporation to give an straw-colored foam. Chromatography on silica gel, eluting with ethyl acetate/hexane (1:1) gave the tertiary carbinol (0.75 g, 48%) as a white powder; mp=146°–148° C. $^1$H-NMR (300 MHz, $d_6$-DMSO): 1.36 (s, 3H, $CH_3$), 4.38 (dd, J=72 and 9.4 Hz, 1H, $CH_2F$), 4.58 (dd, J=72 and 9.3 Hz, 1H, $CH_2F$), 6.32 (s, 1H, OH), 7.56 (t, J=7.7 Hz, 2H, ArH), 7.65–7.76 (m, 5H, ArH), 7.97 (d, J=8.7 Hz, 2H, ArH), 10.08 (s, 1H, NH). MS (CI, $CH_4$): 302(M+1, 100).

Analysis for $C_{17}H_{16}FNO_3$: Calculated: C, 67.76; H, 5.35; N, 4.65 Found: C, 67.45; H, 5.41; N, 4.58

EXAMPLE 31

N-[4-(Phenylsulfonyl)phenyl]-3,3,3-trifluoro-2-hydroxy-2-trifluoromethylpropanamide A solution of 4'-phenylsulfonyl-2-benzyloxy-2,2-bis (trifluoromethyl)acetanilide (0.32 g, 0.62 mmol) in absolute ethanol (120 ml) was hydrogenated using a 10% Palladium/carbon catalyst for 3.5 hours. The mixture was filtered through Celite and the filtrate evaporated to yield an oil which crystallized on standing to give the title tertiary carbinol (89%) as a white solid; mp=94°–98° C. $^1$H-NMR (250 MHz, $d_6$-DMSO): 7.86 (m, 3H, ArH), 7.92 (m, 6H, ARM), 9.8 (brs, 1H, OH), MS (Fab(−ve ion)): 426(M-1, 100%).

Analysis for $C_{16}H_{11}F_6NO_4S$: Calculated: C, 44.97; H, 2.60; N, 3.28 Found: C, 44.60; H, 2.57; N, 3.14 a. N-[4-(Phenylsulfonyl)phenyl]-3,3,3-trifluoro-2-benzyloxy-2-trifluoromethyl-propanamide A solution of 2-benzyloxy-2,2-bis(trifluoromethyl)acetic acid (0.10 g, 0.33 mmol) in dry benzene (3 ml) was stirred under a nitrogen atmosphere. Thionyl chloride (0.18 g, 1.52 mmol) was added followed by three drops of dimethylformamide and the resulting solution was refluxed for 20 minutes. After cooling the solution was evaporated to dryness in vacuo. Benzene (10 ml) was added and the evaporation repeated to give the acid chloride as a viscous oil. The crude acid chloride was dissolved in methylene chloride (3 ml) and was cooled to 0° C. To the stirred solution was added 4-phenylsulfonylaniline (0.154 g, 0.66 mmol), triethylamine (0.067 g, 0.66 mmol) and dimethylaminopyridine (0.05 g). After stirring for 10 minutes the solution was allowed to warm to room temperature where it was stirred for a further 18 hours. The reaction mixture was then poured into water (10 ml). The organic layer was washed with 3MHCl and brine. Drying ($MgSO_4$) and evaporation furnished a gold-colored oil. Chromatography on silica gel, eluting with methylene chloride gave the title tertiary carbinol (0.10 g, 59%) as a tan solid; mp=103°–108° C.

$^1$H-NMR (250 MHz, $d_6$-DMSO): 4.97 (s, 2H, $CH_2$), 7.41 (m, 5H, ArH), 7.86 (m, 3H, ArH), 7.98 (m, 6H, ArH), 11.02 (s, 1H, NH). MS (CI, $CH_4$): 518(M+1, 50%).

Analysis for $C_{23}H_{17}F_6NO_4S$: Calculated: C, 67.76; H, 5.35; N, 4.65 Found: C, 67.45; H, 5.41; N, 4.58

EXAMPLE 32

N-[4-(Phenylsulfonyl)phenyl]-3,3,-difluoro-2-hydroxy-2-methylpropanamide

A solution of 2-hydroxy-2-difluoromethylpropionic acid (0.9 g, 6.4 mmol) in dry dimethylacetamide (15 ml) was stirred under a nitrogen atmosphere at −10° C. Thionyl chloride (0.76 g, 6.4 mmol) was added and the resulting mixture was allowed to stir at −10° C. for 1 hour. 4-Phenylsulfonylaniline (1.0 g, 4.3 mmol) was then added and the reaction mixture was stirred at −10° C. for a further 15 mins. The solution was then allowed to warm to room temperature where it was stirred overnight. The reaction mixture was poured into ammonium chloride solution and extracted with ethyl acetate. The combined ethyl acetate fractions were washed with water and brine. After drying ($Na_2SO_4$) and decolorization (Charcoal) the solution was evaporated in vacuo. A foam was obtained which was triturated with toluene and crystallized from ethyl acetate/hexane to give the title tertiary carbinol (0.72 g, 47%) as white crystals; mp=168°–169° C.

$^1$H-NMR (300 MHz, $d_6$-DMSO): 1.41 (s, 3H, CH3), 6.13 (t, J=54.9 Hz, 1H, $CHF_2$), 6.76 (s, 1H, OH), 7.58–7.68 (m, 3H, ArH), 7.89–8.01 (m, 6H, ArH), 10.27 (s, 1H, NH). MS (CI, $CH_4$): 356(M+1, 100).

Analysis for $C_{16}H_{15}F_2NO_4S$: Calculated: C, 54.08; H, 4.25; N, 3.94 Found: C, 53.75; H, 4.40; N, 3.78

EXAMPLE 33

N-[4-(Phenylcarbonyl)phenyl]-3,3,-difluoro-2-hydroxy-2-methylpropanamide

A solution of 2-hydroxy-2-difluoromethylpropionic acid (1.07 g, 7.65 mmol) in dry dimethylacetamide (15 ml) was stirred under a nitrogen atmosphere at −10° C. Thionyl chloride (0.91 g, 7.65 mmol) was added and the resulting mixture was allowed to stir at −10° C. for 1 hour. 4-Aminobenzophenone (1.0 g, 5.1 mmol) was then added and the reaction mixture was stirred at −10° C. for a further 15 mins. The solution was then allowed to warm to room temperature where it was stirred overnight. The reaction mixture was poured into hydrochloric acid solution (1M) and extracted with ethyl acetate. The combined ethyl acetate fractions were washed with water and brine. After drying ($Na_2SO_4$) and decolorization (Charcoal) the solution was evaporated in vacuo. A off-white foam was obtained which was triturated with hexane/ethyl acetate. The crude product was filtered through a short silica gel column with chloroform and crystallized from chloroform/hexane to give the title tertiary carbinol (0.89 g, 55%) as shiny, buff-colored crystals; mp=123°–124° C. $^1$H-NMR (300 MHz, $d_6$-DMSO): 1.45 (s, 3H, CH3), 6.17 (t, J=55 Hz, 1H, $CHF_2$), 6.77 (s, 1H, OH), 7.56 (t, 2H, ArH), 7.65–7.76 (m, 5H, ArH), 7.96 (d, J=8.7 Hz, 2H, ArH), 10.19 (s, 1H, NH). MS (CI, $CH_4$): 320(M+1, 100).

Analysis for $C_{17}H_{15}F2NO_3$·0.2 $H_2O$: Calculated: C, 63.23; H, 4.81; N, 4.34 Found: C, 63.21; H, 4.74; N, 4.30

EXAMPLE 34

N-[4-(Phenylcarbonyl)phenyl]-3,3,3-trifluoro-2-hydroxy-2-trifluoromethyl-propanamide.

Tetrahydrofuran (35 ml,dry) was added to a mixture of 2,2-bis-trifluoromethyl 2-hydroxyacetic acid (1.08 g,5.1 mmol) and 1,1'-carbonyldiimidazole (0.83 g,5.1 mmol), while under a nitrogen atmosphere. There was an immediate evolution of carbon dioxide. The reaction was refluxed for 0.5 hrs and cooled to 23° C. The reaction was treated with 4-aminobenzophenone (1.01 g,5.1 mmol), stirred at 23° C. for 1.5 hrs, and then at reflux 18 hrs. The reaction was evaporated to a yellow oil-solid mixture. The mixture was dissolved in ethyl ether, treated with hydrogen chloride in ethyl ether, and filtered. The filtrate was evaporated to a yellow oil-solid mixture. Chromatography of this mixture on silica gel, eluting with 5% ethylether in methylenechloride provided the title compound as an off-white solid; mp 143°–146° C. $^1$H-NMR (250 MHz,d$_6$-DMSO): 7.67(m, 2H, ArH), 7.83(m, 5H, ArH),7.96(d, J=8.8, 2H, ArH), 9.82(s, 1H, OH), 10.82(s, 1H, NH). MS(CI,CH$_4$): 392 (M+1).

Analysis for C$_{17}$H$_{11}$F$_6$NO$_3$: Calculated: C, 52.18; H, 2.83; N, 3.58 Found: C, 52.25; H, 3.10; N, 3.50

2,2-bis-trifluoromethyl-2-hydroxyacetic acid was obtained from Fairfield chemicals (custom synthesis).

EXAMPLE 35

N-[4-[4-Pyridylsulfonyl)phenyl]]-3,3-difluoro-2-hydroxy-2-difluoromethyl-propanamide To a solution of 2,2-bis-difluoromethyl-2-hydroxyacetic acid (0.5 g, 2.84 mmole) in dimethylacetamide (10 ml) at −10° C. was added thionyl chloride (0.34 g, 2.84 mmol) dropwise. The resulting solution was stirred at −10° C. for approximately 30 mins. 4-(4-Pyridylsulfonyl)aniline (0.58 g, 2.5 mmol) was added and the reaction mixture was stirred overnight at room temperature. The reaction mixture was then poured into water, and sodium bicarbonate solution was added to give a pH of 7–7.5. A salmon pink colored precipitate was formed. The solid was filtered, washed with water, and dried. Recrystallization and decolorization (charcoal) from ethyl acetate/methanol/hexane gave the title compound (0.45 g, 46%) as a straw colored solid; mp 248°–250° C. $^1$H-Nmr (300 MHz,d$_6$-DMSO): 6.45(t, J=52.6 Hz, 2H, HCF$_2$), 7.88(d, J=6.1 Hz, 2H, ArH), 8.04(m, 5H, OH and ArH), 8.86(s, J=6.1 Hz, 2H, ArH), 10.58(s, 1H, NH). MS(CI,CH$_4$): 393 (M+1).

Analysis for C$_{15}$H$_{12}$F$_4$N$_2$O$_4$S: Calculated: C, 45.92; H, 3.08; N, 7.14 Found: C, 45.80; H, 3.13; N, 7.13

The 2,2-bis-difluoromethyl-2-hydroxyacetic acid was prepared as follows:

Trimethylsilyl cyanide (13.1 g, 0.13 mole) was added dropwise to 1,1,3,3-tetrafluoroacetone (17.17 g, 0.13 mole) with stirring at a temperature of 0° C. The reaction flask was sealed and was kept at room temperature overnight. The clear reaction mixture was added dropwise to concentrated sulfuric acid (60 ml). A exotherm was observed. Water (220 mL) was then added dropwise and the resulting solution was stirred and refluxed overnight. The reaction solution was cooled to room temperature, saturated with sodium chloride and extracted with ethyl acetate (2×150 ml). The combined ethyl acetate extracts were dried (Na$_2$SO$_4$) and evaporated to give a syrup that slowly solidified to a white solid mass (12.8 g, 56%); mp 72.5°–73.5° C. $^1$H-NMR (300 MHz, d$_6$ DMSO): 6.27 (s, 1H, OH), 6.26 (t, J=57.4 Hz, 2H, HCF$_2$). MS(CI): 177 (M+1, 100%).

1,1,3,3-Tetrafluoroacetone was prepared using the procedure by W. J. Middleton and R. V. Lindsey, Jr., J. Am. Chem. Soc., 86, 4948(1964).

EXAMPLE 36

N-[3-Hydroxy-4-(phenylsulfonyl)phenyl]-3,3,3-trifluoro-2-hydroxy-2-methylpropanamide To a stirred suspension of N-[3-methoxy-4-(phenylsulfonyl)phenyl]-3,3,3-trifluoro-2-hydroxy-2-methylpropanamide (0.75 g, 1.9 mmol) in dry methylene chloride (22 mL) was added boron tribromide (3.8 mL of a 1.0M solution of boron tribromide in methylene chloride, 3.8 mmol). The resulting solution was stirred at room temperature for 3 hours, diluted with methylene chloride (50 mL) and washed with water. The organic layer was dried (MgSO$_4$) and concentrated in vacuo to yield an off-white foam. Purification by flash column chromatography (10% to 30% v/v ethyl acetate in methylene chloride) yielded the title propanamide as a white solid (0.34 g, 46%); mp 155°–156° C. $^1$H-NMR (250 MHz, d6-DMSO): 1.58 (s, 3H, CH$_3$) 7.30 (dd, 1H, J=8.8,1.8 Hz, aromatic) 7.48 (s, 1H, OH) 7.51–1.66 (m, 4H, aromatic) 7.80–7.86 (m, 3H, aromatic) 10.19 (s, 1H, NH) 10.60 (s, 1H, OH). MS (CI, CH$_4$): 390 (M+1).

Analysis for C$_{16}$H$_{14}$F$_3$NO$_5$S: Calculated: C, 49.36; H, 3.62; N, 3.60. Found: C, 49.24; H, 3.58; N, 3.57.

EXAMPLE 37

N-[3-Methoxy-4-(phenylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (1.80 g, 11.4 mmol) in N,N-dimethylacetamide (40 mL) was added thionyl chloride (1.36 g, 11.4 mmol) and the mixture stirred at −10° to −15° C. for 1 hour. 3-Methoxy-4-(phenylsulfonyl)benzeneamine (2.00 g, 7.6 mmol) was added in one portion and the reaction mixture stirred at room temperature overnight. The mixture was poured into water and the aqueous solution filtered through a pad of Celite. The Celite was washed with methylene chloride (200 mL), the organic extract dried (MgSO$_4$), and the solvent removed in vacuo to yield a brown oil which was purified by flash column chromatography (10% v/v ethyl acetate/methylene chloride). The resulting white solid (2.52 g, 82%) melted at 202°–204° C. $^1$H-NMR (250 MHz, d6-DMSO): 1.56 (s, 3H, CH$_3$) 3.87 (s, 3H, OCH$_3$) 7.70–7.54 (m, 6H, aromatic+OH) 7.85–7.88 (m, 2H, aromatic) 7.93 (d, 1H, J=8.7 Hz, aromatic) 10.32 (s, 1H, NH). MS (CI, CH$_4$): 404 (M+1).

Analysis for C$_{17}$H$_{16}$F$_3$NO$_5$S: Calculated: C, 50.62; H, 4.00; N, 3.47. Found: C, 50.38; H, 3.97; N, 3.44.

The starting benzeneamine was made as follows:

a. 3-Methoxy-4-(phenylsulfonyl)benzeneamine

A stirred solution of 2-methoxy-4-nitrodiphenylsulfone (6.15 g, 2.1 mmol) and stannous chloride dihydrate (23.64 g, 10.5 mmol) in absolute ethanol (100 mL) was heated at reflux for 1 hour. The reaction mixture was poured into ice water, and the aqueous solution basified with 15% NaOH and extracted with ethyl acetate (2×500 mL). The combined organic portions were dried (MgSO$_4$), filtered, and the solvent removed in vacuo to yield an off-white solid. Recrystallization from absolute ethanol yielded the title benzeneamine (4.49 g, 81%) as a white solid; mp 149°–151° C. $^1$H-NMR (250 MHz, d6-DMSO): 3.61 (s, 3H, OCH$_3$) 6.14–6.15 (m, 3H, aromatic) 6.23 (dd, 1H, J=8.4, 1.9 Hz, aromatic) 7.50–7.60 (m, 4H, aromatic) 7.78–7.82 (m, 2H, aromatic). MS (CI, CH$_4$): 264 (M+1).

Analysis for C$_{13}$H$_{13}$NO$_3$S: Calculated: C, 59.30; H, 4.98; N, 5.32. Found: C, 58.85; H, 5.00; N, 5.22.

b. 2-Methoxy-4-nitrodiphenylsulfone

To a stirred solution of 5-nitro-2-phenylthioanisole (8.27 g, 31.6 mmol) in glacial acetic acid (250 mL) was added potassium permanganate (6.00 g, 38.0 mmol) in distilled water (100 mL). The dark brown mixture was stirred at room temperature for 1 hour, then treated with solid sodium sulfite until the solution clarified. The mixture was diluted with water and filtered to yield a tan solid. Recrystallization from absolute ethanol yielded the title sulfone (7.71 g, 83%) as an off-white solid; mp 173°–176° C. $^1$H-NMR (250 MHz, d6-DMSO): 3.89 (s, 3H, CH₃) 7.64 (t, 2H, J=7.4 Hz, aromatic) 7.74 (d, 1H, J=7.4 Hz, aromatic) 7.89 (d, 1H, J=2.0 Hz, aromatic) 7.95 (d, 2H, J=7.4 Hz, aromatic) 8.02 (dd, 1H, J=8.6, 2.1 Hz, aromatic) 8.30 (d, 1H, J=8.7 Hz, aromatic). MS (CI, CH₄): 294 (M+1).

Analysis for $C_{13}H_{11}NO_5S$: Calculated: C, 53.24; H, 3.78; N, 4.78. Found: C, 52.96; H, 3.87; N, 4.76.

c. 5-Nitro-2-phenylthioanisole

A solution of 2-bromo-5-nitroanisole (10.00 g, 43.1 mmol) and potassium phenylthiolate (6.12 g, 41.2 mmol) in dimethylformamide (50 mL) was stirred at room temperature for 24 hours. The reaction mixture was poured into ice water and filtered. The resulting solid was recrystallized from 95% ethanol to yield the title anisole (8.33 g, 74%) as a yellow solid; mp 89°–91° C. ¹H-NMR (250 MHz, d6-DMSO): 4.02 (s, 3H, OCH₃) 6.71–6.75 (m, 1H, aromatic) 7.56–7.61 (m, 5H, aromatic) 7.74–7.78 (m, 2H, aromatic). MS (CI, CH₄): 262 (M+1).

Analysis for $C_{13}H_{11}NO_3S$: Calculated: C, 59.76; H, 4.24; N, 5.36. Found: C, 59.79; H, 4.31; N, 5.14.

EXAMPLE 38

N-4-(phenylsulfoxyl)phenyl]-3,3,3-trifluoro-2-hydroxy-2-methylpropanamide

To a stirred, cooled (−20° C.) solution of 3,3,3-trifluoro-2-hydroxy-2-methylpropanoic acid (1.09 g, 6.9 mmol) in N,N-dimethylacetamide (10 mL) was added thionyl chloride (0.82 g, 6.9 mmol) and the mixture stirred at −10° to −15° C. for 1 hour. 4-Aminodiphenylsulfoxide (1.00 g, 4.6 mmol) was added in one portion and the reaction mixture stirred at room temperature overnight. The mixture was poured into water and the aqueous solution filtered through a pad of Celite. The Celite was washed with methylene chloride (100 mL), the organic extract dried (MgSO₄), filtered and the solvent removed in vacuo to yield a brown oil which was purified by flash column chromatography (10% v/v diethyl ether/methylene chloride). The resulting oil was stirred with hexane and filtered to yield the title propanamide as a white solid; mp 156°–158° C. ¹H-NMR (300 MHz, d6-DMSO): 1.56 (s, 3H, CH₃) 7.49–7.56 (m, 4H, aromatic+OH) 7.65–7.70 (m, 4H, aromatic) 7.91 (d, 2H, J=8.7 Hz, aromatic) 10.24 (s, 1H, NH). MS (CI, CH₄): 358 (M+1).

Analysis for $C_{16}H_{14}F_3NO_3S$: Calculated: C, 50.62; H, 4.00; N, 3.47. Found: C, 50.38; 3.97; N, 3.44.

4-Aminodiphenylsulfoxide is described in H. H. Szmant, J. J. McIntosh, J. Am. Chem. Soc., 73, 4356 (1951).

EXAMPLE 39

N-[4-(2-Hydroxyphenylsulfonyl)phenyl]-3,3,3-trifluoro-2-hydroxy-2-methylpropanamide To a stirred suspension of N-[4-(2-methoxyphenylsulfonyl)phenyl]-3,3,3-trifluoro-2-hydroxy-2-methylpropanamide (1.14 g, 2.8 mmol) in dry methylene chloride (30 mL) was added boron tribromide (8.5 mL of a 1.0M solution of boron tribromide in methylene chloride, 8.5 mmol). The resulting solution was stirred at room temperature for 3 hours, diluted with methylene chloride (50 mL) and washed with water. The organic layer was dried (MgSO₄) and concentrated in vacuo to yield an off-white solid which was dissolved in ethyl acetate (10 mL) and dropped into hexane (300 mL). Collection of the precipitate by filtration yielded the title propanamide as a white solid (0.84 g, 77%); mp 184°–186° C. ¹H-NMR (250 MHz, d6-DMSO): 1.57 (s, 3H, CH₃) 6.90 (d, 1H, J=8.3 Hz, aromatic) 7.01 (t, 1H, J=7.5 Hz, aromatic) 7.50 (m, 1H, aromatic) 7.56 (s, 1H, OH) 7.85–7.97 (m, 5H, aromatic) 10.37 (s, 1H, NH) 10.74 (s, 1H, OH). MS (CI, CH₄): 390 (M+1).

Analysis for $C_{16}H_{14}F_3NO_5S$: Calculated: C, 49.36; H, 3.62; N, 3.60. Found: C, 49.34; H, 3.83; N, 3.42.

EXAMPLE 40

N-[4-(2-Methoxyphenylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (1.42 g, 9.0 mmol) in N,N-dimethylacetamide (13 mL) was added thionyl chloride (1.13 g, 9.5 mmol) and the mixture stirred at −15° to −5° C. for 1 hour. 4-(2-Methoxyphenyl)sulfonyl-benzeneamine (1.58 g, 6.0 mmol) was added in one portion and the reaction mixture stirred at room temperature overnight. The mixture was poured into 250 mL of 0.5N HCl. The clear supernatient was decanted from the resulting gum. The gum was crystallized from methylene chloride/hexane to yield the title propanamide which contained about 10 mole % of methylene chloride by NMR analysis. The methylene chloride was not removed by heating at 140°/0.1 mm for 40 hours. The yield of white solid was 1.70 g (69%), mp 209°–211° C. ¹H-NMR (300 MHz, d6-DMSO): 1.55 (s, 3H, CH₃) 3.72 (s, 3H, OCH₃) 5.73 (s, CH₂Cl) 7.11–7.17 (m, 2H, aromatic) 7.53 (s, 1H, OH) 7.60–7.63 (m, 1H, aromatic) 7.80–7.83 (m, 2H, aromatic) 7.92–7.97 (m, 3H, aromatic) 10.36 (s, 1H, NH). MS (CI, CH₄): 294 (M+1).

Analysis for $C_{17}H_{16}F_3NO_5S \cdot 0.1 CH_2Cl_2$: Calculated: C, 49.87; H, 3.96; N, 3.40. Found: C, 49.71; H, 3.96; N, 3.35.

The starting benzeneamine was made as follows:

a. 4-(2-Methoxyphenyl)sulfonylbenzeneamine

To a stirred slurry of 2-methoxy-4'-nitrodiphenylsulfone (12.36 g, 4.2 mmol) in absolute ethanol (90 mL) was added in one portion stannous chloride dihydrate (47.4 g, 21 mmol) and the mixture heated to 50° C. where an exothermic reaction occurred. The reaction mixture was stirred at ambient temperature for 30 minutes, poured into ice water, the aqueous solution basified with 15% NaOH and extracted with methylene chloride (3×275 mL). The combined organic portions were dried (MgSO₄), filtered, and the solvent removed in vacuo to yield a white solid. Recrystallization from ethyl acetate yielded the title benzeneamine (5.38 g, 49%) as a white solid; mp 206°–208° C.

¹H-NMR (300 MHz, d6-DMSO): 3.75 (s, 3H, OCH₃) 6.10 (s, 2H, NH₂) 6.56–6.61 (m, 2H, aromatic) 7.08–7.13 (m, 2H, aromatic) 7.49–7.61 (m, 3H, aromatic) 7.91 (dd, 1H, J=8.2 Hz, J=1.8 Hz, aromatic). MS (CI, CH₄): 264 (M+1).

Analysis for $C_{13}H_{13}NO_3S$: Calculated: C, 59.30; H, 4.98; N, 5.32. Found: C, 59.28; H, 5.04; N, 5.20.

b. 2-Methoxy-4'-nitrodiphenylsulfone

To a stirred solution of 2-methoxy-4'-nitrodiphenylsulfide (13.73 g, 52.5 mmol) in glacial acetic acid (800 mL) was added potassium permanganate (9.97 g, 63 mmol) in distilled water (350 mL). The dark brown mixture was stirred at room temperature for 45 minutes, poured into 2 L of water, treated with solid sodium sulfite until the solution clarified and the solid collected by filtration. Recrystallization twice from absolute ethanol (300 mL) yielded the title sulfone (7.71 g, 83%) as white plates; mp 140°–142° C.

¹H-NMR (300 MHz, CDCl₃): 3.79 (s, 3H, CH₃) 6.94 (d, 1H, J=8.4 Hz, aromatic) 7.16 (t, 1H, J=7.6 Hz, aromatic) 7.58–7.64 (m, 1H, aromatic) 8.13–8.19 (m, 3H, aromatic) 8.31–8.35 (m, 2H, aromatic). MS (CI, CH₄): 294 (M+1).

Analysis for $C_{13}H_{11}NO_5S$: Calculated: C, 53.24; H, 3.78; N, 4.78. Found: C, 52.23; H, 3.79; N, 4.79.

c. 2-Methoxy-4'-nitrodiphenylsulfide

A solution of 1-chloro-4-nitrobenzene (11.23 g, 71.3 mmol) and potassium 2-methoxybenzenethiolate [from 2-methoxythiophenol (10.00 g, 71.3 mmol) and potassium hydroxide (4.00 g 71.3 mmol)] in dimethylformamide (90 mL) was stirred at room temperature for 18 hours. The reaction mixture was poured into ice water, stirred for 1 hour and filtered. The resulting solid was recrystallized once from 85% ethanol (150 mL) and twice from hexane (700 mL) to yield the title sulfide (13.83 g, 74%) as pale yellow needles; mp 90°–92° C. $^1$H-NMR (300 MHz, $CDCl_3$): 3.82 (s, 3H, $OCH_3$) 7.01–7.15 (m, 4H, aromatic) 7.46–7.55 (m, 2H, aromatic) 8.02–8.07 (m, 2H, aromatic). MS (CI, $CH_4$): 262 (M+1).

Analysis for $C_{13}H_{11}NO_3S$: Calculated: C, 59.76; H, 4.24; N, 5.36. Found: C, 59.70; H, 4.25; N, 4.71.

EXAMPLE 41

N-[4-(4-Fluorophenylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (0.94 g, 6.0 mmol) in N,N-dimethylacetamide (10 mL) was added thionyl chloride (0.71 g, 6.0 mmol) and the mixture stirred at −10° to −15° C. for 1 hour. 4-(4-Fluorophenylsulfonylbenzeneamine (1.00 g, 4.0 mmol) was added in one portion and the reaction mixture stirred at room temperature overnight. The mixture was poured into water and the aqueous solution filtered to yield a brown solid. Purification by flash column chromatography (5% v/v ethyl acetate/methylene chloride) yielded the title propanamide as a white solid (1.11 g, 71%); mp 168°–170° C. $^1$H-NMR (300 MHz, d6-DMSO): 1.57 (s, 3H, $CH_3$) 7.46 (t, 2H, J=8.8 Hz, aromatic) 7.57 (s, 1H, OH) 7.93 (d, 2H, J=8.8 Hz, aromatic) 7.99–8.04 (m, 4H, aromatic) 10.43 (s, 1H, NH). MS (CI, $CH_4$): 392 (M+1).

Analysis for $C_{16}H_{13}F_4NO_4S$: Calculated: C, 49.11; H, 3.35; N, 3.58. Found: C, 48.92; H, 3.37; N, 3.45.

4-[(4-Fluorophenyl)sulfonyl]benzeneamine is described in N. Sharghi, I. Lalezari, J. Chem. Eng. Data, 8, 276, (1963).

EXAMPLE 42

N-[4-(3-Fluorophenylsulfonyl)phenyl]-3,3,3-trifluoro-2-hydroxy-2-methylpropanamide.

To a stirred, cooled (−20° C.) solution of 3,3,3-trifluoro-2-hydroxy-2-methylpropanoic acid (0.94 g, 6.0 mmol) in N,N-dimethylacetamide (10 mL) was added thionyl chloride (0.71 g, 6.0 mmol) and the mixture stirred at −10° to −15° C. for 1 hour. 4-(3-Fluorophenylsulfonylbenzeneamine (1.00 g, 4.0 mmol) was added in one portion and the reaction mixture stirred at room temperature overnight. The mixture was poured into water and the aqueous solution filtered to yield a brown solid which was purified by flash column chromatography (5% v/v ethyl acetate/methylene chloride). Trituration of the resulting solid with ethyl ether yielded the title propanamide as a white solid (1.15 g, 73%); mp 147°–148° C. $^1$H-NMR (300 MHz, d6-DMSO): 1.57 (s, 3H, $CH_3$) 7.56–7.58 (m, 2H, aromatic+OH) 7.68–7.69 (m, 1H, aromatic) 7.78–7.82 (m, 2H, aromatic) 7.97 (d, 2H, J=8.9 Hz, aromatic) 8.03 (d, 2H, J=9.1, aromatic) 10.45 (s, 1H, NH). MS (CI, $CH_4$): 392 (M+1).

Analysis for $C_{16}H_{13}F_4NO_4S$: Calculated: C, 49.11; H, 3.35; N, 3.58. Found: C, 49.03; H, 3.43; N, 3.50.

4-(3-Fluorophenyl)sulfonylbenzeneamine is described in N. Sharghi, I. Lalezari, J. Chem. Eng. Data, 8, 276, (1963).

EXAMPLE 43

N-[4-(3-Hydroxyphenylsulfonyl)phenyl]-3,3,3-trifluoro-2-hydroxy-2-methylpropanamide To a stirred suspension of N-[4-(3-methoxyphenylsulfonyl)phenyl]-3,3,3-trifluoro-2-hydroxy-2-methylpropanamide (1.25 g, 3.1 mmol) in dry methylene chloride (30 mL) was added boron tribromide (9.3 mL of a 1.0M solution of boron tribromide in methylene chloride, 9.3 mmol). The resulting solution was stirred at room temperature for 2 hours, diluted with methylene chloride (50 mL) and washed with water. The organic layer was dried ($MgSO_4$) and concentrated in vacuo. The resulting tan solid was triturated with methylene chloride to yield the title propanamide as a white solid (0.98 g, 78%); mp 164–167° C. $^1$H-NMR (300 MHz, d6-DMSO): 1.57 (s, 3H, $CH_3$) 7.00–7.04 (m, 1H, aromatic) 7.24 (t, 1H, J=1.6 Hz, aromatic) 7.31–7.40 (m, 2H, aromatic) 7.55 (s, 1H, OH) 7.89 (d, 2H, J=8.9 Hz, aromatic) 8.00 (d, 2H, J=9.0 Hz, aromatic) 10.22 (s, 1H, NH), 10.41 (s, 1H, ArOH). MS (CI, $CH_4$): 390 (M+1).

Analysis for $C_{16}H_{14}F_3NO_5S \cdot 0.50\ H_2O$: Calculated: C, 48.20; H, 3.51; N, 3.51. Found: C, 47.98; H, 3.71; N, 3.44.

EXAMPLES 44

N-[4-(3-Methoxyphenylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (1.[680 g, 11.4 mmol) in N,N-dimethyl-acetamide (10 mL) was added thionyl chloride (1.36 g, 11.4 mmol) and the mixture stirred at −10° to −15° C. for 1 hour. 4-[(3-Methoxy-phenyl)sulfonyl]-benzeneamine (2.00 g, 7.6 mmol) was added in one portion and the reaction mixture stirred at room temperature overnight. The mixture was poured into water and the aqueous solution filtered to yield a brown solid. Purification by flash column chromatography (10% v/v ethyl acetate/methylene chloride) yielded the title propanamide as a white solid (2.75 g, 90%); mp 147°–148° C. $^1$H-NMR (300 MHz, d6-DMSO): 1.58 (s, 3H, $CH_3$) 3.83 (s, 3H, $OCH_3$) 7.22–7.25 (m, 1H, aromatic) 7.41–7.42 (m, 1H, aromatic) 7.47–7.56 (m, 3H, aromatic+OH) 7.93–8.01 (m, 4H, aromatic) 10.42 (s, 1H, NH). MS (CI, $CH_4$): 404 (M+1).

Analysis for $C_{17}H_{16}F_3NO_5S$: Calculated: C, 50.62; H, 3.40; N, 3.47. Found: C, 50.14; H, 3.40; N, 3.40.

a. 4-[(3-Methoxyphenyl)sulfonyl]benzeneamine

A stirred solution of 3-methoxy-4'-nitrodiphenylsulfone (7.56 g, 25.8 mmol) and stannous chloride dihydrate (29.06 g, 129 mmol) in absolute ethanol (50 mL) was heated at reflux for 1 hour. The reaction mixture was poured into ice water, the aqueous solution basified with 15% NaOH and extracted with ethyl acetate (2×200 mL). The combined organic portions were dried ($MgSO_4$), filtered, and the solvent removed in vacuo to yield an off-white solid. Recrystallization from absolute ethanol yielded the title benzeneamine (4.63 g, 68%) as a white solid; mp 116°–117° C. $^1$H-NMR (300 MHz, d6-DMSO): 3.81 (s, 3H, $OCH_3$) 6.20 (s, 2H, $NH_2$) 6.62–6.66 (m, 2H, aromatic) 7.15–7.19 (m, 1H, aromatic+OH) 7.32–7.60 (m, 5H, aromatic). MS (CI, $CH_4$): 264 (M+1).

Analysis for $C_{13}H_{13}NO_3S$: Calculated: C, 59.30; H, 4.98; N, 5.32. Found: C, 59.11; H, 5.04; N, 5.28.

b. 3-Methoxy-4'-nitrodiphenylsulfone

To a stirred solution of 3-(4-nitrophenylthio)anisole (7.79 g, 29.8 mmol) in glacial acetic acid (200 mL) was added potassium permanganate (5.65 g, 35.8 mmol) in distilled water (75 mL). The dark brown mixture was stirred at room temperature for 1 hour, then treated with solid sodium sulfite until the solution clarified. The mixture was diluted with water and filtered to yield a tan solid. Recrystallization from absolute ethanol yielded the title sulfone (7.56 g, 86%) as an off-white solid; mp 123°–125° C. $^1$H-NMR (250 MHz, d6-DMSO): 3.86 (s, 3H, OCH$_3$) 7.29–7.33 (m, 1H, aromatic) 7.51 (br s, 1H, aromatic) 7.59 (d, 2H, J=3.8 Hz, aromatic) 8.27 (dd, 2H, J=7.0, 1.9 Hz, aromatic) 8.39 (dd, 2H, J=7.0, 1.9 Hz, aromatic). MS (CI, CH$_4$): 294 (M+1).

Analysis for $C_{13}H_{11}NO_5S$: Calculated: C, 53.24; H, 3.78; N, 4.78. Found: C, 53.19; H, 3.85; N, 4.90.

c. 3-(4-Nitrophenylthio)anisole

A solution of potassium 3-methoxybenzenethiolate (6.37 g, 35.7 mmol) and 4-chloronitrobenzene (5.11 g, 32.5 mmol) in dimethylformamide (30 mL) was stirred at room temperature for 4 hours. The reaction mixture was poured into ice water and a yellow solid was collected by filtration. Recrystallization from 90% ethanol yielded the title anisole (7.79 g, 92%) as a yellow solid; mp 81°–83° C. $^1$H-NMR (250 MHz, d6-DMSO): 3.80 (s, 3H, OCH$_3$) 7.10–7.19 (m, 3H, aromatic) 7.32 (d, 2H, J=7.1 Hz, aromatic) 7.43–7.49 (m, 1H, aromatic) 8.15 (d, 2H, J=7.0, aromatic). MS (CI, CH$_4$): 262 (M+1).

Analysis for $C_{13}H_{11}NO_3S$: Calculated: C, 59.76; H, 4.24; N, 5.36. Found: C, 59.74; H, 4.40; N, 5.34.

EXAMPLE 45

N-[3-Methyl-4-(phenylsulfonyl)phenyl]-3,3,3-trifluoro-2-hydroxy-2-methylpropanamide To a stirred, cooled (–20° C.) solution of 3,3,3-trifluoro-2-hydroxy-2-methylpropanoic acid (0.72 g, 4.5 mmol) in N,N-dimethylacetamide (10 mL) was added thionyl chloride (0.54 g, 4.5 mmol) and the mixture stirred at –10° to –15° C. for 1 hour. 3-Methyl-4-(phenylsulfonyl)-benzeneamine (0.75 g, 3.0 mmol) was added in one portion and the reaction mixture stirred at room temperature overnight. The mixture was poured into water and the aqueous solution filtered to yield a brown solid which was purified by flash column chromatography (5% v/v ethyl acetate/methylene chloride). Trituration of the resulting solid with hexane yielded the title propanamide as a white solid (0.95 g, 82%); mp 141°–143° C. $^1$H-NMR (300 MHz, d6-DMSO): 1.58 (s, 3H, CH$_3$) 2.32 (s, 3H, ARCH$_3$) 7.55–7.70 (m, 4H, aromatic) 7.79–7.85 (m, 3H, aromatic) 7.92 (dd, 1H, J=8.8, 1.9 Hz, aromatic) 8.10 (d, 1H, J=8.8 Hz, aromatic) 10.30 (s, 1H, NH). MS (CI, CH$_4$): 388 (M+1).

Analysis for $C_{17}H_{16}F_3NO_4S$: Calculated: C, 52.71; H, 4.16; N, 3.62. Found: C, 52.59; H, 4.24; N, 3.59.

The starting benzeneamine was made as follows:

a. 3-Methyl-4-(phenylsulfonyl)benzeneamine

A stirred solution of 2-methyl-4-nitrodiphenylsulfone (2.72 g, 9.8 mmol) and stannous chloride dihydrate (11.06 g, 49.0 mmol) in absolute ethanol (30 mL) was heated at reflux for 1 hour. The reaction mixture was poured into ice water, the aqueous solution basified with 15% NaOH and extracted with ethyl acetate (2×100 mL). The combined organic portions were dried (MgSO$_4$), filtered, and the solvent removed in vacuo to yield an off-white solid. Recrystallization from ethyl acetate yielded the title benzeneamine (2.12 g, 88%) as a white solid; mp 163°–165° C. $^1$H-NMR (300 MHz, d6-DMSO): 2.17 (s, 3H, ArCH$_3$) 6.10 (s, 2H, NH$_2$) 6.38 (d, 1H, J=2.1 Hz, aromatic) 6.53 (dd, 1H, J=8.7, 2.2 Hz, aromatic) 7.54–7.62 (m, 4H, aromatic) 7.73–7.77 (m, 2H, aromatic). MS (CI, CH$_4$): 248 (M+1).

Analysis for $C_{13}H_{13}NO_2S$: Calculated: C, 63.14; H, 5.30; N, 5.66. Found: C, 63.10; H, 5.30; N, 5.62.

b. 2-Methyl-4-nitrodiphenylsulfone

To a stirred solution of 2-phenylthio-5-nitrotoluene (3.24 g, 13.2 mmol) in glacial acetic acid (70 mL) was added potassium permanganate (2.50 g, 15.8 mmol) in distilled water (30 mL). The dark brown mixture was stirred at room temperature for 2 hour, then treated with solid sodium sulfite until the solution clarified. The mixture was diluted with water and filtered to yield an off-white solid. Recrystallization from 95% ethanol yielded the title sulfone (2.75 g, 75%) as an off-white solid; mp 113°–114° C. $^1$H-NMR (250 MHz, d6-DMSO): 2.48 (s, 3H, ARCH$_3$) 7.63–7.80 (m, 3H, aromatic) 7.92 (d, 2H, J=7.4 Hz, aromatic) 8.25–8.38 (m, 3H, aromatic). MS (CI, CH$_4$): 278 (M+1).

Analysis for $C_{13}H_{11}NO_5S$: Calculated: C, 56.31; H, 4.00; N, 5.05. Found: C, 56.10; H, 4.14; N, 4.95.

2-Phenylthio-5-nitrotoluene is described in A. B. Sakla, et. al., Acta. Chim. Acad. Sci. Hung. 98 (4), 479 (1978). Chem. Abstr 90: 203595d.

EXAMPLE 46

N-[4-(2-Fluorophenylcarbonyl)phenyl]-3,3,3-trifluoro-2-hydroxy-2-methylpropanamide To a stirred, cooled (–20° C.) solution of 3,3,3-trifluoro-2-hydroxy-2-methylpropanoic acid (1.10 g, 7.0 mmol) in N,N-dimethylacetamide (10 mL) was added thionyl chloride (0.83 g, 7.0 mmol) and the mixture stirred at –10° to –15° C. for 1 hour. 4-Amino-2'-fluoro benzophenone (1.00 g, 4.6 mmol) was added in one portion and the reaction mixture stirred at room temperature overnight. The mixture was poured into water and the aqueous solution filtered to yield a brown solid. Purification by flash column chromatography (5% v/v ethyl acetate/methylene chloride) yielded the title propanamide as a white solid (1.23 g, 75%); mp 141°–142° C. $^1$H-NMR (300 MHz, d6-DMSO): 1.60 (s, 3H, CH$_3$) 7.35–7.42 (m, 2H, aromatic) 7.53–7.59 (m, 2H, aromatic+OH) 7.65–7.68 (m, 1H, aromatic) 7.75 (d, 2H, J=8.5 Hz, aromatic) 7.96 (dd, 2H, J=8.6, 1.7 Hz, aromatic) 10.37 (s, 1H, NH). MS (CI, CH$_4$): 356 (M+1).

Analysis for $C_{17}H_{13}F_4NO_3$: Calculated: C, 57.47; H, 3.69; N, 3.94. Found: C, 57.44; H, 3.77; N, 3.91.

The starting benzophenone was made as follows:

a. 4-Amino-2'-fluorobenzophenone

To stirred 90° C. polyphosphoric acid (200 g) was added 14.29 g (10.2 mmol) of 2-fluorobenzoic acid and aniline (9.32 g 10.0 mmol) and the bath temperature raised to 180°–190° C. and held there for 1 hour. A solution was obtained at about 140° C. The heating bath was removed and the stirred mixture (sublimate above the solution) was treated cautiously with 80 mL of water. The mixture was stirred at 140°–155° C. for 1 hour, the heating bath removed, 66 mL of 3N HCl added, the mixture poured into 1 L of water and filtered through a pad of Celite. The filtrate was basified with 15% sodium hydroxide and the solid which formed on stirring was collected. The Celite pad was washed well with methylene chloride, the methylene chloride removed and the residue was combined with the solid obtained from basification of the aqueous phase. The combined material was dissolved in refluxing ethanol (175 mL), and treated hot with 125 mL of water. The brown solid obtaing on cooling was additionally recrystallized twice from ethyl acetate-hexane. Final purification by flash column chromatography (methylene chloride) yielded the aniline as a white solid (5.45 g. 25%); mp 128°–130° C. ¹H-NMR (250 MHz, d6-DMSO): 6.32 (s, 2H, NH$_2$) 6.60 (dd, 2H, J=8.6, 1.5 Hz, aromatic) 7.28–7.35 (m, 2H, aromatic) 7.40–7.60 (m, 4H, aromatic). MS (CI, CH$_4$): 216 (M+1).

Analysis for C$_{13}$H$_{10}$FNO: Calculated: C, 72.55; H, 4.68; N, 6.51. Found: C, 72.46; H, 4.82; N, 6.21.

EXAMPLE 47

N-[3- Hydroxy-4-(4-pyridylsulfonyl)phenyl]-3,3,3-trifluoro-2-hydroxy-2-methylpropanamide To a stirred suspension of N-[3-methoxy-4-(4-pyridylsulfonyl)phenyl]-3,3,3-trifluoro-2-hydroxy-2-methylpropanamide (1.05 g, 2.6 mmol) in dry methylene chloride (30 mL) was added boron tribromide (10.4 mL of a 1.0M solution of boron tribromide in methylene chloride, 10.4 mmol). The resulting solution was stirred at reflux for 2 hours. An additional 5 mL of 1.0M boron tribromide solution in methylene chloride was added and the reaction stirred overnight at room temperature. The reaction mixture was diluted with methylene chloride (50 mL) and washed with water. The organic layer was dried (MgSO$_4$) and concentrated in vacuo to yield an oil. Purification by flash column chromatography (20% v/v methanol in ethyl acetate) yielded the title propanamide as a white solid (0.18 g, 18%); mp 188–189° C. ¹H-NMR (250 MHz, d6-DMSO): 1.54 (s, 3H, CH$_3$) 7.35 (d, 1H, J=9.0 Hz, aromatic) 7.51 (s, 1H, OH) 7.61 (s, 1H, aromatic) 7.77 (d, 2H, J=5.5 Hz, aromatic) 7.84 (d, 1H, J=8.9 Hz, aromatic) 8.83 (d, 2H, J=5.5 Hz, aromatic) 10.26 (s, 1H, NH) 11.04 (s, 1H, ArOH). MS (CI, CH$_4$): 391 (M+1).

Analysis for C$_{15}$H$_{13}$F$_3$N$_2$O$_5$S.0.25 H$_2$O: Calculated: C, 45.63; H, 3.44; N, 7.09. Found: C, 45.51; H, 3.58; N, 6.98.

EXAMPLE 48

N-[3-Methoxy-4-(4-pyridylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (1.79 g, 11.3 mmol) in N,N-dimethylacetamide (20 mL) was added thionyl chloride (1.34 g, 11.3 mmol) and the mixture stirred at −10° to −15° C. for 1 hour. 3-Methoxy-4-(4-pyridylsulfonyl)benzeneamine (2.00 g, 7.6 mmol) was added in one portion and the reaction mixture stirred at room temperature overnight. The mixture was poured into water and the aqueous solution filtered through Celite. The Celite was washed with methylene chloride (100 mL), the methylene chloride solution dried (MgSO$_4$) and concentrated in vacuo to an off-white solid. Trituration with ethyl ether yielded the title propanamide as a white solid (1.65 g, 54%); mp 238°–240° C.

¹H-NMR (250 MHz, d6-DMSO): 1.58 (s, 3H, CH$_3$) 3.70 (s, 3H, OCH$_3$) 7.60 (s, 1H, OH) 7.71 (d, 1H, J=4.6 Hz, aromatic) 7.75–7.79 (m, 3H, aromatic) 7.96 (d, 1H, J=8.8 Hz, aromatic) 8.85 (dd, 2H, J=4.6, 1.1 Hz, aromatic) 10.39 (s, 1H, NH). MS (CI, CH$_4$): 405 (M+1).

Analysis for C$_{16}$H$_{15}$F$_3$N$_2$O$_5$S: Calculated: C, 47.53; H, 3.74; N, 6.93; Found: C, 47.45; H, 3.79; N, 6.79;

The starting benzeneamine was made as follows:

a. 3-Methoxy-4-(4-pyridylsulfonyl)benzeneamine

A stirred solution of 5-nitro-2-(4-pyridylsulfonyl)anisole (3.00 g, 10.2 mmol) and stannous chloride dihydrate (11.49 g, 51.0 mmol) in absolute ethanol (35 mL) was heated at reflux for 1 hour. The reaction mixture was poured into ice water, and the aqueous solution basified with 15% NaOH and extracted with ethyl acetate (2×200 mL). The combined organic portions were dried (MgSO$_4$) and the solvent removed in vacuo to yield the title benzeneamine as a pale yellow solid (2.23 g, 83%); mp 150°–152° C. ¹H-NMR (250 MHz, d6-DMSO): 3.62 (s, 3H, OCH$_3$) 6.18 (d, 1H, J=1.8 Hz, aromatic) 6.24 (d, 1H, J=1.9 Hz, aromatic) 6.28 (s, 2H, NH$_2$) 7.58 (d, 1H, J=8.8 Hz, aromatic) 7.70 (dd, 2H, J=4.5, 1.5 Hz, aromatic) 8.79 (dd, 2H, J=4.4, 1.6 Hz, aromatic). MS (CI, CH$_4$): 265 (M+1).

Analysis for C$_{12}$H$_{12}$N$_2$O$_3$S: Calculated: C, 54.53; H, 4.58; N, 10.60. Found: C, 54.36; H, 5.56; N, 10.44.

b. 5-Nitro-2-(4-pyridylsulfonyl)anisole

To a stirred solution of 5-nitro-2-(4-pyridylthio)anisole (5.00 g, 19.1 mmol) in glacial acetic acid (150 mL) was added potassium permanganate (3.61 g, 22.9 mmol) in distilled water (75 mL). The dark brown mixture was stirred at room temperature for 1 hour, then treated with solid sodium sulfite until the solution clarified. The mixture was diluted with water and filtered to yield a brown solid. Recrystallization from absolute ethanol yielded the title sulfone (3.63 g, 65%) as a tan solid; mp 173°–175° C. ¹H-NMR (250 MHz, d6-DMSO): 3.90 (s, 3H, OCH$_3$) 7.90–7.94 (m, 3H, aromatic) 8.06 (d, 1H, J=7.8 Hz, aromatic) 8.33 (d, 1H, J=7.9 Hz, aromatic) 8.92 (br s, 2H, aromatic). MS (CI, CH$_4$): 295 (M+1).

Analysis for C$_{12}$H$_{10}$N$_2$O$_5$S.0.5 H$_2$O: Calculated: C, 48.24; H, 3.54; N, 9.38 Found: C, 48.20; H, 3.48; N, 9.46 c. 5-Nitro-2-(4-pyridylthio)anisole

A solution of potassium 4-pyridinethiolate (20.00 g, 134 mmol) and 2-chloro-5-nitroanisole (20.91 g, 112 mmol) in dimethylformamide (80 mL) was stirred at room temperature for 24 hours. The reaction mixture was poured into ice water and a brown solid was collected by filtration. The solid was stirred with 3N HCl (400 mL) for 30 minutes, and the solution filtered. The filtrate was basified with ammonium hydroxide with cooling in an ice bath. Filtration of the basic solution yielded the title anisole as an orange solid (26.23 g, 90%); mp 133°–135° C. ¹H-NMR (300 MHz, d6-DMSO): 3.95 (s, 3H, OCH$_3$) 7.24 (dd, 2H, J=4.6, 1.7 Hz, aromatic) 7.53 (d, 1H, J=8.3 Hz, aromatic) 7.88 (dd, 2H, J=8.3, 2.3 Hz, aromatic) 8.48 (dd, 2H, J=4.7, 1.3 Hz, aromatic). MS (CI, CH$_4$): 263 (M+1).

Analysis for C$_{12}$H$_{10}$N$_2$O$_3$S: Calculated: C, 54.95; H, 3.84; N, 10.68. Found: C, 54.81; H, 3.92; N, 10.70.

EXAMPLE 49

N-[3-Fluoro-4-(phenylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (0.71 g, 4.5 mmol) in N,N-dimethylacetamide (10 mL) was added thionyl chloride (0.54 g, 4.5 mmol) and the mixture stirred at −10° to −15° C. for 1 hour. 3-Fluoro-4-(phenylsulfonyl)benzeneamine (0.75 g, 3.0 mmol) was added in one portion and the reaction mixture stirred at room temperature overnight. The mixture was poured into water and the aqueous solution filtered through Celite. The Celite was washed with methylene chloride (75 mL), the organic extract dried (MgSO$_4$) and concentrated in vacuo to a tan solid. Purification by flash column chromatography (5% v/v ethyl acetate/methylene chloride) yielded the title propanamide as a white solid (0.79 g, 68%); mp 147°–149° C. ¹H-NMR (250 MHz, d6-DMSO): 1.58 (s, 3H, CH$_3$) 7.65–7.69 (m, 4H, aromatic+OH) 7.74 (d, 1H, J=7.2 Hz, aromatic) 7.83–7.94 (m, 3H, aromatic) 8.02 (t, 1H, J=8.3 Hz, aromatic) 10.61 (s, 1H, NH). MS (CI, CH$_4$): 392 (M+1).

Analysis for $C_{16}H_{13}F_4NO_4S$: Calculated: C, 49.12; H, 3.35; N, 3.58. Found: C, 48.91; H, 3.28; N, 3.53.

The starting benzeneamine was made as follows:

a. 3-Fluoro-4-(phenylsulfonyl)benzeneamine

A stirred solution of 2-fluoro-4-nitrodiphenylsulfone (4.78 g, 17.0 mmol) and stannous chloride dihydrate (21.62 g, 95.9 mmol) in absolute ethanol (50 mL) was heated at reflux for 1 hour. The reaction mixture was poured into ice water, and the aqueous solution basified with 15% NaOH and extracted with ethyl acetate (3×200 mL). The combined organic portions were dried ($MgSO_4$), filtered and the solvent removed in vacuo to yield an off-white solid. Recrystallization from absolute ethanol yielded the title benzeneamine (3.43 g, 80%) as a white solid; mp 161°–163° C. $^1$H-NMR (250 MHz, d6-DMSO): 6.32 (dd, 1H, J=13.5, 1.8 Hz, aromatic) 6.47 (d, 1H, J=2.0 Hz, aromatic) 6.50 (s, 2H, $NH_2$) 7.59–7.67 (m, 4H, aromatic) 7.85 (d, 2H, J=7.6 Hz, aromatic). MS (CI, $CH_4$): 252 (M+1).

Analysis for $C_{12}H_{10}NO_2S$: Calculated: C, 57.36; H, 4.01; N, 5.57 Found: C, 57.27; H, 4.15; N, 5.58.

b. 2-Fluoro-4-nitrodiphenylsulfone

To a stirred solution of 3-fluoro-4-(phenylthio)nitrobenzene (5.65 g, 22.7 mmol) in glacial acetic acid (200 mL) was added potassium permanganate (4.30 g, 27.2 mmol) in distilled water (75 mL). The dark brown mixture was stirred at room temperature for 1 hour, then treated with solid sodium sulfite until the solution clarified. The mixture was diluted with water and filtered to yield an off-white solid. Recrystallization from absolute ethanol yielded the title sulfone (4.80 g, 75%) as an off-white solid; mp 124°–125° C. $^1$H-NMR (300 MHz, DMSO-d6): 7.68–7.73 (m, 2H, aromatic) 7.79–7.84 (m, 1H, aromatic) 8.00 (d, 2H, J=8.2 Hz, aromatic) 8.28–8.38 (m, 3H, aromatic). MS (CI, $CH_4$): 282 (M+1).

Analysis for $C_{12}H_8NO_4S$: Calculated: C, 51.25; H, 2.87; N, 4.98. Found: C, 51.30; H, 2.87; N, 4.53.

c. 3-Fluoro-4-(phenylthio)nitrobenzene

A solution of potassium phenylthiolate (9.50 g, 64.1 mmol) and 3,4-difluoronitrobenzene (10.00 g, 64.1 mmol) in dimethylformamide (40 mL) was stirred at room temperature for 24 hours. The reaction mixture was poured into ice water and a yellow solid was collected by filtration. Recrystallization from 95% ethanol yielded the title sulfide (10.68 g, 67%) as a yellow solid; mp 54°–55° C.

$^1$H-NMR (250 MHz, d6-DMSO): 7.03 (t, 1H, J=7.8 Hz, aromatic) 7.52–7.62 (m, 5H, aromatic) 8.00 (dd, 1H, J=8.9, 2.3 Hz, aromatic) 8.17 (dd, 1H, J=8.8, 2.3 Hz, aromatic). MS (CI, $CH_4$): 250 (M+1).

Analysis for $C_{12}H_8NO_2S$: Calculated: C, 57.82; H, 3.23; N, 5.62. Found: C, 57.71; H, 3.21; N, 5.35.

EXAMPLE 50

N-[4-(2,5-Difluorophenylcarbonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (0.95 g, 6.0 mmol) in N,N-dimethylacetamide (15 mL) was added thionyl chloride (0.72 g, 6.0 mmol) and the mixture stirred at −10° to −15° C. for 1 hour. 4'-Amino-2,5-difluoro benzophenone (1.00 g, 4.3 mmol) was added in one portion and the reaction mixture stirred at room temperature overnight. The mixture was poured into water and the aqueous solution filtered to yield a brown solid. Recrystallization from methylene chloride/hexane yielded the title propanamide as a white solid (1.03 g, 69%); mp 145°–147° C.

$^1$H-NMR (250 MHz, d6-DMSO): 1.59 (s, 3H, $CH_3$) 7.44–7.47 (m, 3H, aromatic) 7.57 (s, 1H, OH) 7.77 (d, 2H, J=8.0 Hz, aromatic) 7.97 (d, 2H, J=8.0 Hz, aromatic) 10.40 (s, 1H, NH). MS (CI, $CH_4$): 374 (M+1).

Analysis for $C_{17}H_{12}F_5NO_3$: Calculated: C, 54.70; H, 3.24; N, 3.75. Found: C, 54.29; H, 3.16; N, 3.72.

The starting benzophenone was made as follows:

a. 4'-Amino-2,5-difluorobenzophenone

To stirred 90° C. polyphosphoric acid (125 g) was added 2,5-difluoro-benzoic acid (10.0 g, 6.32 mmol) and aniline (5.87 g 6.3 mmol) and the bath temperature raised to 180°–190° C. and held there for 1 hour. The heating bath was removed and the stirred mixture (sublimate above the solution) was treated cautiously with 50 mL of water. The mixture was stirred at 140°–155° C. for 1 hour, the heating bath removed, 45 mL of 3N HCl added, the mixture poured into 650 mL of water and filtered through a pad of Celite. The filtrate was basified with 15% sodium hydroxide and the mixture filtered through a pad of Celite. The Celite pad was washed well with methylene chloride, the methylene chloride dried ($MgSO_4$), filtered and the solvent removed in vacuo. Purification by flash column chromatography (methylene chloride) followed by recrystallization twice from 50% ethanol (80 mL) yielded the aniline as a yellow solid (3.08 g, 21%); mp 101°–103° C. $^1$H-NMR (300 MHz, $CDCl_3$): 4.27 (s, 2H, $NH_2$) 6.63–6.67 (m, 2H, aromatic) 7.09–7.19 (m, 3H, aromatic) 7.68–7.71 (m, 2H, aromatic). MS (CI, $CH_4$): 234 (M+1).

Analysis for $C_{13}H_9F_2NO$: Calculated: C, 66.95; H, 3.89; N, 6.01. Found: C, 66.86; H, 4.04; N, 5.95.

EXAMPLE 51

N-[4-(2,3-Difluorophenylcarbonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (1.02 g, 6.4 mmol) in N,N-dimethylacetamide (10 mL) was added thionyl chloride (0.77 g, 6.4 mmol) and the mixture stirred at −10° to −15° C. for 1 hour. 4'-Amino-2,3-difluorobenzophenone (1.00 g, 4.3 mmol) was added in one portion and the reaction mixture stirred at room temperature overnight. The mixture was poured into water and the aqueous solution extracted with methylene chloride (2×50 mL). The combined organics were washed with water and 3N HCl (1×50 mL), dried ($MgSO_4$) and concentrated in vacuo to yield a tan solid. The solid was purified by flash column chromatography (5% v/v ethyl acetate/methylene chloride). Recrystallization of the resulting solid from methylene chloride/hexane yielded the title propanamide as a white solid (1.13 g, 70%); mp 154°–155° C. $^1$H-NMR (250 MHz, d6-DMSO): 1.60 (s, 3H, $CH_3$) 7.36–7.40 (m, 2H, aromatic) 7.57 (s, 1H, OH) 7.65–7.72 (m, 1H, aromatic) 7.89 (d, 2H, J=8.6 Hz, aromatic) 7.98 (d, 2H, J=8.6 Hz, aromatic) 10.40 (s, 1H, NH). MS (CI, $CH_4$): 374 (M+1).

Analysis for $C_{17}H_{12}F_5NO_3 \cdot 0.25 \ H_2O$: Calculated: C, 54.05; H, 3.33; N, 3.70. Found: C, 54.01; H, 3.17; N, 3.68.

The starting benzophenone was made as follows:

a. 4'-Amino-2,3-difluorobenzophenone

To stirred polyphosphoric acid (125 g) heated to 90° C. was added 2,3-difluorobenzoic acid (10.00 g, 63.3 mmol) followed by aniline (5.72 g, 61.7 mmol). The reaction mixture was heated at 180°–185° C. for 1 hour (solid dissolved at 135° C.), then the oil bath was removed and distilled water (35 mL) was cautiously added in small portions through the condenser. The oil bath was returned, and the reaction mixture heated at 135°–145° C. for 1 hour. The oil bath was again removed, 3N HCl (55 mL) was added to the solution, the reaction mixture was then poured into water (750 mL) and stirred for one hour. The aqueous solution was filtered through Celite and the filtrate basified with 15% NaOH to a pH of 8. A green solid was collected by filtration and purified by flash column chromatography (methylene chloride). Trituration with hexane yielded the title benzophenone (1.43 g, 10%) as a yellow solid; mp 104°–106° C. $^1$H-NMR (250 MHz, d6-DMSO): 6.41 (s, 2H, NH$_2$) 6.60 (d, 2H, J=8.7 Hz, aromatic) 7.22–7.37 (m, 2H, aromatic) 7.50 (d, 2H, J=8.6 Hz, aromatic) 7.53–7.64 (m, 1H, aromatic). MS (CI, CH$_4$): 234 (M+1).

Analysis for C$_{13}$H$_9$F$_2$NO: Calculated: C, 66.94; H, 3.90; N, 6.00. Found: C, 66.87; H, 3.80; N, 5.91.

EXAMPLE 52

N-[4-(2-Cyanophenylsulfonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (0.82 g, 5.2 mmol) in N,N-dimethylacetamide (10 mL) was added thionyl chloride (0.62 g, 5.2 mmol) and the mixture stirred at −10° to −15° C. for 1 hour. 4-[(2-Cyanophenyl)sulfonyl]benzeneamine (1.00 g, 3.8 mmol) was added in one portion and the reaction mixture stirred at room temperature overnight. The mixture was poured into water and the aqueous solution decanted from an oily solid which was purified by flash column chromatography (5% v/v ethyl acetate/methylene chloride). Recrystallization from methylene chloride/hexane yielded the title propanamide as a white solid (1.08 g, 72%); mp 156°–158° C. $^1$H-NMR (250 MHz, d6-DMSO): 1.58 (s, 3H, CH$_3$) 7.59 (s, 1H, OH) 7.88–8.13 (m, 7H, aromatic) 8.31 (d, 1H, J=6.9 Hz, aromatic) 10.50 (s, 1H, OH). MS (CI, CH$_4$): 399 (M+1).

Analysis for C$_{17}$H$_{13}$F$_3$N$_2$O$_4$S.0.50 H$_2$O: Calculated: C, 50.12; H, 3.46; N, 6.87. Found: C, 49.86; H, 3.17; N, 6.80.

The starting benzeneamine was made as follows:
a. 4-[(2-Cyanophenyl)sulfonyl]benzeneamine A stirred solution of 2-cyano-4'-nitrodiphenylsulfone (2.54 g, 8.8 mmol) and iron powder (5.39 g, 96.5 mmol) in absolute ethanol (70 mL) was heated to reflux. Ethanolic HCl (0.53 mL concentrated HCl in 20 mL EtOH) was added dropwise over 30 minutes. The reaction mixture was heated at reflux for 4 hours, diluted with absolute ethanol (100 mL) and filtered while hot through Celite. The Celite was washed with additional hot ethanol (100 mL). The combined ethanol portions were reduced to a volume of 75 mL and placed in a freezer overnight. The title benzeneamine was collected by filtration as a white solid (1.81 g, 80%); mp 177°–179° C. $^1$H-NMR (300 MHz, d6-DMSO): 6.37 (s, 2H, NH$_2$) 6.65 (d, 2H, J=8.8 Hz, aromatic) 7.61 (d, 2H, J=8.8 Hz, aromatic) 7.81 (dd, 1H, J=7.5, 1.0 Hz, aromatic) 7.93 (dt, 1H, J=7.6, 1.1 Hz, aromatic) 8.06 (dd, 1H, J=7.5, 1.0 Hz, aromatic) 8.17 (d, 1H, J=7.4 Hz, aromatic). MS (CI, CH$_4$): 259 (M+1).

Analysis for C$_{13}$H$_{10}$N$_2$O$_2$S.0.25 H$_2$O: Calculated: C, 59.41; H, 3.84; N, 10.66. Found: C, 59.39; H, 3.82; N, 10.60.
b. 2-Cyano-4'-nitrodiphenylsulfone To a stirred solution of 2-(4-nitrophenylthio)benzonitrile (3.25 g, 12.7 mmol) in glacial acetic acid (200 mL) was added potassium permanganate (2.41 g, 15.2 mmol) in distilled water (75 mL). The dark brown mixture was stirred at room temperature for 1.5 hours, then treated with solid sodium sulfite until the solution clarified. The mixture was diluted with water and filtered to yield a tan solid. Recrystallization from ethyl acetate/hexane yielded the title sulfone (2.56 g, 70%) as a white solid; mp 172°–174° C. $^1$H-NMR (250 MHz, d6-DMSO): 7.98–8.11 (m, 2H, aromatic) 8.19 (dd, 1H, J=7.1, 1.0 Hz, aromatic) 8.28 (d, 2H, J=8.8 Hz, aromatic) 8.45 (m, 1H, aromatic) 8.49 (d, 2H, J=8.9 Hz, aromatic). MS (CI, CH$_4$): 289 (M+1).

Analysis for C$_{13}$H$_8$N$_2$O$_4$S: Calculated: C, 54.16; H, 2.80; N, 9.72. Found: C, 53.83; H, 2.46; N, 9.63.
c. 2-(4-Nitrophenylthio)benzonitrile A stirred solution of potassium 4-nitrophenylthiolate (10.61 g, 54.9 mmol) and 2-bromobenzonitrile (10.00 g, 54.9 mmol) in dimethylformamide (50 mL) was heated at 95° C. for 22 hours. The reaction mixture was poured into ice water and a yellow solid was collected by filtration. Purification by flash column chromatography (40% v/v methylene chloride/hexane) followed by recrystallization from 90% ethanol yielded the title benzonitrile (3.25 g, 23%) as a yellow solid; mp 151°–153° C. $^1$H-NMR (300 MHz, d6-DMSO): 7.39 (dd, 2H, J=6.9, 2.2 Hz, aromatic) 7.73–7.75 (m, 1H, aromatic) 7.81–7.84 (m, 2H, aromatic) 8.08 (dd, 1H, J=7.7, 1.1 Hz, aromatic) 8.19 (dd, 2H, J=6.9, 2.1 Hz, aromatic). MS (CI, CH$_4$): 257 (M+1).

Analysis for C$_{13}$H$_8$N$_2$O$_2$S: Calculated: C, 60.92; H, 3.15; N, 10.83. Found: C, 60.70; H, 3.32; N, 10.99.

EXAMPLE 53

N-[3-Hydroxy-4-(phenylcarbonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (0.78 g, 4.9 mmol) in N,N-dimethylacetamide (10 mL) was added thionyl chloride (0.59 g, 4.9 mmol) and the mixture stirred at −10° to −15° C. for 1 hour. 4-Amino-2-hydroxybenzophenone (0.70 g, 3.3 mmol) was added in one portion and the reaction mixture stirred at room temperature overnight. The mixture was poured into water and the aqueous solution decanted from an oily precipitate which was dissolved in methylene chloride, dried (MgSO$_4$) and concentrated in vacuo to yield a brown oil. Purification by flash column chromatography (5% v/v ethyl acetate/methylene chloride) yielded the title propanamide as a white solid (0.83 g, 71%); mp 173°–175° C. $^1$H-NMR (250 MHz, CDCl$_3$): 1.74 (s, 3H, CH$_3$) 3.49 (s, 1H, OH) 7.14 (dd, 1H, J=8.7, 2.2 Hz, aromatic) 7.28 (d, 1H, J=2.1 Hz, aromatic),7.46–7.65 (m, 6H, aromatic) 8.49 (s, 1H, NH) 12.3 (s, 1H, phenolic OH). MS (CI, CH$_4$): (M+1).

Analysis for C$_{16}$H$_{14}$F$_3$NO$_4$: Calculated: C, 57.79; H, 3.99; N, 3.96. Found: C, 57.66; H, 4.05; N, 3.95.

4-Amino-2-hydroxybenzophenone is described in B. Arventier, H. Offenberg, Iasi, Sect. I, Chem IIc, (1), 79–85 (1965). (CA 63, 14795d).

EXAMPLE 54

N-[4-(3-Fluorophenylcarbonyl)phenyl]-3,3,3-trifluoro-2-hydroxy-2-methylpropanamide To a stirred, cooled (−20° C.) solution of 3,3,3-trifluoro-2-hydroxy-2-methylpropanoic acid (1.58 g, 10 mmol) in N,N-dimethylacetamide (15 mL) was added thionyl chloride (1.25 g, 10.5 mmol) and the mixture stirred at −20° to −10° C. for 1 hour. 4-Amino-3'-fluorobenzophenone (1.44 g, 6.7 mmol) was added in one portion and the reaction mixture stirred at room temperature overnight. The mixture was poured into water to yield an oil and a cloudy solution. The cloudy solution was decanted from the oil and filtered by suction through a pad of Celite. The Celite pad was washed with methylene chloride and the solution added to a solution of the gum in methylene chloride. The solution was dried (MgSO$_4$), filtered and the solvent removed in vacuo. The resulting oil was chromatographed on silica gel (ethyl ether), the proper fractions combined and the solvent removed to yield an oil. The oil was dissolved in 50 mL of hexane containing enough methylene chloride to give a clear solution and the solution concentrated on a steambath until the solution became cloudy. The resulting pale yellow solid was collected by filtration and dried to yield 1.51 g (63%) of N-{4-(3-fluorophenylcarbonyl)phenyl]-3,3,3-trifluoro-2-hydroxy-2-methylproanamide, mp 121.5°–3° C. $^1$H-NMR (250 MHz, $d_6$-DMSO): 1.59 (s, 3H, $CH_3$) 3.32 (s, 1H, OH) 7.46–7.60 (m, 4H, aromatic) 7.75 (d, 2H, J=9.1 Hz aromatic) 7.96 (d, 2H, J=8.2 Hz, aromatic) 10.33 (s, 1H, NH). MS (CI, $CH_4$): 356 (M+1).

Analysis for $C_{17}H_{13}F_4NO_3$: Calculated: C, 57.47; H, 3.69; N, 3.94; Found: C, 57.40; H, 3.65; N, 3.94;

The starting benzophenone was made as follows:
a. 4-Amino-3'-fluorobenzophenone

To stirred 90° C. polyphosphoric acid (150 g) was added 10.72 g (7.65 mmol) of 3-fluorobenzoic acid and 6.98 g (7.5 mmol) of aniline and the bath temperature raised to 180°–190° C. and held there for 1 hour. A solution was obtained at about 130° C. The heating bath was removed and the stirred mixture (sublimate above the solution) was treated cautiously with 60 mL of water. The mixture was stirred at 140°–155° C. for 1 hour, the heating bath removed, 50 mL of 3N HCl added, the mixture poured into 750 mL of water and filtered through a pad of Celite. The filtrate was basified with 15% sodium hydroxide and the resulting solid extracted with methylene chloride. The dried ($MgSO_4$) solution was filtered and the solvent removed to yield a brown solid. Recrystallization from ethanol-hexane (1:3) returned a greenish yellow solid that was chromatographed on silica gel (methylene chloride) to yield 4.83 g (30%) of yellow 4-amino-3'-fluorobenzophenone, mp 98°–100° C. 1H NMR (300 MHz, $CDCl_3$): 4.21 (s, 2H, $NH_2$) 6.66–6.70 (m, 2H, aromatic) 7.23–7.26 (m, 1H, aromatic) 7.39–7.51 (m, 3H, aromatic) 7.69–7.72 (m, 2H, aromatic). MS (CI, $CH_4$): 216 (M+1).

Analysis for $C_{13}H_{10}FNO$: Calculated: C, 72.55; H, 4.68; N, 6.51 Found: C, 72.66; H, 4.72; N, 6.25

EXAMPLE 55

N-(4-Phenylcarbonyl-3-fluorophenyl)-3,3,3-trifluoro-2-hydroxy-2-methylpropanamide To a stirred, cooled (−20° C.) solution of 3,3,3-trifluoro-2-hydroxy-2-methylpropanoic acid (1.19 g, 7.5 mmol) in N,N-dimethylacetamide (11 mL) was added thionyl chloride (0.92 g, 7.7 mmol) and the mixture stirred at −20° to −10° C. for 1 hour. 4-Amino-3'-fluorobenzophenone (1.08 g, 5.0 mmol) was added in one portion and the reaction mixture stirred at room temperature overnight. The mixture was poured into water to yield an oil and a cloudy solution. The cloudy solution was decanted from the oil and filtered by suction through a pad of Celite. The Celite pad was washed with methylene chloride and the solution added to a solution of the gum in methylene chloride. The solution was dried ($MgSO_4$), filtered and the solvent removed in vacuo. The resulting oil was chromatographed on silica gel (ethyl ether), the proper fractions combined and the solvent removed to yield a brown oil. The oil was dissolved in 50 mL of hexane containing enough methylene chloride (ca. 25 mL) to give a clear solution and the solution concentrated on a steambath until the solution became cloudy. The solution was scratched to start crystal growth and an additional 25 mL of hexane added. The resulting light tan solid was collected by filtration and dried to yield 1.43 g (80%) of N-(4-phenylcarbonyl-3-fluorophenyl)-3,3,3-trifluoro-2-hydroxy-2-methyl propanamide, mp 132°–4° C. $^1$H-NMR (300 MHz, $CDCl_3$): 1.78 (s, 3H, $CH_3$) 3.86 (s, 1H, OH) 7.29–7.83 (m, 8H, aromatic) 8.68 (s, 1H, NH). MS (CI, $CH_4$): 356 (M+1).

Analysis for $C_{17}H_{13}F_4NO_3$: Calculated: C, 57.47; H, 3.69; N, 3.94. Found: C, 57.42; H, 3.83; N, 3.91.

The starting benzophenone was made as follows:
a. 4-Amino-2-fluorobenzophenone

To stirred 900° C. polyphosphoric acid (150 g) was added 18.32 g (15.0 mmol) of benzoic acid and 8.33 g (7.5 mmol) of 3-fluoroaniline and the bath temperature raised to 220° C. and held there for 1 hour. A solution was obtained at about 130° C. The heating bath was removed and the stirred mixture (sublimate above the solution) was treated cautiously with 60 mL of water. The mixture was stirred at 140°–155° C. for 1 hour, the heating bath removed, 50 mL of 3N HCl added, the mixture poured into 750 mL of water and filtered through a pad of Celite. The filtrate was basified with 15% sodium hydroxide and the resulting solid collected. The 1.88 g of solid was chromatographed on silica gel (methylene chloride) to yield 1.15 g (7%) of white fluffy 4-amino-2-fluorobenzophenone, mp 133°–5° C. 1H NMR (250 MHz, $CDCl_3$): 4.20 (s, 2H, $NH_2$) 6.33–6.50 (m, 2H, aromatic) 7.27–7.55 (m, 4H, aromatic) 7.76–7.79 (m, 2H, aromatic). MS (CI, $CH_4$): 216 (M+1).

Analysis for $C_{13}H_{10}FNO$: Calculated: C, 72.55; H, 4.68; N, 6.51 Found: C, 72.20; H, 4.64; N, 6.45

EXAMPLE 56

N-[4-(3-Fluorophenylcarbonyl)phenyl]-3,3,3-trifluoro-2-hydroxy-2-trifluoromethylpropanamide To a stirred solution of 3,3,3-trifluoro-2-hydroxy-2-trifluoromethylpropanoic acid (1.17 g, 5.5 mmol) in dry tetrahydrofuran (35 mL) was added 1,1'-carbonyldiimidazole (0.89 g, 5.5 mmol). The mixture was heated at reflux for 45 minutes, then cooled to room temperature. 4-Amino-3'-fluorobenzophenone (1.08 g, 5.0 mmol) was added in one portion and the reaction mixture heated at reflux for 48 hours. Tetrahydrofuran was removed from the reaction mixture in vacuo, and the residue dissolved in ethyl ether and filtered. The filtrate was washed with 3N HCl (50 mL) and water. The ether extract was dried ($MgSO_4$) and concentrated in vacuo to an off-white solid. Purification by flash column chromatography (5% v/v ethyl ether/methylene chloride) yielded the title propanamide as a tan solid (1.13 g, 55%); mp 169°–171° C. $^1$H-NMR (300 MHz, $d_6$-DMSO): 7.50–7.64 (m, 4H, aromatic) 7.77–7.82 (m, 2H, aromatic) 7.94–7.98 (m, 2H, aromatic) 9.84 (s, 1H, NH) 10.85 (bs, 1H, OH). MS (CI, $CH_4$): 410 (M+1).

Analysis for $C_{17}H_{10}F_7NO_3$: Calculated: C, 49.89; H, 2.46; N, 3.42. Found: C, 49.60; H, 2.43; N, 3.34.

EXAMPLE 57

N-[4-(2-Fluorophenylcarbonyl)phenyl]-3,3,3-trifluoro-2-hydroxy-2-trifluoromethylpropanamide To a stirred solution of 3,3,3-trifluoro-2-hydroxy-2-trifluoromethylpropanoic acid (1.17 g, 5.5 mmol) in dry tetrahydrofuran (35 mL) was added 1,1'-carbonyldiimidazole (0.89 g, 5.5 mmol). The mixture was heated at reflux for 45 minutes, then cooled to room temperature. 4-Amino-2'-fluorobenzophenone (1.08 g, 5.0 mmol) was added in one portion and the reaction mixture heated at reflux for 48 hours. Tetrahydrofuran was removed from the reaction mixture in vacuo, and the residue dissolved in ethyl ether and filtered. The filtrate was washed with 3N HCl (50 mL) and water. The ether extract was dried (MgSO$_4$) and concentrated in vacuo to an off-white solid which was purified by flash column chromatography (5% v/v ethyl ether/methylene chloride). Recrystallization of the resulting solid from hexane yielded the title propanamide as a tan solid (0.83 g, 40%); mp 137°–139° C. $^1$H-NMR (300 MHz, d$_6$-DMSO): 7.36–7.42 (m, 2H, aromatic) 7.54–7.60 (m, 1H, aromatic) 7.63–7.69 (m, 1H, aromatic) 7.76–7.79 (m, 2H, aromatic) 7.92–7.96 (m, 2H, aromatic) 9.84 (s, 1H, NH) 10.86 (bs, 1H, OH). MS (CI, CH$_4$): 410 (M+1).

Analysis for C$_{17}$H$_{10}$F$_7$NO$_3$: Calculated: C, 49.89; H, 2.46; N, 3.42. Found: C, 50.05; H, 2.46; N, 3.36.

EXAMPLE 58

N-[3-Fluoro-4-(phenylsulfonyl)phenyl]-3,3,3-trifluoro-2-hydroxy-2-trifluoromethylpropanamide To a solution of 3,3,3-trifluoro-2-hydroxy-2-trifluoromethylpropanoic acid (1.26 g, 5.9 mmol) in dry tetrahydrofuran (35 mL) was added 1,1'-carbonyldiimidazole (0.89 g, 5.5 mmol). The mixture was heated to 45° C. in an ultrasound bath for 30 minutes, then 3-fluoro-4-phenylsulfonylbenzeneamine (1.35 g, 5.4 mmol) was added in one portion. The reaction mixture was heated at 65° C. in the ultrasound bath for 30 hours. Tetrahydrofuran was removed from the reaction mixture in vacuo, and the residue partitioned between water and ethyl ether. The aqueous layer was extracted with ethyl ether (2×50 mL), and the combined ether portions were dried (MgSO$_4$) and concentrated in vacuo to an off-white solid. The solid was dissolved in ethyl ether, treated with HCl/ethyl ether and filtered to remove unreacted 3-fluoro-4-phenylsulfonylbenzeneamine. The filtrate was concentrated in vacuo, and the resulting solid recrystallized from ethyl ether/hexane to yield the title propanamide as a white solid (0.32 g, 13%); mp 188°–189° C. $^1$H-NMR (250 MHz, d6-DMSO): 7.62–7.84 (m, 4H, aromatic) 7.91–7.94 (m, 3H, aromatic) 8.03–8.09 (m, 2H, aromatic) 9.60 (s, 1H, NH). MS (CI, CH$_4$): 446 (M+1).

Analysis for C$_{16}$H$_{10}$F$_7$NO$_4$S: Calculated: C, 43.16; H, 2.26; N, 3.15. Found: C, 43.17; H, 2.43; N, 3.07.

EXAMPLE 59

S-(−)-N-[4-(4-Pyridylsulfonyl)phenyl]-3,3,3-trifluoro-2-hydroxy-2-methylpropanamide To a stirred cooled (0° C.) of N-[4-(4-pyridylsulfonyl)phenyl]-3,3,3-trifluoro-2-hydroxy-2-methylpropanamide (30.86 g, 82 mmol) and triethylamine (13.8 mL, 99 mmol) in dry methylene chloride (500 mL), cooled to 0° C., was added 4-dimethylaminopyridine (catalytic) and S(+)-α-methoxy-α-trifluoromethylphenylacetyl chloride (24.90 g, 99 mmol), the mixture allowed to stir in the ice bath for 30 minutes and then at room temperature for 7 hours. The reaction was diluted with methylene chloride to a total volume of about 900 mL, treated with water and filtered through a pad of Celite. The organic layer was separated and the aqueous phase extracted with methylene chloride (2×700 mL). The combined organics was dried (MgSO$_4$), filtered and the solvent removed to yield a tan foam. The diastereomers were separated by repeated flash chromatography (10 v/v ethyl ether in methylene chloride). The ester (S,S) which eluted second was isolated as a white solid (7.04 g, 15%), mp 159°–160° C. Optical purity of >99% ee was determined by chiral HPLC (Ultron ES OVM column, 12% v/v acetonitrile/KH$_2$PO$_4$ (0.013M, pH 5.5), flow rate: 1 mL/min). $^1$H-NMR (250 MHz, d6-DMSO): 2.12 (s, 3H, CH$_3$) 3.60 (s, 3H, OCH$_3$) 7.51–7.60 (m, 5H, aromatic) 7.89 (d, 2H, J=2.1 Hz, aromatic) 7.95 (d, 2H, J=8.9 Hz, aromatic) 8.09 (d, 2H, J=3.8 Hz, aromatic) 8.88 (d, 2H, J=5.8 Hz, aromatic) 10.51 (s, 1H, NH). MS (CI CH$_4$): 591 (M+1). To a stirred, cooled (ice bath) suspension of the (S,S) Mosher ester (7.04 g, 11.9 mmol) in methanol (100 mL) was added a solution of sodium hydroxide (0.52 g, 13.1 mmol) in water (10 mL). After the addition of the hydroxide solution the mixture was stirred 15 minutes in the ice bath and an additional 15 minutes with the bath removed. The reaction mixture was then diluted with water to a final volume of 250 mL, the methanol removed in vacuo and the white solid collected by filtration and dried. Acidification of the filtrate gave additional material. The combined yield was 4.25 g (96%), mp 216°–217° C., [α]$_D$$^{27}$=−5.9°, c=1.02 in DMF. Optical purity was established to be >99% ee by chiral HPLC (Ultron ES OVM column, 12% v/v acetonitrile/KH$_2$PO$_4$ (0.013M, pH 5.5)). The compound was determined to be the S configuration by x-ray crystallography. $^1$H-NMR (250 MHz, d6-DMSO): 1.58 (s, 3H, CH$_3$) 7.61 (s, 1H, OH) 7.89 (dd, 2H, J=4.4, 1.5 Hz, aromatic) 8.00 (d, 2H, J=9.0 Hz, aromatic) 8.07 (d, H, J=9.0 Hz, aromatic) 8.88 (dd, 2H, J=4.5, 1.7 Hz, aromatic) 10.51 (s, 1H, NH). MS (CI CH$_4$): 375 (M+1).

Analysis for C$_{15}$H$_{13}$F$_3$N$_2$O$_4$S: Calculated: C, 48.12; H, 3.51; N, 7.48. Found: C, 48.02; H, 3.57; N, 7.41.

EXAMPLE 60

S-(−)-N-[4-(4-Pyridylsulfonyl)phenyl]-3,3,3-trifluoro-2-hydroxy-2-methylpropanamide To a stirred, cooled (−20° C.) solution of S-(−)-3,3,3-trifluoro-2-hydroxy-2-methylpropanoic acid (15.01 g, 94.9 mmol) in N,N-dimethylacetamide (225 mL) was added thionyl chloride (11.29 g, 94.9 mmol) dropwise over 5 minutes and the mixture stirred at −10° to −15° C. for one hour. 4-(4-Pyridylsulfonyl)aniline (14.82 g, 63.2 mmol) was added in one portion to the orange solution and the mixture stirred at room temperature overnight. The solution was poured into ice water (1 L) and the off-white solid that precipitated was filtered from the solution. The solid was dissolved in boiling absolute ethanol (300 mL), allowed to cool to room temperature overnight and the solid collected. A second crop was recovered after reducing the volume of the filtrate to 70 mL and allowing the resulting solution to cool to room temperature. The combined crops were recrystallized from absolute ethanol (150 mL) to yield the title propanamide (17.00 g, 74%) as a white solid; mp 215°–217° C., []$_D$$^{25}$=−5.9°, c=1.025 in dimethylformamide. Optical purity was established to be >99% ee by chiral HPLC (Ultron ES OVM column, 12% v/v acetonitrile/KH$_2$PO$_4$ (0.013 M, pH 5.5)). ($^1$H-NMR (300 MHz, d6-DMSO): 1.71 (s, 3H, CH$_3$) 7.71 (s, 1H, OH) 8.01 (d, 2H, J=4.5 Hz, aromatic) 8.12 (d, 2H, J=7.1 Hz, aromatic) 8.19 (d, 2H, J=7.1 Hz, aromatic) 9.00 (d, 2H, J=4.5 Hz, aromatic) 10.61 (s, 1H, NH). MS (CI): 375 (M+1).

Analysis for C$_{15}$H$_{13}$F$_3$N$_2$O$_4$S: Calculated: C, 48.12; H, 3.51; N, 7.48. Found: C, 48.02; H, 3.59, N, 7.42.

The starting material was made as follows:

a. S-(−)-3,3,3-Trifluoro-2-hydroxy-2-methylpropanoic acid

The solvent was removed in vacuo from a solution of R,S-(±)3,3,3-trifluoro-2-hydroxy-2-methylpropanoic acid (316.2 g, 3.0 mole) and S-(−)-α-methylbenzylamine (363.5 g, 3.0 mole) in ethanol (1.5 L), the residue triturated with toluene and the solid collected, washed with toluene and dried in vacuo. Recrystallization from 10% n-butanol in toluene returned 126.0 g of 97% enantiomerically pure (by $^{19}$F NMR) S,S salt, mp 161°–164° C. The solvent was removed from the recrystallization liquors and the residue was recrystallized three times from 10% n-butanol in toluene to yield an additional 24.0 g of 97% enantiomerically pure (by $^{19}$F NMR) S,S salt, mp 162°–165° C. The 150.0 g of 97% enantiomerically pure salt was recrystallized twice from 10% n-butanol in toluene to yield 85 g of ≧99.5% enantiomerically pure (by $^{19}$F NMR) S,S salt, mp 162.5°–164° C. $^1$H-NMR (300 MHz, CDCl$_3$): 1.25 (s, 3H, CH$_3$) 1.52 (d, 3S, J=6.8 Hz, CH$_3$) 4.16 (m, 1H, aliphatic CH) 7.25–7.35 (m, 5H, aromatic). [The R,S salt displays the acid CH$_3$ peak at 1.18 ppm and was not evident in this proton spectra]. $^{19}$F-NMR (376.5 MHz, CDCl$_3$): −79.83. [The R,S salt is shifted downfield by 13 Hz and was evident in this spectra at a level below the $^{13}$C satellite peak (0.5%)]. The liquors from the recrystallization of the 97% enantiomerically pure salt were stripped in vacuo and the residue recrystallized three times from 10% n-butanol in toluene to yield an additional 31.5 g of ≧99% enantiomerically pure (by $^{19}$F NMR) S,S salt.

The 85 g of 99.5% pure S,S salt was partioned between aqueous HCl (105 mL of concentrated HCl and 700 mL of water) and ethyl ether (400 mL). The phases were separated and the aqueous phase was further extracted with ethyl ether (5×400 mL). The dried extracts (MgSO$_4$) were filtered and the solvent removed to yield 47.0 g of S-(−)-3,3,3-trifluoro-2-hydroxy-2-methylpropanoic acid, mp 105°–108° C., $[\alpha]_D^{23}$=−18.9°, c=9.04 in methanol. $^1$H-NMR (300 MHz, CDCl$_3$): 1.67 (s, CH$_3$). MS (CI CH$_4$): 159 (M+1).

Analysis for C$_4$H$_5$F$_3$O$_3$: Calculated: C, 30.39; H, 3.19; Found: C, 30.14; H, 3.19.

The 31.5 g of ≧99% pure S,S salt was likewise partioned between aqueous HCl and ethyl ether to yield 17.4 g of S-(−)-3,3,3-trifluoro-2-hydroxy-2-methylpropanoic acid, mp 107°–109° C., $[\alpha]_D^{23}$=−18.7°, c=4.27 in methanol.

EXAMPLE 61

S-(−)-N-(4-Phenylcarbonylphenyl)-3,3,3-trifluoro-2-hydroxy-2-methylpropanamide

To a cooled (0° C.), stirred solution of N-(4-phenylcarbonylphenyl)-3,3,3-trifluoro-2-hydroxy-2-methylpropanamide (6.87 g, 20.4 mmol) and triethylamine (3.2 mL, 23 mmol) in methylene chloride (70 mL) was added 4-dimethylaminopyridine (catalytic) followed by the dropwise addition of 1S-(−)-camphanic acid chloride (5.00 g, 23.1 mmol). The mixture was stirred at room temperature for 2 hours, diluted with methylene chloride (70 mL) and washed with water, 3N HCl (200 mL) and water. The dried (MgSO$_4$) organics were filtered and the solvent removed in vacuo to yield a white foam. The diastereomers were separated by repeated flash column chromatography (0 to 3% v/v ethyl ether gradient in methylene chloride). The camphanic ester (S,S) which eluted first was isolated as a white foam (3.20 g, 30%). Optical purity of >98% de was determined by chiral HPLC (Chiralcel OD column, 15% v/v ethanol in hexane, flow rate: 1 mL/min).

$^1$H-NMR (300 MHz, d6-DMSO): 0.97 (s, 3H, CH$_3$) 1.037 (s, 3H, CH$_3$) 1.044 (s, 3H, CH$_3$) 1.58–1.61 (m, 1H, aliphatic) 2.00–2.10 (m, 5H, CH$_3$, aliphatic) 2.43–2.47 (m, 1H, aliphatic) 7.54–7.59 (m, 2H, aromatic) 7.66–7.82 (m, 7H, aromatic) 10.34 (s, 1H, NH). To a suspension of the (S,S) camphanic ester (3.20 g, 6.2 mmol) in methanol (40 mL) was added 2N NaOH (3 mL) and the yellow solution stirred at room temperature for 1 hour. The methanol was removed in vacuo, the residue treated with water and the mixture extracted with methylene chloride (2×50 mL). The dried (MgSO$_4$) organics were filtered, the solvent removed in vacuo and the white solid recrystallized from methylene chloride/hexane to yield 1.80 g (86%) of S-(−)-N-(4-phenylcarbonylphenyl)-3,3,3-trifluoro-2-hydroxy-2-methylpropanamide, mp 171°–3° C., $[\alpha]_D^{27}$=−18.8°, c=1.01 in methanol, optical purity: >98% ee by chiral HPLC (Chiralcel OD column, 15% v/v ethanol in hexane, flow rate: 1 mL/min). The compound was determined to have the S configuration by x-ray crystallography.

$^1$H-NMR (250 MHz, d6-DMSO): 1.60 (s, 3H, CH$_3$) 7.53–7.59 (m, 3H, aromatic, OH) 7.64–7.76 (m, 5H, aromatic) 7.96 (d, 2H, J=8.7 Hz, aromatic) 10.33 (s, 1H, NH). MS (CI, CH$_4$): 338 (M+1).

Analysis for C$_{17}$H$_{14}$F$_3$NO$_3$: Calculated: C, 60.54; H, 4.18; N, 4.15. Found: C, 60.49; H, 4.20; N, 4.13.

EXAMPLE 62

N-[4-(2-Pyridylcarbonyl)phenyl]-3,3,3-trifluoro-2-hydroxy-2-trifluoromethylpropanamide Tetrahydrofuran (15 ml, dry) was added to a mixture of 2,2-bis-trifluoromethyl-2-hydroxyacetic acid (1.08 g, 5.1 mmol) and 1,1'-carbonyldiimidazole (0.83 g, 5.1 mmol) while under a nitrogen atmosphere. There was an immediate evolution of carbon dioxide. The reaction was placed in an ultrasound bath at 23° C. for 15 min. The reaction was treated with 4-(2-pyridylcarbonyl)benzeneamine (1.01 g, 5.1 mmol), and heated to 43° C. in an ultrasound bath for 48 hr. The incomplete reaction was treated with a solid mixture of 2,2-bis-tri-fluoromethyl-2-hydroxyacetic acid (0.22 g, 1.04 mmol) and 1,1'-carbonyldiimidazole (0.20 g, 1.2 mmol) and heated to 53° C. in an ultrasound bath for 72 hr. The reaction was evaporated to a gold oil, which was treated with water (100 ml) and extracted with ethyl acetate (2×100 ml). the combined organic portions were dried (MgSO$_4$) and evaporated to a gold oil. Chromatography of this oil on silica gel eluting with methylenechloride/ethyl acetate (first 100:0 and then 85:15) provided a tan solid (0.37 g, 19%); mp 197°–200° C. $^1$H-NMR (250 MHz, d$_6$-DMSO): 7.68 (m, 1H, ArH), 8.00 (m, 6H, ArH), 8.74 (d, J=4.33, 1H, ArH), 9.93 (br s, 1H, OH), 10.83 (br s, 1H, NH). MS(CI,CH$_4$): 393 (M+1).

Analysis for C$_{16}$H$_{10}$F$_6$N$_2$O$_3$ Calculated: C, 48.99; H, 2.57; N, 7.14 Found: C, 49.23; H, 2.69; N, 7.33

EXAMPLE 63

N-[4-(2-Pyridyl)sulfonylphenyl]-3,3,3-trifluoro-2-hydroxy-2-trifluoromethyl-propanamide Tetrahydrofuran (5 ml,dry) was added to a mixture of 2,2-bis-trifluoromethyl-2-hydroxyacetic acid (0.98 g, 4.6 mmol) and 1,1'-carbonyldiimidazole (0.75 g, 4.6 mmol), while under a nitrogen atmosphere. There was an immediate evolution of carbon dioxide. The reaction was heated at 35° C. in an ultra-sound bath for 15 mins. The reaction was treated with a solution of 4-(2-pyridylsulfonyl) benzeneamine (1.08 g, 4.6 mmol) in dimethylformamide (11 mL, dry), heated at 46° C. for 18 hr, and then 60° C. for 24 hr. The incomplete reaction was treated with a solid mixture of 2,2-bis-trifluoromethyl-2-hydroxyacetic acid (0.22 g, 1.0 mmol) and 1,1'-carbonyldiimidazole (0.20 g, 1.2 mmol), and heated to 52° C. in an ultrasound bath for 18 hr. The reaction was evaporated to a viscous gold liquid, which was treated with water (100 ml) and extracted with ethyl acetate (2×100 ml). The combined organic portions were dried (MgSO$_4$) and evaporated to yield a gold oil. Chromatography of this oil on silica gel eluting with chloroform/methanol (98:2) provided the title compound (0.37 g, 14%) as a white solid; mp 199°–200° C. $^1$H-NMR (250 MHz, d$_6$-DMSO): 7.70 (m, 1H, ArH), 8.02 (m, 4H, ArH), 8.19 (m, 2H, ArH), 8.71 (d, J=4.0 Hz, 1H, ArH), 9.88 (s, 1H, OH), 10.94 (s, 1H, NH). MS(CI,CH$_4$): 429 (M+1)

Analysis for C$_{15}$H$_{10}$F$_6$N$_2$O$_4$S: Calculated: C, 42.06; H, 2.35. N, 6.53 Found: C, 41.99; H, 2.34; N, 6.57

EXAMPLE 64

N-[4-(4-Pyridylsulfonyl)phenyl]-3,3,3-trifluoro-2-hydroxy-2-trifluoromethyl-propanamide Tetrahydrofuran (5 ml,dry) was added to a mixture of 2,2-bis-trifluoromethyl-2-hydroxyacetic acid (1.29 g, 6.1 mmol) and 1,1'-carbonyldiimidazole (.99 g, 6.1 mmol), while under a nitrogen atmosphere. There was an immediate evolution of carbon dioxide. The reaction was heated at 35° C. for 15 min. The reaction was treated with a solution of 4-(4-pyridylsulfonyl)benzeneamine (1.43 g, 6.1 mmol) in dimethylformamide (15 ml,dry), and heated to 69° C. in an ultrasonic bath for 19.5 hrs. The reaction was poured into water (300 ml), and extracted with ethyl ether (3×300 ml). The combined organic portions were evaporated and preabsorbed onto silica gel (10 gm). Chromatography of this material on silica gel, eluting with methylene chloride/ethyl acetate (first 100:0 and then 70:30) provided a white solid. Recrystallization from acetone gave starting 4-(4-pyridylsulfonyl)benzeneamine. The filtrate was evaporated and chromatographed on silica gel eluting with chloroform/methanol (first 100:0 and then 98:2) provided the title compound (0.115 g, 6%) as a white solid; mp 235°–237° C. $^1$H-NMR (250 MHz,d$_6$-DMSO): 7.90 (d, J=4.6, 2H, ArH), 8.04 (d, 4H, ARM), 8.89 (d, J=4.68 Hz, 2H, ArH), 9.90 (s, 1H, OH), 10.97 (s, 1H, NH). MS(CI,CH$_4$): 429 (M+1)

Analysis for C$_{15}$H$_{10}$F$_6$N$_2$O$_4$S: Calculated: C, 42.06; H, 2.35; N, 6.53 Found: C, 42.11; H, 2.46; N, 6.38

EXAMPLE 65

N-[3-(Pyridylsulfonyl)phenyl]-3,3,3-trifluoro-2-hydroxy-2-trifluoromethyl-propanamide Tetrahydrofuran (15 ml, dry) was added to a mixture of 2,2-bis-trifluoromethyl-2-hydroxyacetic acid (0.44 g, 2.1 mmol) and 1,1'-carbonyldiimidazole (0.34 g, 2.1 mmol), while under a nitrogen atmosphere. There was an immediate evolution of carbon dioxide. The reaction was heated to 35° C. in an ultrasound bath for 15 min. The reaction was treated with 4-(3-pyridylsulfonyl)benzeneamine (0.49 g, 2.1 mmol), and heated to 55° C. in an ultrasound bath for 42 hr. The reaction was evaporated to a viscous yellow oil. Chromatography of this oil on silica gel eluting with methylene chloride/ethyl acetate (85:15) followed by chromatography of silica gel eluting with chloroform/methanol (98:2) provided the title compound (0.09 g, 10%) as an off-white solid; mp 264°–267° C. $^1$H-NMR (250 MHz, d$_6$-DMSO): 7.68 (m, 1H, ArH), 8.03 (m, 4H, ArH), 8.35 (dr, J=8.4, J=1.9 Hz, 1H, ArH), 8.86 (dd, J=10.0, J=1.28 Hz, 1H, ArH), 9.13 (d, J=2.35, 1H, ArH), 9.87 (s, 1H, OH), 10.94 (s, 1H, NH). MS(CI,CH$_4$): 429 (M+1)

Analysis for C$_{15}$H$_{10}$F$_6$N$_2$O$_4$S.1/2 H$_2$O Calculated: C, 41.19; H, 2.53; N, 6.41 Found: C, 41.25; H, 2.46; N, 6.19

EXAMPLE 66

N-[4-(Phenylcarbonyl)phenyl]-3,3-difluoro-2-hydroxy-2-difluoromethylpropanamide

To a solution of 2,2,-bis-difluoromethyl-2-hydroxy-acetic acid (1.76 g, 10 mmole) in tetrahydrofuran(40 ml) was added carbonyl diimidazole (0.81 g, 5 mmole). The flask was placed in a sonic bath and the reaction sonicated for 20 minutes followed by addition of 4-aminobenzophenone. The reaction was sonicated for 18 hours. The reaction mixture was filtered and the filtrate evaporated to dryness. The recovered pasty solid was washed with ether and the combined ether washings evaporated. The recovered solid was crystallized from ethyl acetate/hexane to give the title compound (0.89 g, 25%) as yellow crystals; mp 139°–142° C.

$^1$H-NMR (300 MHz, d$_6$-DMSO): 6.48(t, J=53.7 Hz, 2H, HCF$_2$); 7.53–7.77 (m, 7H, ArH, OH); 7.95–7.98(m, 3H, ArH); 10.43 (s, 1H, NH). MS(CI,CH$_4$): 356(M+1, 100%).

Analysis for C$_{17}$H$_{13}$F$_4$NO$_3$.0.25 H$_2$O Calculated: C, 56.75; H, 3.78; N, 3.89. Found: C, 57.03; H, 3.39; N, 3.84.

EXAMPLE 67

N-[4-(2-Pyridylsulfonyl)phenyl]-3,3-difluoro-2-hydroxy-2-difluoromethyl propionamide To a solution of 2,2-bis-difluoromethyl-2-hydroxyacetic acid (0.5 g, 2.84 mmole) in dimethylacetamide (10 ml) at −10° C. was added thionyl chloride (0.34 g, 2.84 mmol) dropwise. The resulting solution was stirred at −10° C. for approximately 30 min. 4-(2-Pyridylsulfonyl)aniline (0.58 g, 2.5 mmol) was added and the reaction mixture was stirred overnight at room temperature. The reaction mixture was then poured into water, and sodium bicarbonate solution was added to give a pH of 7–7.5. A brown colored precipitate was formed. The solid was filtered, washed with water, and dried. Crystallization and decoloration (charcoal) from ethyl acetate/methanol/hexane gave the title compound (0.42 g, 43%) as off-white leaves; mp 200°–202° C.

$^1$H-NMR(300 MHz, d$_6$-DMSO): 6.45 (t, J=54.09 Hz, 2H, HCF$_2$), 7.68(t, J=6.24 Hz, 1H, ArH), 7.92–8.03 (m, 5H, ArH, OH), 8.11–8.21 (m, 2H, ArH), 8.68 (d, J=4.47 Hz, 1H, ArH), 10.54 (s, 1H, NH). MS(CI,CH$_4$): 393 (M+1, 100%).

Analysis for C$_{15}$H$_{12}$F$_4$N$_2$O$_4$S: Calculated: C, 45.92; H, 3.08; N, 7.14 Found: C, 45.89; H, 3.17; N, 7.12

EXAMPLE 68

N-[4-(Phenylsulfonyl)phenyl]-3,3-difluoro-2-hydroxy-2-difluoromethyl propionamide To a solution of 2,2-bis-difluoromethyl-2-hydroxyacetic acid (0.5 g, 2.84 mmoles) in dimethylacetamide (10 ml) at −10° C. was added thionyl chloride (0.34 g, 2.84 mmoles) dropwise. The resulting solution was stirred at −10° C. for approximately 30 mins. 4-(Phenylsulfonyl) aniline (0.58 g, 2.5 mmoles) was added and the reaction mixture was stirred overnight at room temperature. The reaction mixture was then poured into water, sodium bicarbonate solution added to give a pH of 7 and extracted with ethyl acetate. The ethyl acetate extracts were combined, washed with water, brine, dried (Na$_2$SO$_4$), decolorized (charcoal), and evaporated. The crude solid was dissolved in ether, clarified by filtration, and evaporated. Crystallization from methanol/water gave the title compound (0.56 g, 57%) as white, silky needles; mp 105°–108° C. $^1$H-NMR (300 H B z, d$_6$-DMSO) 6.44 (t, J=53.94 Hz, 2H, HCF$_2$), 7.58–7.68(m, 3H, ArH), 7.92–8.01 (m, 7H, ArH, OH), 10.51 (s, 1H, NH). MS(CI,CH$_4$): 392 (M+1, 100%).

Analysis for C$_{16}$H$_{13}$F$_4$NO$_4$S: Calculated: C, 49.11; H, 3.35; N, 3.58. Found: C, 49.15; H, 3.48; N, 3.54

EXAMPLE 69

N-[4-(2-Pyridylcarbonyl)phenyl]-3,3-difluoro-2-hydroxy-2-difluoromethyl propionamide To a solution of 2,2-bis-difluoromethyl-2-hydroxyacetic acid (0.5 g, 2.84 mmoles) in dimethylacetamide (10 mL) at −10° C. was added thionyl chloride (0.34 g, 2.84 mmoles) dropwise. The resulting solution was stirred at −10° C. for approximately 30 mins. 4-(2-Pyridylcarbonyl)aniline (0.58 g, 2.5 mmoles) was added and the reaction mixture was stirred overnight at room temperature. The reaction mixture was then poured into water, sodium bicarbonate solution added to give a pH of 7 and extracted with ethyl acetate. The ethyl acetate extracts were combined, washed with water, brine, dried ($Na_2SO_4$), decolorized (charcoal), and evaporated. The crude solid was dissolved in ether, clarified by filtration, and evaporated to give a yellow orange gum. Crystallization from methylene chloride/hexane gave the title compound (0.35 g, 35%) as a tan solid; mp 158°–161° C. $^1$H-NMR (300 MHz, $d_6$-DMSO); 6.48(t, J=54.12 Hz, 2H, $HCF_2$), 7.67(t, J=6.18 Hz, 1H, ArH), 7.91–8.10 (m, 7H, ArH, OH), 8.73 (d, J=7.35 Hz, 1H, ArH), 10.40 (s, 1H, NH). MS(CI),$CH_4$: 357(M+H, 100%).

Analysis for $C_{16}H_{12}F_4N_2O_3$: Calculated: C, 53.94; H, 3.39; N, 7.86 Found: C, 53.76; H, 3.41; N, 7.87

EXAMPLE 70

N-[4-(2-Pyrimidinylsulfonyl)phenyl]-3,3-difluoro-2-hydroxy-2-difluoromethyl propionamide To a solution of 2,2-bis-difluoromethyl-2-hydroxyacetic acid (0.5 g, 2.84 mmoles) in di ethyl acetamide (10 ml) at −10° C. was added thionyl chloride (0.34 g, 2.84 mmoles) dropwise. The resulting solution was stirred at −10° C. for approximately 30 mins. 4-(2-pyrimidylsulfonyl)aniline (0.59 g, 2.5 mmoles) was added and the reaction mixture was stirred overnight at room temperature. The reaction mixture was poured into water, and sodium bicarbonate solution was added to give a pH of 7–7.5. A dark colored precipitate was formed that was filtered, washed with water and dried. The crude material was preabsorbed onto silica gel and chromatographed on silica gel eluting with 70–80% ethyl/acetate/hexane. Evaporation of product-containing fractions and crystallization from methylene chloride/methanol/hexane gave the title compound (0.33 g, 34%) as a white solid; mp 209°–210° C. $^1$H-NMR (300 MHz, $d_6$-DMSO):6.46(t, J=54.06 Hz, 2H, $HCF_2$), 7.78 (t, J=4.8 Hz, 1H, ArH), 7.95–7.98(m, 3H, ArH, OH), 8.02–8.06(m, 2H, ArH), 9.01 (d, J=5.01 Hz, 2H, ArH), 10.58 (s, 1H, NH). MS(CI):394(M+1, 100%).

Analysis for $C_{14}H_{11}F_4N_3O_4S$: Calculated: C, 42.75; H, 2.82; N, 10.68 Found: C, 42.55; H, 2.80; N, 10.57

EXAMPLE 71

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
| --- | --- |
| (a) Tablet | |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |

|  | mg/tablet |
| --- | --- |
| (b) Capsule | |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

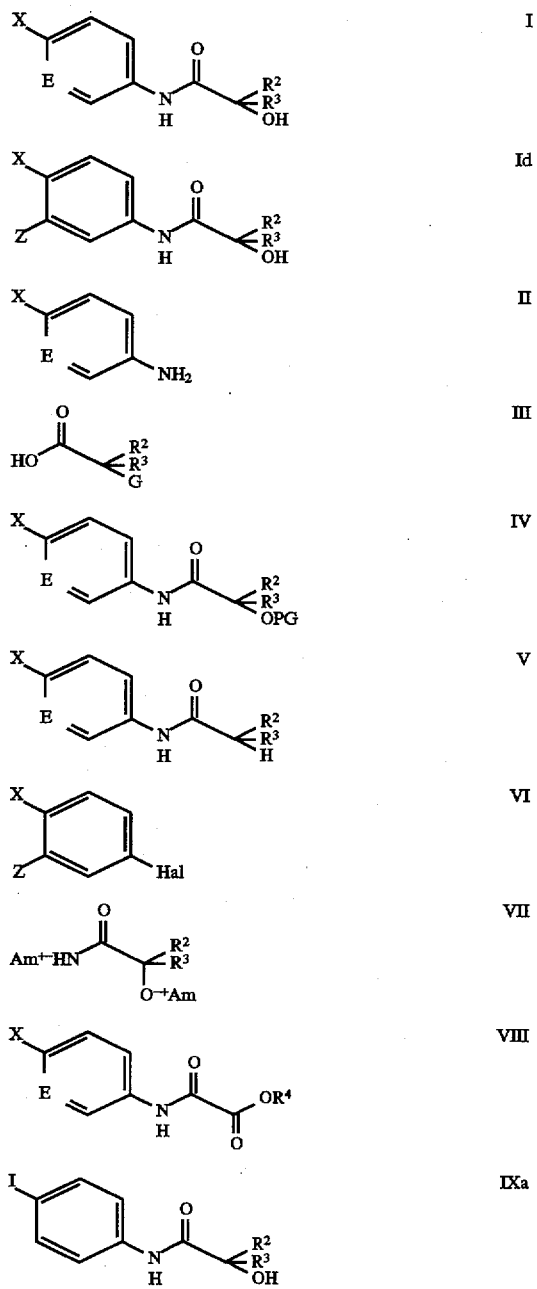

FORMULAE

-continued
FORMULAE

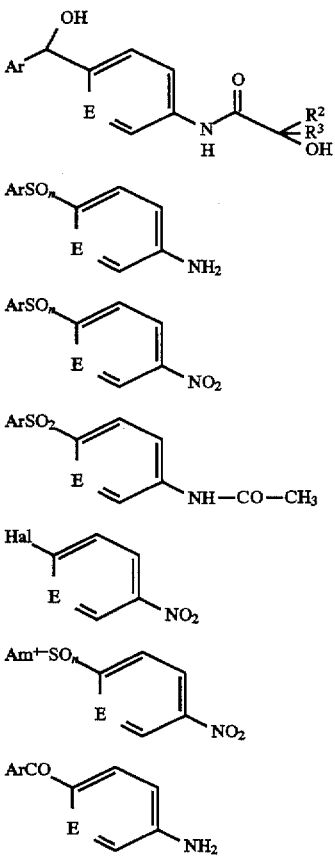

What is claimed is:

1. A method of preparing an amide of the formula

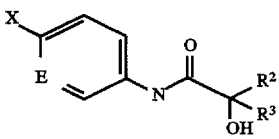

comprising the step of reacting a compound of the formula

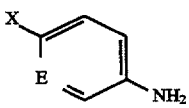

with an acid of the formula

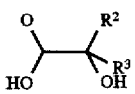

wherein

E is selected from nitrogen and CZ wherein C is a ring carbon and Z is a substituent defined below, wherein:
when E is CZ, X and Z are selected from the group consisting of:
(A) X is ArY wherein Y is a linking group selected from carbonyl, sulfinyl, and sulfonyl and Ar is selected from the group consisting of:
phenyl substituted with 0–2 substituents selected from halo, hydroxy, cyano, (1–4C)alkyl, and (1–4C)alkoxy, provided that the 4-position of said phenyl may be substituted by fluoro only, and that the said phenyl may not be 3,5-disubstituted;
six-membered heteroaryl rings containing 1–2 nitrogen atoms as the only heteroatoms;
five-membered heteroaryl rings containing from 1–2 heteroatoms selected from nitrogen, oxygen, and sulfur; provided that Ar is not 3-chlorophenyl, 3-bromophenyl, 3-iodophenyl, 3-(1–4C) alkylphenyl, or 4-pyridyl when Y is carbonyl, and that Ar is not 5-pyrimidinyl when Y is sulfonyl or carbonyl; and
Z is selected from hydrogen, cyano, halo, hydroxy, (1–4C)alkyl, and (1–4C)alkoxy;
(B) X is cyano and Z is selected from the group consisting of phenylthio, phenylsulfinyl, and phenylsulfonyl the phenyl rings of which are substituted with 0–2 substituents selected from halo, hydroxy, cyano, nitro, (1–4C)alkyl, and (1–4C)alkoxy;
when E is nitrogen, X is independently selected from any of the values for X given above in (A);
$R^2$ and $R^3$ are independently selected from the group consisting of (1–3C)alkyl substituted by from 0 to 2k+1 groups selected from fluoro and chloro wherein k is the number of carbon atoms in the said (1–3C)alkyl, provided that $R^2$ and $R^3$ are not both methyl; or
together, with the carbon atom to which both $R^2$ and $R^3$ are attached, form a 3–5 membered cycloalkyl ring optionally substituted by from 0 to 2m-2 fluoro groups wherein m is the number of carbon atoms in said ring.

2. The method of claim 1 wherein
E is CZ and
X and Z are selected from the group consisting of:
(A) X is ArY wherein
Y is a linking group selected from carbonyl, sulfinyl, and sulfonyl and Ar is selected from the group consisting of phenyl, 2-, 3- and 4-fluorophenyl, 2- and 3-chlorophenyl, 2- and 3-cyanophenyl, 2- and 3-hydroxyphenyl, 2- and 3-methoxyphenyl, 2- and 3-methylphenyl, 2-, 3-, and 4-pyridyl, 2- and 4-pyrimidinyl, 3- and 4-isothiazolyl, 2- and 4oxazolyl, 2- and 4-thiazolyl, 2- and 3-furyl, and 2- and 3-thienyl;
Z is selected from hydrogen, cyano, halo, hydroxy, (1–2C)alkyl, and (1–2C)alkoxy;
(B) X is CN, Z is phenylsulfonyl;
$R^2$ and $R^3$ are independently selected from the group consisting of (1–3C)alkyl substituted by from 0 to 2k+1 fluoro groups wherein k is the number of carbon atoms in the said (1–3C)alkyl, provided that $R^2$ and $R^3$ are not both methyl.

3. The method of claim 1 wherein
X is ArY and wherein Ar, Y, and Z are selected from the group consisting of:
(i) Y is sulfonyl, Z is hydrogen, and Ar is selected from the group consisting of:
phenyl substituted with 0–1 substituents, selected from phenyl, 2-, 3-, and 4-fluorophenyl, 2- and 3-chlorophenyl, 2- and 3-methoxyphenyl, 2- and 3-cyanophenyl, 2- and 3-hydroxyphenyl, and 2- and 3-methylphenyl;
six-membered heteroaryl rings selected from 2-, 3- and 4-pyridyl, and 2-pyrimidinyl;
five-membered heteroaryl rings selected from 2-thienyl and 2-thiazolyl;
(ii) Y is sulfonyl, Ar is phenyl or 4-pyridyl, and Z is selected from the group consisting of cyano, fluoro, hydroxy, methoxy and methyl; and (iii) Y is carbonyl, Z is hydrogen, and Ar is selected from the group consisting of phenyl and 2-pyridyl; and $R^2$ and $R^3$ are independently selected from the group consisting of
  (i) $R^2$ is trifluoromethyl and $R^3$ is selected from methyl, ethyl, and trifluoromethyl; and
  (ii) $R^2$ is difluoromethyl and $R^3$ is difluoromethyl.

4. A method of preparing N-[4-(phenylcarbonyl)-phenyl]-3,3,3-trifluoro-2-hydroxy-2-methyl-propanamide comprising the step of reacting 4-aminobenzophenone and 3,3,3-trifluoro-2-hydroxy-2-methylpropanoic acid.

* * * * *